US009989531B2

(12) United States Patent
Moreau et al.

(10) Patent No.: US 9,989,531 B2
(45) Date of Patent: Jun. 5, 2018

(54) COMPOSITION COMPRISING A CELL SAMPLE FROM A SUBJECT WITH SCOLIOSIS AND A REAGENT FOR DETECTING PTPμ OR PIPK1Y

(71) Applicant: Chu Sainte-Justine, Montréal (CA)

(72) Inventors: Alain Moreau, Montréal (CA); Marie-Yvonne Akoume Ndong, Montréal (CA); Mohamed Elbakry, Montréal (CA)

(73) Assignee: Chu Sainte-Justine (CA)

( * ) Notice: Subject to any disclaimer, the term of this patent is extended or adjusted under 35 U.S.C. 154(b) by 0 days. days.

(21) Appl. No.: 14/898,904

(22) PCT Filed: Jun. 17, 2014

(86) PCT No.: PCT/CA2014/050568
§ 371 (c)(1),
(2) Date: Dec. 16, 2015

(87) PCT Pub. No.: WO2014/201560
PCT Pub. Date: Dec. 24, 2014

(65) Prior Publication Data
US 2016/0291016 A1   Oct. 6, 2016

Related U.S. Application Data

(60) Provisional application No. 61/835,698, filed on Jun. 17, 2013.

(51) Int. Cl.
| | |
|---|---|
| *G01N 33/50* | (2006.01) |
| *G01N 21/53* | (2006.01) |
| *C07H 21/04* | (2006.01) |
| *C07K 16/18* | (2006.01) |
| *G01N 33/573* | (2006.01) |
| *G01N 33/68* | (2006.01) |
| *C12N 15/113* | (2010.01) |
| *C12Q 1/68* | (2018.01) |
| *C12Q 1/42* | (2006.01) |
| *C12Q 1/48* | (2006.01) |

(52) U.S. Cl.
CPC ....... *G01N 33/573* (2013.01); *C12N 15/1137* (2013.01); *C12Q 1/42* (2013.01); *C12Q 1/485* (2013.01); *C12Q 1/6883* (2013.01); *C12Y 207/01068* (2013.01); *C12Y 301/03048* (2013.01); *G01N 33/5047* (2013.01); *G01N 33/5091* (2013.01); *G01N 33/6893* (2013.01); *C12N 2310/14* (2013.01); *C12N 2320/30* (2013.01); *C12Q 2600/118* (2013.01); *C12Q 2600/158* (2013.01); *G01N 2333/912* (2013.01); *G01N 2333/916* (2013.01); *G01N 2333/91215* (2013.01); *G01N 2800/10* (2013.01); *G01N 2800/50* (2013.01); *G01N 2800/56* (2013.01)

(58) Field of Classification Search
None
See application file for complete search history.

(56) References Cited

U.S. PATENT DOCUMENTS

2006/0003327 A1* 1/2006 Achiron .............. C12Q 1/6883
435/7.23
2008/0131877 A1   6/2008 Wise

FOREIGN PATENT DOCUMENTS

| EP | 2132568 B1 | 5/2013 |
|---|---|---|
| WO | 03073102 A1 | 9/2003 |
| WO | 2008113174 A1 | 9/2008 |
| WO | 2008119170 A1 | 10/2008 |
| WO | 2010040234 A1 | 4/2010 |

OTHER PUBLICATIONS

Mah et al, 2010. Adolescent Health, Medicine and Therapeutics. 1:31-43.*
Mourton et al., "The PTPm protein-tyrosine phosphatase bonds and recruits the scaffolding protein RACK1 to cell-cell contact", the Journal of Biological Chemistry, May 4, 2001 (Apr. 5, 2001), 276(18), pp. 14896-14901 Whole document.
Burwell et al., "Pathogenesis of adolescent idiopathic scoliosis in girls—a double neuro-osseous theory involving disharmony between two nervous systems, somatic and autonomic expressed in the spine and trunk: possible dependency on sympathetic nervous system and hormones with implications for medical therapy", Scoliosis, 2009, 4 (24), pp. 1-40 Whole document.
International Search Report for Application No. PCT/CA2014/050568 dated Aug. 14, 2014.
Supplementary Partial European Search Report for Application No. EP1481448 dated Nov. 28, 2016.
Supplementary Partial European Search Report for Application No. EP14814185 dated Jan. 2, 2017.
Moreau A et al: "Molekulare and genetische Aspekte der idiopathischen Skoliose Bluttest bei idiopathischer Skoliose", Orthopaede, Springer Verlag, Berlin, DE, vol. 38, No. 2, Feb. 1, 2009 (Feb. 1, 2009), pp. 114-116, XP008144092.
Bagnall Keith M et al: "The International Research Society of Spinal Deformities (IRSSD) and its contribution to science", Scoliosis, Biomed Central LTD, LO, vol. 4n, No. 1, Dec. 22, 2009 (Dec. 22, 2009), p. 28, XP021069416.

(Continued)

*Primary Examiner* — Zachary Howard
(74) *Attorney, Agent, or Firm* — Lerner, David, Littenberg, Krumholz & Mentlik, LLP

(57) ABSTRACT

Methods of stratifying a subject having or at risk for developing adolescent idiopathic scoliosis (AIS) into diagnostically or clinically useful subclasses are provided. The stratification is based on the subject's PTPμ expression and/or activity and/or PIPK1γ expression and/or activity. Also provided are methods of predicting the risk of developing a scoliosis also based on the subject's PTPμ expression and/or activity and/or PIPK1γ expression and/or activity; and methods of increasing GiPCR signaling in cells of a subject in need thereof comprising administering to the subject's cells an effective amount of an inhibitor of PIPK1γ tyrosine phosphorylation; an activator of PIPK1Y tyrosine dephosphorylation; and/or an inhibitor of PIPK1γ expression and/or activity.

22 Claims, 32 Drawing Sheets

(56) References Cited

OTHER PUBLICATIONS

Alain Moreau et al: "Scientific Program Abstracts: High Circulating Levels of Osteopontin are Associated with Idiopathic Scoliosis Onset and Spinal Deformity Progression: Paper #79", Spine: Affiliated Society Meeting Abstracts:, No. suppl 3, Sep. 23, 2009 (Sep. 23, 2009), XP055325248.
Marie-Yvonne Akoume et al: "Cell-based Assay Protocol for the Prognostic Prediction of Idiopathic Scoliosis Using Cellular Dielectric Spectroscopy", Journal of Visualized Experiments, vol. 80, No. E50768, Oct. 16, 2013 (Oct. 16, 2013), pp. 1-9, XP055323360.
Moreau Alain et al: "Melatonin signaling dysfunction in adolescent idiopathic scoliosis", Spine, Lippincott Williams & Wilkins, US, vol. 29, No. 16, Aug. 15, 2004 (Aug. 15, 2004), pp. 1772-1781, XP009129278.
Kareen Letellier et al: "Estrogen cross-talk with the melatonin signaling pathway in human osteoblasts derived from adolescent idiopathic scoliosis patients", Journal of Pineal Research, Munksgaard, Copenhagen, DK, vol. 45, No. 4, Nov. 1, 2008 (Nov. 1, 2008), pp. 383-393, XP008144091.
Marie-Yvonne Akoume et al: "Cell-Based Screening Test for Idiopathic Scoliosis Using Cellular Dielectric Spectroscopy", Spine (Phila Pa 1976) 35 (13), E601-E608, Jun. 1, 2010.
Azeddine, et al., Molecular Determinants of Melatonin Signaling Dysfunction in Adolescent Idiopathic Scoliosis, Clin Orthop Relat Res., Sep. 2007; 462:45-52.
Burwell, R.G., Aetiology of idiopathic scoliosis: current concepts, Pediatr Rehabil. Jul.-Dec. 2003; 6(3-4):137-170.
Calderwood, "Integrin activation" Journal of Cell Science 2004 117, 657-666, The Company of Biologists Ltd, Published online Jan. 30, 2004.
Clover, et al., "Integrin subunit expression by human osteoblasts and osteoclasts in situ and in culture," J Cell Sci. Sep. 1992; 103 (Pt 1): 267-271.
Di Paolo, et al., "Recruitment and regulation of phosphatidylinositol phosphate kinase type 1g by the FERM domain of talin," Nature, vol. 420, Nov. 7, 2002.
Dickson, The Etiology and Pathogenesis of Idiopathic Scoliosis, Acta Orthop Belg. Jan. 1992; 58 Suppl 1:21-25.
Giannoni, et al., "The mechanosensitivity of cartilage oligomeric matrix protein (COMP)," Biorheology. Mar. 2003; 40 (1-3):101-109.
Gronthos, et al., "Integrin Expression and Function on Human Osteoblast-like Cells," J Bone Miner Res. Aug. 1997; 12(8)1189-1197.
Grzesik, et al., "Bone Matrix RGD Glycoproteins : Immunolocalization and Interaction with Human Primary Osteoblastic Bone Cells In Vitro," J Bone Miner Res. Apr. 1994;9(4):487-496.
Hughes, et al., "Suppression of Integrin Activation: A Novel Function of a Ras/Raf-Initiated MAP Kinase Pathway," Cell, vol. 88, 521-530, Feb. 21, 1997.
Hynes, et al., "Integrins: Bidirectional, Allosteric Signaling Machines," Cell, vol. 110, 673-687, Sep. 20, 2002.
Kane, "Scoliosis Prevalence: A Call for a Statement of Terms," Clinical Orthopaedics and Related Research, No. 126, 44-46, Jul.-Aug. 1977.
Ling, et al., "Tyrosine phosphorylation of type Ig phosphatidylinositol phosphate kinase by Src regulates an integrin-talin switch," the Journal of Cell Biology, vol. 163, No. 6, Dec. 22, 2003, 1339-1349.
Martel, et al., "Conformation, Localization, and Integrin Binding of Talin Depend on Its Interaction with Phosphoinositides," the Journal of Biological Chemistry vol. 276, No. 24, Issue of Jun. 15, 2001, pp. 21217-21227.
Machida, "Cause of Idiopathic Scoliosis," Spine (Phila Pa 1976). Dec. 15, 1999;24(24):2576-2583.
Machida, et al., "Experimental scoliosis in melatonin-deficient C57BL/6J mice without pinealectomy," J Pineal Res. Aug. 2006;41(1):1-7.
Moursi, et al., "Interactions between integrin receptors and fibronectin are required for calvarial osteoblast differentiation in vitro," J Cell Sci. Sep. 1997; 110 (Pt 18):2187-2196.
Oyama, et al., "Bipedal ambulation induces experimental scoliosis in C57BL/6J mice with reduced plasma and pineal melatonin levels," J Pineal Res. Apr. 2006; 40(3):219-224.
Pistone, et al., "Integrin Synthesis and Utilization in Cultured Human Osteoblasts," Cell Biol Int. Jul. 1996; 20(7):471-479.
Sakamoto, et al., "Involvement of Nectin in Inactivation of Integrin avb3 after the Establishment of Cell-Cell Adhesion," the Journal of Biological Chemistry vol. 283, No. 1, pp. 496-505, Jan. 4, 2008.
Tozer, et al., "Ligand binding and affinity modulation of integrins," Biochem Cell Biol. Jan. 1996; 74(6):785-798.
Verdonk, et al., "Cellular Dielectric Spectroscopy: A Label-Free Comprehensive Platform for Functional Evaluation of Endogenous Receptors," Assay Drug Dev Technol. Oct. 2006; 4(5):609-619.

* cited by examiner

FIG. 1A
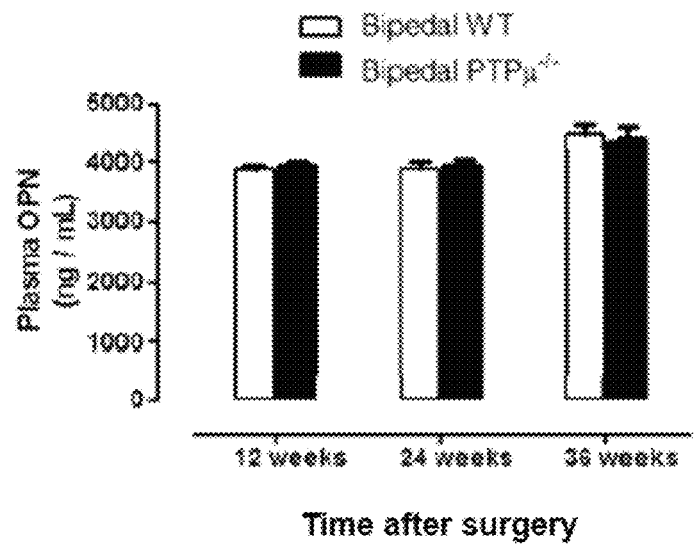
FIG. 1B
| | WT | PTPμ-/- |
|---|---|---|
| Total number | 60 | 60 |
| Scoliotic | 33 (55 %) | 51 (85 %) |
| Non scoliotic | 27 (45 %) | 9 (15 %) |
FIG. 1C
WT
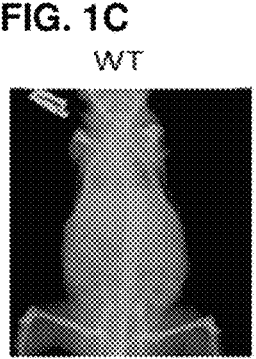
FIG. 1D
PTPμ-/-
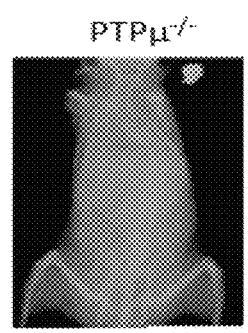

```
PIPK1γ_isoform_2    MELEVPDEAESAEAGAVPSEAAWAAESGAAAGLAQKKAAPTEVLSMTAQPGPGHGKKLGH  60
PIPK1γ_isoform_4    MELEVPDEAESAEAGAVPSEAAWAAESGAAAGLAQKKAAPTEVLSMTAQPGPGHGKKLGH  60
PIPK1γ_isoform_1    MELEVPDEAESAEAGAVPSEAAWAAESGAAAGLAQKKAAPTEVLSMTAQPGPGHGKKLGH  60
PIPK1γ_isoform_3    MELEVPDEAESAEAGAVPSEAAWAAESGAAAGLAQKKAAPTEVLSMTAQPGPGHGKKLGH  60
PIPK1γ_isoform_X2   MELEVPDEAESAEAGAVPSEAAWAAESGAAAGLAQKKAAPTEVLSMTAQPGPGHGKKLGH  60
                    ************************************************************

PIPK1γ_isoform_2    RGVDASGETTYKKTTSSTLKGAIQLGIGYTVGHLSSKPERDVLMQDFYVVESIFFPSEGS  120
PIPK1γ_isoform_4    RGVDASGETTYKKTTSSTLKGAIQLGIGYTVGHLSSKPERDVLMQDFYVVESIFFPSEGS  120
PIPK1γ_isoform_1    RGVDASGETTYKKTTSSTLKGAIQLGIGYTVGHLSSKPERDVLMQDFYVVESIFFPSEGS  120
PIPK1γ_isoform_3    RGVDASGETTYKKTTSSTLKGAIQLGIGYTVGHLSSKPERDVLMQDFYVVESIFFPSEGS  120
PIPK1γ_isoform_X2   RGVDASGETTYKKTTSSTLKGAIQLGIGYTVGHLSSKPERDVLMQDFYVVESIFFPSEGS  120
                    ************************************************************

PIPK1γ_isoform_2    NLTPAHHFQDFRFKTYAPVAFRYFRELFGIRPDDYLYSLCNEPLIELSNPGASGSLFYVT  180
PIPK1γ_isoform_4    NLTPAHHFQDFRFKTYAPVAFRYFRELFGIRPDDYLYSLCNEPLIELSNPGASGSLFYVT  180
PIPK1γ_isoform_1    NLTPAHHFQDFRFKTYAPVAFRYFRELFGIRPDDYLYSLCNEPLIELSNPGASGSLFYVT  180
PIPK1γ_isoform_3    NLTPAHHFQDFRFKTYAPVAFRYFRELFGIRPDDYLYSLCNEPLIELSNPGASGSLFYVT  180
PIPK1γ_isoform_X2   NLTPAHHFQDFRFKTYAPVAFRYFRELFGIRPDDYLYSLCNEPLIELSNPGASGSLFYVT  180
                    ************************************************************

PIPK1γ_isoform_2    SDDEFIIKTVMHKEAEFLQKLLPGYYMNLNQNPRTLLPKFYGLYCVQSGGKNIRVVVMNN  240
PIPK1γ_isoform_4    SDDEFIIKTVMHKEAEFLQKLLPGYYMNLNQNPRTLLPKFYGLYCVQSGGKNIRVVVMNN  240
PIPK1γ_isoform_1    SDDEFIIKTVMHKEAEFLQKLLPGYYMNLNQNPRTLLPKFYGLYCVQSGGKNIRVVVMNN  240
PIPK1γ_isoform_3    SDDEFIIKTVMHKEAEFLQKLLPGYYMNLNQNPRTLLPKFYGLYCVQSGGKNIRVVVMNN  240
PIPK1γ_isoform_X2   SDDEFIIKTVMHKEAEFLQKLLPGYYMNLNQNPRTLLPKFYGLYCVQSGGKNIRVVVMNN  240
                    ************************************************************

PIPK1γ_isoform_2    ILPRVVKMHLKFDLKGSTYKRRASKKEKEKSFPTYKDLDFMQDMPEGLLLDADTFSALVK  300
PIPK1γ_isoform_4    ILPRVVKMHLKFDLKGSTYKRRASKKEKEKSFPTYKDLDFMQDMPEGLLLDADTFSALVK  300
PIPK1γ_isoform_1    ILPRVVKMHLKFDLKGSTYKRRASKKEKEKSFPTYKDLDFMQDMPEGLLLDADTFSALVK  300
PIPK1γ_isoform_3    ILPRVVKMHLKFDLKGSTYKRRASKKEKEKSFPTYKDLDFMQDMPEGLLLDADTFSALVK  300
PIPK1γ_isoform_X2   ILPRVVKMHLKFDLKGSTYKRRASKKEKEKSFPTYKDLDFMQDMPEGLLLDADTFSALVK  300
                    ************************************************************

PIPK1γ_isoform_2    TLQRDCLVLESFKIMDYSLLLGVHNIDQHEREROAQGAQSTSDEKRPVGQKALYSTAMES  360
PIPK1γ_isoform_4    TLQRDCLVLESFKIMDYSLLLGVHNIDQHEREROAQGAQSTSDEKRPVGQKALYSTAMES  360
PIPK1γ_isoform_1    TLQRDCLVLESFKIMDYSLLLGVHNIDQHEREROAQGAQSTSDEKRPVGQKALYSTAMES  360
PIPK1γ_isoform_3    TLQRDCLVLESFKIMDYSLLLGVHNIDQHEREROAQGAQSTSDEKRPVGQKALYSTAMES  360
PIPK1γ_isoform_X2   TLQRDCLVLESFKIMDYSLLLGVHNIDQHEREROAQGAQSTSDEKRPVGQKALYSTAMES  360
                    ************************************************************

PIPK1γ_isoform_2    IQGGAARGEAIESDDTMGGIPAVNGRGERLLLHIGIIDILQSYRFIKKLEHTWKALVHDG  420
PIPK1γ_isoform_4    IQGGAARGEAIESDDTMGGIPAVNGRGERLLLHIGIIDILQSYRFIKKLEHTWKALVHDG  420
PIPK1γ_isoform_1    IQGGAARGEAIESDDTMGGIPAVNGRGERLLLHIGIIDILQSYRFIKKLEHTWKALVHDG  420
PIPK1γ_isoform_3    IQGGAARGEAIESDDTMGGIPAVNGRGERLLLHIGIIDILQSYRFIKKLEHTWKALVHDG  420
PIPK1γ_isoform_X2   IQGGAARGEAIESDDTMGGIPAVNGRGERLLLHIGIIDILQSYRFIKKLEHTWKALVHDG  420
                    ************************************************************

PIPK1γ_isoform_2    DTVSVHRPSFYAERFFKFMSNTVFRKNSSLKSSPSKKGRGGALLAVKPLGPTAAFSASQI  480
PIPK1γ_isoform_4    DTVSVHRPSFYAERFFKFMSNTVFRKNSSLKSSPSKKGRGGALLAVKPLGPTAAFSASQI  480
PIPK1γ_isoform_1    DTVSVHRPSFYAERFFKFMSNTVFRKNSSLKSSPSKKGRGGALLAVKPLGPTAAFSASQI  480
PIPK1γ_isoform_3    DTVSVHRPSFYAERFFKFMSNTVFRKNSSLKSSPSKKGRGGALLAVKPLGPTAAFSASQI  480
PIPK1γ_isoform_X2   DTVSVHRPSFYAERFFKFMSNTVFRKNSSLKSSPSKKGRGGALLAVKPLGPTAAFSASQI  480
                    ************************************************************

PIPK1γ_isoform_2    PSEREEAQYDLRGARSYPTLEDEGRPDLLPCTPPSFEEATTASIATTLSSTSLSIPERSP  540
PIPK1γ_isoform_4    PSEREEAQYDLRGARSYPTLEDEGRPDLLPCTPPSFEEATTASIATTLSSTSLSIPERSP  540
PIPK1γ_isoform_1    PSEREEAQYDLRGARSYPTLEDEGRPDLLPCTPPSFEEATTASIATTLSSTSLSIPERSP  540
PIPK1γ_isoform_3    PSEREEAQYDLRGARSYPTLEDEGRPDLLPCTPPSFEEATTASIATTLSSTSLSIPERSP  540
PIPK1γ_isoform_X2   PSEREEAQYDLRGARSYPTLEDEGRPDLLPCTPPSFEEATTASIATTLSSTSLSIPERSP  540
                    ************************************************************

PIPK1γ_isoform_2    SETSEQPRYRRRTQSSGQDGRPQEEPPAEEDLQQITVQVEPACSVEIVVPKEEDAGVEAS  600
PIPK1γ_isoform_4    SETSEQPRYRRRTQSSGQDGRPQEEPPAEEDLQQITVQVEPACSVEIVVPKEEDAGVEAS  600
PIPK1γ_isoform_1    SETSEQPRYRRRTQSSGQDGRPQEEPPAEEDLQQITVQVEPACSVEIVVPKEEDAGVEAS  600
PIPK1γ_isoform_3    SETSEQPRYRRRTQSSGQDGRPQEEPPAEEDLQQITVQVEPACSVEIVVPKEEDAGVEAS  600
PIPK1γ_isoform_X2   SETSEQPRYR--------------PQEEPPAEEDLQQITVQVEPACSVEIVVPKEEDAGVEAS  589
                    **********              ********************************
```

FIG. 9A

```
PIPK1y_isoform_2    PAGASAAVEVETASQASDEEGAPASQASDEEDAPATDIYFWRLNGPHAPTWPWRREGRAA  660
PIPK1y_isoform_4    PAGASAAVEVETASQASDEEGAPASQASDEEDAPATDIYF--------------------  640
PIPK1y_isoform_1    PAGASAAVEVETASQASDEEGAPASQASDEEDAPATDIYFP-----TDERSWVYS-----  650
PIPK1y_isoform_3    PAGASAAVEVETASQASDEEGAPASQASDEEDAPATDIYFFT-DGRYWIYSPRHRRLRAV  659
PIPK1y_isoform_X2   PAGASAAVEVETASQASDEEGAPASQASDEEDAPATDIYFFT-DGRYWIYSPRHRRLRAV  648
                    ****************************************

PIPK1y_isoform_2    CLCPY---PPBVVTPFPGTGLCASWSPOGTGGLGAMSCCVSVS----------  700
PIPK1y_isoform_4    --------------------------------------------------
PIPK1y_isoform_1    -------PLHYSAQAP----------PASDGESDT---------------  668
PIPK1y_isoform_3    TLSASGTVSDRSRPPWGEGAVPLGQQGAAGPRPEAQCLTSVVFQKGFG  707
PIPK1y_isoform_X2   TLSASGTVSDRSRPPWGEGAVPLGQQGAAGPRPEAQCLTSVVFQKGFG  696
```

FIG. 9B

```
PTPμ_isoform_1    MRGLGTCLATLAGLLLTAAGETFSGGCLFDEPYSTCGYSQSEGDDFNWEQVNTLTKPTSD   60
PTPμ_isoform_2    MRGLGTCLATLAGLLLTAAGETFSGGCLFDEPYSTCGYSQSEGDDFNWEQVNTLTKPTSD   60
                  ************************************************************

PTPμ_isoform_1    PWMFSGSFMLVNASGPEGQRAHLLLPQLKENDTRCIDFHYFVSSKSNSPPGLLNVYVEV   120
PTPμ_isoform_2    PWMFSGSFMLVNASGPEGQRAHLLLPQLKENDTRCIDFHYFVSSKSNSPPGLLNVYVEV   120
                  ***********************************************************

PTPμ_isoform_1    NNGPLGNPIWNISGDPTRTWNRAELAISTFWPNFYQVIFEVITSGHQGYLAIDEVKVLGR  180
PTPμ_isoform_2    NNGPLGNPIWNISGDPTRTWNRAELAISTFWPNFYQVIFEVITSGHQGYLAIDEVKVLGR  180
                  ************************************************************

PTPμ_isoform_1    PCTRTPHFLRIQNVEVNAGQFATFQCSAIGRTVAGDRLWLQGIDVRDAFLKEIKVTSSRR  240
PTPμ_isoform_2    PCTRTPHFLRIQNVEVNAGQFATFQCSAIGRTVAGDPLWLQGIDVPDAFLKEIKVTSSRR  240
                  ************************************ ******* ***************

PTPμ_isoform_1    FTASFNVVNTTKRDAGKYRCMIRTEGGVGISNYAELVVKEPPVIAPPQLASVGATYLWI  300
PTPμ_isoform_2    FTASFNVVNTTKRDAGKYRCMIRTEGGVGISNYAELVVKEPPVFIAPPQLASVGATYLWI  300
                  *******************************************

PTPμ_isoform_1    QLNANSINGDGPIVAREVEYCTASGSWNQFPVDSTSYKIGHLDPOTEYRISVLLTRPGE   360
PTPμ_isoform_2    QLNANSINGDGPIVAREVEYCTASGSWNDRQFVDSTSYKIGHLDPDTEYRISVLLTRPGE  360
                  ***************************   ***********************

PTPμ_isoform_1    GGTGSPGPALRTPTKCADPMRGPRKLEVVEVKSRQITIRWEPFGYNVTRCHSYNLTVRYC  420
PTPμ_isoform_2    GGTGSPGPALRTPTKCADPMRGPRKLEVVEVKSRQITIRWEPFGYNVTRCHSYNLTVRYC  420
                  ************************************************************

PTPμ_isoform_1    YQVGGQEQVREEVSWDTENSHPQHTITNLSPYTNVSVKLILMNPEGRKESQELIVQTDED  480
PTPμ_isoform_2    YQVGGQEQVREEVSWDTENSHPQHTITNLSPYTNVSVKLILMNPEGRKESQELIVQTDED  480
                  ************************************************************

PTPμ_isoform_1    LPGAVPTESIQGSTFEEKIFLQWREPTQTYGVITLYEITYKAVSSFDPEIDLSNQSGRVS  540
PTPμ_isoform_2    LPGAVPTESIQGSTFEEKIFLQWREPTQTYGVITLYEITYKAVSSFDPEIDLSNQSGRVS  540
                  ************************************************************

PTPμ_isoform_1    KLGNETHFLFFGLYPSITYSFTIRASTAKGFGPPATRQFTTKISAPSMPAYELETPLNQT  600
PTPμ_isoform_2    KLGNETHFLFFGLYPSITYSFTIPASTAKGFGPPATRQFTTKISAPSMPAYELETPLNQT  600
                  *********************** ************************************

PTPμ_isoform_1    DNTVTVMLRPAHSPGAPVSVYQIVVEEERPRRTKFTTEILKCYPVPIHFQNASLLNSQYY  660
PTPμ_isoform_2    QNTVTVMLKPAHSRGAPVSVYQIVVEEERPRRTKKTTEILKCYFVPIKFQNASLLNSQYY  660
                   ******* **** ********************  ******** ** *************

PTPμ_isoform_1    FAAEPFADSLQAAQFFTIGQNKTYNGYWNTPLLPYKSYPIYFQAASRANGETFIDCVQVA  720
PTPμ_isoform_2    FAAEPFADSLQAAQFFTIGQNKTYNGYWNTPLLPYKSYPIYFQAASRANGETFIDCVQVA  720
                  ************************************************************

PTPμ_isoform_1    TKGAATFKPVFEPEKQTDHTVKIAGVIAGILLFVIIFLGVVLVMKRKLAKKRKETMSST   780
PTPμ_isoform_2    TKGAATFKPVFEPEKQTDHTVKIAGVIAGILLFVIIFLGVVLVMKRKLAKKRKETMSST   780
                  ***********************************************************

PTPμ_isoform_1    RQEMTVMVNSMDKSIAEQGTNCDEAFSFMDTHNLNGPSVSSPSSFTMKTNTLSTSVPNSY  840
PTPμ_isoform_2    RQEMTVMVNSMDKSYAEQGTNCDEAFSFMDTHNLDGRSVSSPSSFTMKTNTLSTSVPNSY  840
                  ************** ******************* * *********************

PTPμ_isoform_1    YPDFFVPTAILVPINDETHTMASDTSSLVQSHTYKKREPADVPYQTGQLHPAIRVADLLQ  900
PTPμ_isoform_2    YPD-------------ETHTMASDTSSLVQSHTYKKREPADVPYQTGQLHPAIRVADLLQ  887
                  ***             ********************************************

PTPμ_isoform_1    HITQMKCAEGYGFKEEYESFFEGQSAPWDSAKKDENRMKNRYGNIIAYDHSRVRLQTIEG  960
PTPμ_isoform_2    HITQMKCAEGYGFKEEYESFFEGQSAPWDSAKKDENRMKNRYGNIIAYDHSRVRLQTIEG  947
                  ************************************************************

PTPμ_isoform_1    DTNSDYINGNYIDGYHRPNHYIATQGPMQETIYDFWRMVWHENTASIIMVTNLVEVGRVK 1020
PTPμ_isoform_2    DTNSDYINGNYIDGYHRPNHYIATQGPMQETIYDFWRMVWHENTASIIMVTNLVEVGRVK 1007
                  ************************************************************

PTPμ_isoform_1    CCKYWPDDTEIYKDIKVTLIETELLAEYVIRTFAVEKRGVHEIREIRQFHFTGWPDHGVP 1080
PTPμ_isoform_2    CCKYWPDDTEIYKDIKVTLIETELLAEYVIRTFAVEKRGVHEIREIRQFHFTGWPDHGVP 1067
                  ************************************************************
```

FIG. 10A

```
PTPµ_isoform_1    YHATGLLGFVRQVKSKSPPSAGPLVVHCSAGAGRTGCFIVIDIMLDMAEREGVVDIYNCV    1140
PTPµ_isoform_2    YHATGLLGFVRQVKSKSPPSAGPLVVHCSAGAGRTGCFIVIDIMLDMAEREGVVDIYNCV    1127
                  ************************************************************

PTPµ_isoform_1    RELRSRRVNMVQTEEQYVFIHDAILEACLCGDTSVPASQVRSLYYDMNKLDPQTNSSQIK    1200
PTPµ_isoform_2    RELRSRRVNMVQTEEQYVFIHDAILEACLCGDTSVPASQVRSLYYDMNKLDPQTNSSQIK    1187
                  ************************************************************

PTPµ_isoform_1    EEFRTLNMVTPTLRVEDCSIALLPRNHEKNPCMDILPPDRCLPFLITIDGESSNYINAAL    1260
PTPµ_isoform_2    EEFRTLNMVTPTLRVEDCSIALLPRNHEKNPCMDILPPDRCLPFLITIDGESSNYINAAL    1247
                  ************************************************************

PTPµ_isoform_1    MDSYKQPSAFIVTQHPLPNTVKDFWRLVLDYHCTSVVMLNDVDPAQLCPQYWPENGVHRH    1320
PTPµ_isoform_2    MDSYKQPSAFIVTQHPLPNTVKDFWRLVLDYHCTSVVMLNDVDPAQLCPQYWPENGVHRH    1307
                  ************************************************************

PTPµ_isoform_1    GPIQVEFVSADLEEDIISRIFRIYNAARPQDGYRMVQQFQFLGWPMYRDTPVSKRSFLKL    1380
PTPµ_isoform_2    GPIQVEFVSADLEEDIISRIFRIYNAARPQDGYRMVQQFQFLGWPMYRDTPVSKRSFLKL    1367
                  ************************************************************

PTPµ_isoform_1    IRQVDKWQEEYNGGEGRTVVHCLNGGGRSGTFCAISIVCEMLRHQRTVDVFHAVKTLRNN    1440
PTPµ_isoform_2    IRQVDKWQEEYNGGEGRTVVHCLNGGGRSGTFCAISIVCEMLRHQRTVDVFHAVKTLRNN    1427
                  ************************************************************

PTPµ_isoform_1    KPNMVDLLDQYKFCYEVALEYLNSG    1465
PTPµ_isoform_2    KPNMVDLLDQYKFCYEVALEYLNSG    1452
                  *************************
```

FIG. 10B

COMPOSITION COMPRISING A CELL SAMPLE FROM A SUBJECT WITH SCOLIOSIS AND A REAGENT FOR DETECTING PTPµ OR PIPK1Y

CROSS REFERENCE TO RELATED APPLICATIONS

The present application is a National Phase Entry under 35 U.S.C. § 371 of International Application No. PCT/CA2014/050568* filed on Jun. 17, 2014 and published in English, which claims the benefit of U.S. provisional application Ser. No. 61/835,698, filed on Jun. 17, 2013, the disclosures of which are hereby incorporated herein by reference.

STATEMENT REGARDING FEDERALLY SPONSORED RESEARCH OR DEVELOPMENT

N.A.

FIELD OF THE INVENTION

The present invention relates to markers of scoliosis and scoliosis progression. More particularly, it relates to new markers for progression of idiopathic scoliosis and uses thereof to stratify scoliotic patients and predict the risk of developing scoliosis.

REFERENCE TO SEQUENCE LISTING

This application contains a Sequence Listing in computer readable form entitled 14033_124_ST25, created Jun. 17, 2014 having a size of 95 kilobytes, which is incorporated herein by reference.

BACKGROUND OF THE INVENTION

Idiopathic Scoliosis is a spine deformity of unknown cause generally defined as a lateral curvature greater than 10 degrees accompanied by a vertebral rotation [1]. Adolescent Idiopathic Scoliosis (AIS) is one of the most frequent childhood deformities worldwide, characterized by a 3D spinal deformity with unknown cause, and represents both an immediate medical challenge and a chronic condition affecting individuals throughout their lives. It is the most common orthopedic condition requiring surgery in adolescents and affects 4% of this population. This condition is most commonly diagnosed between the ages of 9 to 13 years [2,3,4]. The diagnosis is primarily of exclusion and is made only after ruling out other causes of spinal deformity such as vertebral malformation, neuromuscular or syndromic disorders. Traditionally, the trunkal asymmetry is revealed by Adams forward bending test and measured with scoliometer during physical examination. The diagnosis can then be confirmed by radiographic observation of the curve and the angle measurement using the Cobb method.

Once diagnosed, the primary concern for physicians in managing scoliotic children is whether the curve will progress. Indeed, the curve progression is often unpredictable and is more frequently observed among girls than in boys. If untreated, the curve can progress dramatically, creating significant physical deformity and even cardiopulmonary problems. These manifestations become life threatening when the curve exceeds 70 degrees. The current treatment options to prevent or stop curve progression include bracing and surgery. In general, bracing is recommended for curves between 25 and 40 degrees, while surgery is reserved for curve greater than 45 degrees or curves that are unresponsive to bracing. Today in the United States there are approximately one million children between ages 10 and 16 with some degree of IS. Approximately, 10% of children diagnosed with idiopathic scoliosis have curve progression requiring corrective surgery. About 29,000 scoliosis surgeries are done every year in North America, resulting in significant psychological and physical morbidity. (Goldberg M S, Mayo N E, Poitras B et al. The Ste-Justine Adolescent Idiopathic Scoliosis Cohort Study. Part I: Description of the study. *Spine* 1994; 19:1551-61; Poitras B, Mayo N E, Goldberg M S et al. The Ste-Justine Adolescent Idiopathic Scoliosis Cohort Study. Part IV: Surgical correction and back pain. *Spine* 1994; 19:1582-8).

Currently, there is no proven method or test available to identify subjects at risk of developing IS to predict which affected individuals require treatment to prevent or stop progression of the disease so that appropriate treatment can be early provided and prevent surgical complications and cardiac and/or respiratory problems. (Weinstein S L, Dolan L A, Cheng J C et al. Adolescent idiopathic scoliosis. *Lancet* 2008; 371:1527-37).

Therefore, the application of current treatments, such as bracing or surgical correction, is delayed until a significant deformity is detected or until a significant progression is clearly demonstrated, resulting in a delayed, less than optimal treatment and often important psychological sequels (Society S R. Morbidity & Mortality Committee annual Report 1997).

Currently, in order to detect the deformity, diagnosed children are subjected to multiple radiographs over several years, usually until they reach skeletal maturity. It is estimated that the typical patients with scoliosis wil have approximately 22 radiological examinations over a 3-year period. There are potential risks in multiple radiographic examinations. For this reason also, alternative approaches that could allow performing the prognosis of idiopathic scoliosis are strongly desirable.

The major limitation in developing prognostic tests that could facilitate treatment choices for patients is the heterogeneous nature of AIS. At the clinical level, the heterogeneity of AIS is clearly illustrated by the variability of curve patterns, localisations and curve magnitude even in families with multiple affected members.

In absence of reliable AIS phenotypes, there is a need to understand better the molecular changes associated with disease onset and spinal deformity progression. Molecular definition of disease is rapidly replacing traditional pathology-based disease descriptions in part because of its utility in identifying the optimal treatment regimen for patients.

To this effect, the existence of a differential melatonin signaling dysfunction was reported among AIS patients leading to their stratification into three functional groups or biological endophenotypes (Moreau et al., 2004); (Azeddine et al., 2007); (Letelier et al., 2008) and WO2003/073102 to Moreau. More particularly, AIS patients were stratified into three functional groups (FG1, FG2 and FG3) representing distinct biological endophenotypes. According to this stratification, the scoliotic patients and children more at risk of developing scoliosis are less responsive to Gi protein stimulation when compared with healthy control subjects, and the stratification is based on the percentage of degree of reduction relative to control group. The classification ranges were fixed between 10 and 40% for FG3, 40 and 60% for FG2 and 60 and 90% for FG1.

More recently, using the cellular dielectric spectrometry (CDS) technique, which is a label-free method for the functional evaluation of G proteins and endogenous receptors coupled to those proteins (Verdonk et al., 2006), it was found that the cellular response following melatonin receptor stimulation by melatonin was mainly Gi-dependent in normal osteoblasts and was reduced to different extents in osteoblasts derived from AIS patients (Akoume et al., 2010). Approximately 33% of asymptomatic children diagnosed with a defective Gi protein function have developed scoliosis many years later (Akoume et al., 2010).

Early detection/prognosis of scoliosis is not only critical to successful and less invasive clinical outcomes but broadens the range of treatment options for clinicians. Indeed, improving patients' stratification and disease staging represent key steps to select AIS patients for minimally invasive surgeries before their spinal deformity is too advanced. OPN, a multifunctional cytokine, has been identified as a potentially key pathophysiologic contributor in the development of idiopathic scoliosis. Particularly, increased plasma OPN levels in patients with idiopathic scoliosis and in bipedal mice, a well-established animal model of this disease, were correlated with the disease (see WO 2008/119170 to Moreau).

It is commonly accepted that the development of scoliosis is influenced by a postural mechanism. The bipedal condition, naturally present in humans or experimentally induced in animals seems to play an important role in the manifestation of scoliotic deformities (Machida et al., 1999). Importantly, it has been reported that mice on a C57Bl/6 or C3HHe background develop scoliosis closely similar to human idiopathic scoliosis when they gain bipedal posture for 40 weeks following amputation of their forelimbs and tails (Machida et al., 2006); (Oyama et al., 2006).

The present description refers to a number of documents, the content of which is herein incorporated by reference in their entirety.

SUMMARY OF THE INVENTION

The present invention provides evidence that lack of protein tyrosine phosphatase μ (PTPμ) under high plasma OPN conditions can exacerbate spinal deformity progression without influencing circulating OPN level or OPN receptors levels. Indeed, data presented herein reveal that bipedal PTPμ$^{-/-}$ mice (deleted of gene Receptor-type tyrosine-protein phosphatase mu (PTPRM) encoding PTPμ) display greater incidence of scoliosis and exhibit more pronounced lateral curvature than bipedal WT mice. More particularly, the PTPμ deficiency leads to the amplification of the inhibitory effect of OPN on GiPCR signaling. In addition, results presented herein identify dysregulation of phosphatidylinositol(4) phosphate 5 kinase type 1 gamma (PIPK1γ), a PTPμ substrate, due to the loss of PTPμ as a unique mechanism underlying development of severe lateral curvature under high plasma OPN conditions: lack of PTPμ favours the interaction of OPN with integrin via PIPK1γ action.

The association of integrins with theirs ligands can be regulated by the tyrosine phosphorylation of PIPK1γ upon focal adhesion kinase (FAK)-dependent C sarcoma tyrosine kinase (Src) activation[12, 13] and PIPK1γ is dephosphorylated by PTPμ[14]. It is shown herein that increased tyrosine phosphorylated PIPK1γ is observed in osteoblasts from PTPμ$^{-/-}$ mice, and that this increased phosphorylation is attenuated by the inhibition of FAK and Src with pharmacological inhibitors. Thus, data presented herein demonstrates that PIPK1γ contributes to the increased reduction of GiPCR signaling observed in the absence of PTPμ. This is further supported by the observation that silencing of PIPK1γ by siRNA abrogated the difference in the degree of response between WT and PTPμ$^{-/-}$ osteoblasts. Collectively, these results suggest, without being limited by this hypothesis, that loss of PTPμ causes a dysregulation of PIPK1γ activity, which in turn leads to the amplification of the inhibitory effect of OPN on GiPCR signaling and the subsequent severe lateral curvature.

Osteoblasts from PTPμ$^{-/-}$ mice were shown to be more sensitive to the inhibitory effect of OPN on GiPCR signaling. This finding together with the fact that PTPμ$^{-/-}$ mice exhibit more severe lateral curvature, support the notion that repression of GiPCR signaling is an important event in biological process driving the development of scoliosis and indicate that decrease of PTPμ protein contributes to changes in the pathobiology of scoliosis and plays an important role in severe progression of scoliosis in bipedal mice.

The present application also shows that the scoliotic human patients examined exhibit lower levels of PTPμ protein and higher levels of PIPK1γ protein than control individuals.

Accordingly, in an aspect of the present invention, there is provided a method of stratifying a subject having adolescent idiopathic scoliosis (AIS) comprising: (i) providing a cell sample isolated from the subject; and (i) (a) detecting PTPμ expression or activity in the cell sample; (b) detecting tyrosine phosphorylated PIPK1γ expression or activity in the cell sample; (c) detecting total PIPK1γ expression or activity in the cell sample; or (d) any combination of at least two of (a) to (c); whereby the results of the detecting step enables the stratification of the subject having AIS as belonging to an AIS subclass.

According to another aspect of the present invention, there is provided a method for predicting the risk of developing a scoliosis comprising: (i) providing a cell sample isolated from the subject; and (ii) (a) detecting PTPμ expression or activity in the cell sample; (b) detecting tyrosine phosphorylated PIPK1γ expression or activity in the cell sample; (c) detecting total PIPK1γ expression or activity in the cell sample; or (d) any combination of at least two of (a) to (c); wherein PTPμ expression or activity that is lower in the cell sample from the subject than in a control sample and/or a tyrosine phosphorylated PIPK1γ expression or activity that is higher in the cell sample from the subject than in a control sample and/or a total PIPK1γ expression or activity that is higher in the cell sample from the subject than in a control sample is indicative that the subject is at risk for developing AIS.

In an embodiment, said scoliosis is an idiopathic scoliosis. In another embodiment, said idiopathic scoliosis is adolescent idiopathic scoliosis (AIS). In another embodiment, the subject is a likely candidate for developing adolescent idiopathic scoliosis. In another embodiment, the subject is pre-diagnosed as having an idiopathic scoliosis, and the risk for developing the idiopathic scoliosis is a risk for developing a more severe idiopathic scoliosis. In another embodiment, said cell sample comprises osteoblasts, myoblasts or peripheral blood mononuclear cells (PBMC). In another embodiment, said cell sample comprises PBMCs. In another embodiment, said cell sample comprises lymphocytes.

According to another aspect of the present invention, there is provided a method of increasing GiPCR signaling in cells of a subject in need thereof (e.g., scoliotic subject) comprising administering to the subject's cells an effective amount of (a) an inhibitor of PIPK1γ tyrosine phosphorylation; (b) an activator of PIPK1γ tyrosine dephosphorylation; (c) an inhibitor of PIPK1γ expression and/or activity; (d) or any combination of (a) to (c), whereby the GiPCR signaling is increased in the subject's cells.

According to another aspect of the present invention, there is provided a use comprising an effective amount of (a) an inhibitor of PIPK1γ tyrosine phosphorylation; (b) an activator of PIPK1γ tyrosine dephosphorylation; (c) an inhibitor of PIPK1γ expression and/or activity; (d) or any combination of (a) to (c), for increasing GiPCR signaling in cells of a subject in need thereof (e.g., scoliotic subject) or for preparing a medicament for increasing GiPCR signaling in cells of a subject in need thereof (e.g., scoliotic subject).

In an embodiment, the inhibitor of PIPK1γ tyrosine phosphorylation is a C-sarcoma tyrosine kinase (Src) inhibitor. In another embodiment, the Src inhibitor is PP2. In another embodiment, the inhibitor of PIPK1γ tyrosine phosphorylation is a focal adhesion kinase (Fak) inhibitor. In another embodiment, the Fak inhibitor is FAK inhibitor-14 (1,2,4,5-Benzenetetramine tetrahydrochloride). In another embodiment, the activator of PIPK1γ tyrosine dephosphorylation is PTPμ or an activator of PTPμ expression and/or activity. In another embodiment, the inhibitor of PIPK1γ expression is a PIPK1γ siRNA. In another embodiment, the subject in need thereof is a subject diagnosed with a scoliosis. In another embodiment, the subject in need thereof is likely to develop a scoliosis. In another embodiment, the scoliosis is adolescent idiopathic scoliosis. In another embodiment, the method is in vitro.

According to another aspect of the present invention, there is provided a method of selecting an agent as a potential candidate for the reduction or prevention of scoliosis comprising contacting a candidate agent with a cell expressing (i) PTPμ; and/or (i) PIPK1γ, and detecting the expression and/or activity of PTPμ or PIPK1γ, wherein (a) when the expression and/or activity of PTPμ is higher in the presence of the candidate agent as compared to in the absence thereof; and/or (b) when the expression and/or activity of PIPK1γ is lower in the presence of the candidate agent as compared to in the absence thereof, the candidate agent is selected.

In an embodiment, when the expression of PIPK1γ is lower in the presence of the candidate agent as compared to in the absence thereof, the candidate agent is selected.

According to another aspect of the present invention, there is provided a kit for stratifying and or predicting the risk for predicting the risk for developing a scoliosis, comprising (a) a ligand for detecting PTPμ expression or activity in the cell sample; (b) a ligand for detecting tyrosine phosphorylated PIPK1γ expression or activity in the cell sample; and/or (c) a ligand for detecting total PIPK1γ expression or activity in the cell sample.

According to another aspect of the present invention, there is provided a kit for increasing GiPCR signaling in cells of a subject in need thereof (e.g., scoliotic subject) comprising (a) an inhibitor of PIPK1γ tyrosine phosphorylation; (b) an activator of PIPK1γ tyrosine dephosphorylation; (c) an inhibitor of PIPK1γ expression and/or activity; (d) or any combination of (a) to (c). In specific embodiments, the kit of the present invention further comprises a carrier. In a specific embodiment, the kit further comprises one or more containers for the one or more ligands inhibitors and/or activators. The kit may additionally comprise instructions to use the kit for i) for stratifying a subject having AIS ii) predicting the risk of developing a scoliosis and/or ii) for increasing GiPCR signaling in cells of a subject in need thereof.

According to another aspect of the present invention, there is provided a composition (e.g., for increasing GiPCR signaling in cells of a subject in need thereof (e.g., scoliotic subject)) comprising (a) an inhibitor of PIPK1γ tyrosine phosphorylation; (b) an activator of PIPK1γ tyrosine dephosphorylation; (c) an inhibitor of PIPK1γ expression and/or activity; (d) or any combination of (a) to (c). In specific embodiments, the composition further comprises a pharmaceutically acceptable carrier.

According to another aspect of the present invention, there is provided a method of stratifying a subject having or at risk of developing scoliosis, said method comprising: (i) providing a cell sample isolated from the subject; (i) (a) detecting PTPμ expression and/or activity in the cell sample; (b) detecting PIPK1γ expression and/or activity in the cell sample; or (c) a combination of (a) and (b); and (ii) stratifying said subject into a AIS subclass based on the level of expression or activity of PTPμ and/or PIPK1γ in the cell sample of the subject.

In a specific embodiment, step (ii) further comprises stratifying said subject as belonging to: (1) a first subclass characterized by: (a) a decreased level of PTPμ protein as compared to a level in a control; (b) a decreased phosphatase activity of PTPμ protein as compared to a level in a control; (c) an increased level of PIPK1γ protein as compared to a level in a control; (d) an increased PIPK1γ protein kinase activity as compared to a level in a control; or (e) any combination of at least two of (a) to (d); or (2) a second subclass characterized by: (a) an equal or increased level of PTPμ protein as compared to a level in a control; (b) an equal or increased phosphatase activity of PTPμ protein as compared to a level in a control; (c) an equal or decreased level of PIPK1γ protein as compared to a level in a control; (d) an equal or decreased PIPK1γ protein kinase activity as compared to a level in a control; or (e) any combination of at least two of (a) to (d).

According to another aspect of the present invention, there is provided a method for predicting the risk of developing a scoliosis in a subject comprising: (i) providing a cell sample isolated from the subject; (i) (a) detecting PTPμ expression and/or activity in the cell sample; (b) detecting PIPK1γ expression and/or activity in the cell sample; or (c) a combination of (a) and (b); and (iii) determining that the subject is at risk of developing a scoliosis when: (a) PTPμ expression and/or activity is decreased; and/or (b) PIPK1γ expression and/or activity is increased; in the subject's sample as compared to a level in a control sample.

In a specific embodiment, step (i) of determining that the subject is at risk of developing a scoliosis is when: (a) PTPμ protein level is decreased; (b) PTPμ protein phosphatase activity is decreased; (c) PIPK1γ protein level is increased; (d) PIPK1γ protein kinase activity is increased; or (e) any combination of at least two of (a) to (d), in the subject's sample as compared to a level in a control sample. In another specific embodiment, wherein the PIPK1γ protein level in step (ii) is tyrosine phosphorylated PIPK1γ protein. In another specific embodiment, detecting PIPK1γ expression and/or activity in step (i) (b) comprises detecting the level of tyrosine phosphorylated PIPK1γ protein in the sample. In another specific embodiment, said scoliosis is an idiopathic scoliosis. In another specific embodiment, said scoliosis is adolescent idiopathic scoliosis (AIS). In another specific embodiment, the subject is at risk of developing adolescent idiopathic scoliosis. In another specific embodiment, the subject is pre-diagnosed as having an idiopathic scoliosis, and the risk for developing the idiopathic scoliosis is a risk for developing a more severe idiopathic scoliosis. In another specific embodiment, the subject is pre-diagnosed as having adolescent idiopathic scoliosis (AIS), and the risk of developing AIS is a risk of developing a more severe AIS. In another specific embodiment, said cell sample comprises osteoblasts, myoblasts or peripheral blood mononuclear cells (PBMC). In another specific embodiment, said cell sample comprises PBMCs. In another specific embodiment, said PBMCs comprises lymphocytes.

According to another aspect of the present invention, there is provided a method of increasing GiPCR signaling in cells of a subject in need thereof comprising administering to the subject's cells an effective amount of (a) an inhibitor of PIPK1γ tyrosine phosphorylation; (b) an activator of PIPK1γ tyrosine dephosphorylation; (c) an inhibitor of PIPK1γ expression and/or activity; or (d) any combination of (a) to (c), whereby the GiPCR signaling is increased in the subject's cells.

In a specific embodiment, the inhibitor of PIPK1γ tyrosine phosphorylation is a C-sarcoma tyrosine kinase (Src) inhibitor. In another specific embodiment, the Src inhibitor is PP2. In another specific embodiment, the inhibitor of PIPK1γ tyrosine phosphorylation is a focal adhesion kinase (Fak) inhibitor. In another specific embodiment, the Fak inhibitor is FAK inhibitor-14 (1,2,4,5-Benzenetetramine tetrahydrochloride). In another specific embodiment, the activator of PIPK1γ tyrosine dephosphorylation is PTPµ or an activator of PTPµ expression and/or activity. In another specific embodiment, the inhibitor of PIPK1γ expression is a siRNA PIPK1γ. In another specific embodiment, the subject in need thereof is a subject diagnosed with a scoliosis. In another specific embodiment, the subject in need thereof is likely to develop a scoliosis. In another specific embodiment, the scoliosis is adolescent idiopathic scoliosis. In another specific embodiment, the method is in vitro.

According to another aspect of the present invention, there is provided a method of selecting an agent as a potential candidate for the reduction or prevention of scoliosis, comprising contacting a candidate agent with a cell expressing (i) PTPµ; and/or (i) PIPK1γ, and detecting the expression and/or activity of (i) PTPµ and/or (i) PIPK1γ, wherein (a) when the expression and/or activity of PTPµ is higher in the presence of the candidate agent as compared to in the absence thereof; and/or (b) when the expression and/or activity of PIPK1γ is lower in the presence of the candidate agent as compared to in the absence thereof, the candidate agent is selected.

According to another aspect of the present invention, there is provided a method of selecting an agent as a potential candidate for increasing GiPCR signaling in a cell, comprising contacting a candidate agent with a cell expressing (i) PTPµ; and/or (i) PIPK1γ, and detecting the expression and/or activity of (i) PTPµ and/or (ii) PIPK1γ, wherein (a) when the expression and/or activity of PTPµ is higher in the presence of the candidate agent as compared to in the absence thereof; and/or (b) when the expression and/or activity of PIPK1γ is lower in the presence of the candidate agent as compared to in the absence thereof, the candidate agent is selected.

In a specific embodiment, when the expression of PIPK1γ is lower in the presence of the candidate agent as compared to in the absence thereof, the candidate agent is selected. detecting the expression of PIPK1γ comprises detecting the level of tyrosine phosphorylated PIPK1γ protein in the sample.

Other objects, advantages and features of the present invention will become more apparent upon reading of the following non-restrictive description of specific embodiments thereof, given by way of example only with reference to the accompanying drawings.

BRIEF DESCRIPTION OF THE DRAWINGS

In the appended drawings:

FIGS. 1A-D shows that the lack of PTPµ influences the nature of scoliosis associated with high plasma OPN level in bipedal mice. (FIG. 1A) Plasma OPN was measured in 60 C57Bl/6j Wild type (WT) and 60 PTPµ-/- mice each 12 weeks during the experimental period. Average OPN levels are represented for each group. No difference was detected at all time points in the plasma OPN levels of WT and PTPµ$^{-/-}$ mice. The higher values of OPN were notified at the 36th postoperative (removal of forelimbs) week in both genotypes. (FIG. 1B) The 60 WT and 60 PTPµ-/- mice were examined by radiography. FIGS. 1C and D show representative radiographs of mice of the wild type (FIG. 1C) and PTPµ-/- (FIG. 1D) mice cohorts. It may be observed that the scoliosis of the PTPµ-/- representative mouse is more severe than that of the wild type mouse. The PTPµ$^{-/-}$ mice showed increase in the incidence (FIG.1B) and severity (FIG. 1D) of scoliosis comparing to wild type mice.

FIGS. 2A-L shows the specificity of the agonists to GiPCR signaling. The pre-treatment of osteoblasts from bipedal WT and PTPµ$^{-/-}$ mice with pertussis toxin (PTX) blocked the Gi coupling of each of three tested compounds to their cognate receptors in these cells, namely oxymethazolin (α2 adrenergic receptor (α2-ADR)), somatostatin (somatostatin receptor (SSTR)); and apelin-17 (Apelin receptor (APJR)). FIGS. 2A to C show the response of the C57Bl/6j Wild type (WT) cells treated with vehicle; FIGS 2D to F show the response of the C57Bl/6j Wild type (WT) cells treated with PTX; FIGS. 2G to I show the response of the C57Bl/6j (PTPµ$^{-/-}$) cells treated with vehicle; and FIGS. 2J to L show the response of the C57Bl/6j (PTPµ$^{-/-}$) cells treated with PTX. These results indicate that these compounds provoked typical cellular dielectric spectroscopy (CDS) response profiles of GiPCR (i.e., GiPCR signaling) in WT and PTPµ$^{-/-}$ osteoblasts. Panels A to L present raw results as observed on CellKey™.

FIGS. 3A to C, show that osteoblasts from bipedal PTPµ$^{-/-}$ mice were less responsive than those from bipedal WT mice to apelin-17 (APJR), oxymethazoin (α2-ADR) and somatostatin (SSTR). Different concentrations for each agonist were used leading to increased response in a concentration-dependent manner in osteoblasts from WT and PTPµ$^{-/-}$ mice. For FIGS. 3D and E, OPN was knockdown in WT and PTPµ$^{-/-}$ osteoblasts cells and knockdown efficiency was determined by qPCR (FIG. 3D) and Western blot (FIG. 3E). FIGS. 3F to H show that the lack of PTPµ exacerbates the inhibitory effect of OPN on GiPCR signaling using the same three agonists which mentioned above.

FIGS. 4A to C present results obtained with osteoblasts from WT and PTPµ$^{-/-}$ treated with varying concentrations of exogenous recombinant OPN (rOPN) prior to GiPCR stimulation with different concentrations of the agonists identified.

In FIGS. 5A and B, the expression of OPN receptors was determined in WT and PTPµ$^{-/-}$ osteoblasts using qPCR and Western blot, respectively. In FIG. 5C, osteoblasts cell lysates of WT and PTPµ$^{-/-}$ were immunoprecipitated with antibodies against specific OPN receptors subunits (i.e., $\beta_1$, $\beta_3$, $\beta_5$, $\beta_8$, $\alpha_1$, $\alpha_4$, $\alpha_5$, $\alpha_v$, and CD44) followed by western blot specific for OPN. Results in panel C show that lack of PTPµ increases OPN's interaction with integrins but not CD44.

In FIG. 6A, osteoblasts from PTPµ$^{-/-}$ mice, were treated with inhibitors of Src (PP2) and FAK (inhibitor-14), which are known to prevent phosphorylation, prior to immunoprecipitation assay. While phosphorylation levels of PIPK1γ were attenuated by both treatments, they were higher in osteoblasts from PTPµ$^{-/-}$ than those from WT mice. P-tyr: tyrosine phosphorylated PIPK1γ; PIPK1: PIPK1γ total form. In FIGS.6B and C, PIPK1γ was knockdown using siRNA approach in WT and PTPµ$^{-/-}$ osteoblasts cells as shown by the qPCR and Western blot, respectively. FIGS. 6D to H show the response to somatostatin stimulation in WT and PTPµ osteoblasts in which, PIPK1γ was knockdown. Osteoblasts depleted of PIPK1γ exhibited similar degree of response to somatostatin stimulation than WT osteoblasts.

FIGS. 9A and B show a multiple sequence alignment between the amino acid sequences of PIPK1γ isoforms 1 to 4 and X2 ( PIPK1γ isoform 1 (SEQ ID NO: 28), PIPK1γ isoform 2 (SEQ ID NO: 3), PIPK1γ isoform 3 (SEQ ID NO:32), PIPK1γ isoform 4 (SEQ ID NO: 33) and PIPK1γ isoform X2 (SEQ ID NO: 35).

FIGS. 10A and B show a multiple sequence alignment between the amino acid sequences of PTPµ isoforms 1 (SEQ ID NO: 37) and 2(SEQ ID NO: 39).

DESCRIPTION OF ILLUSTRATIVE EMBODIMENTS

Figure 2A:
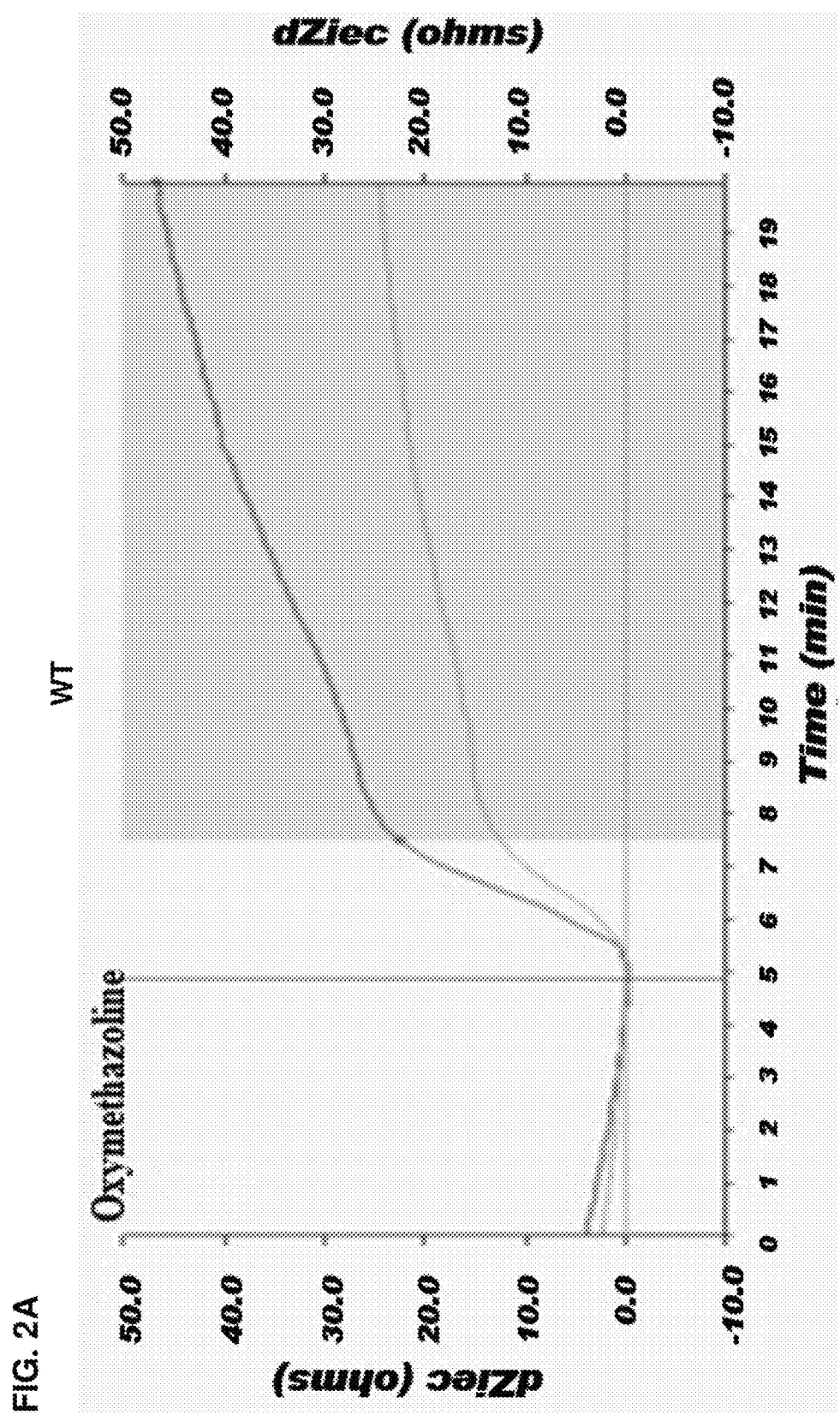
Figure 2B:
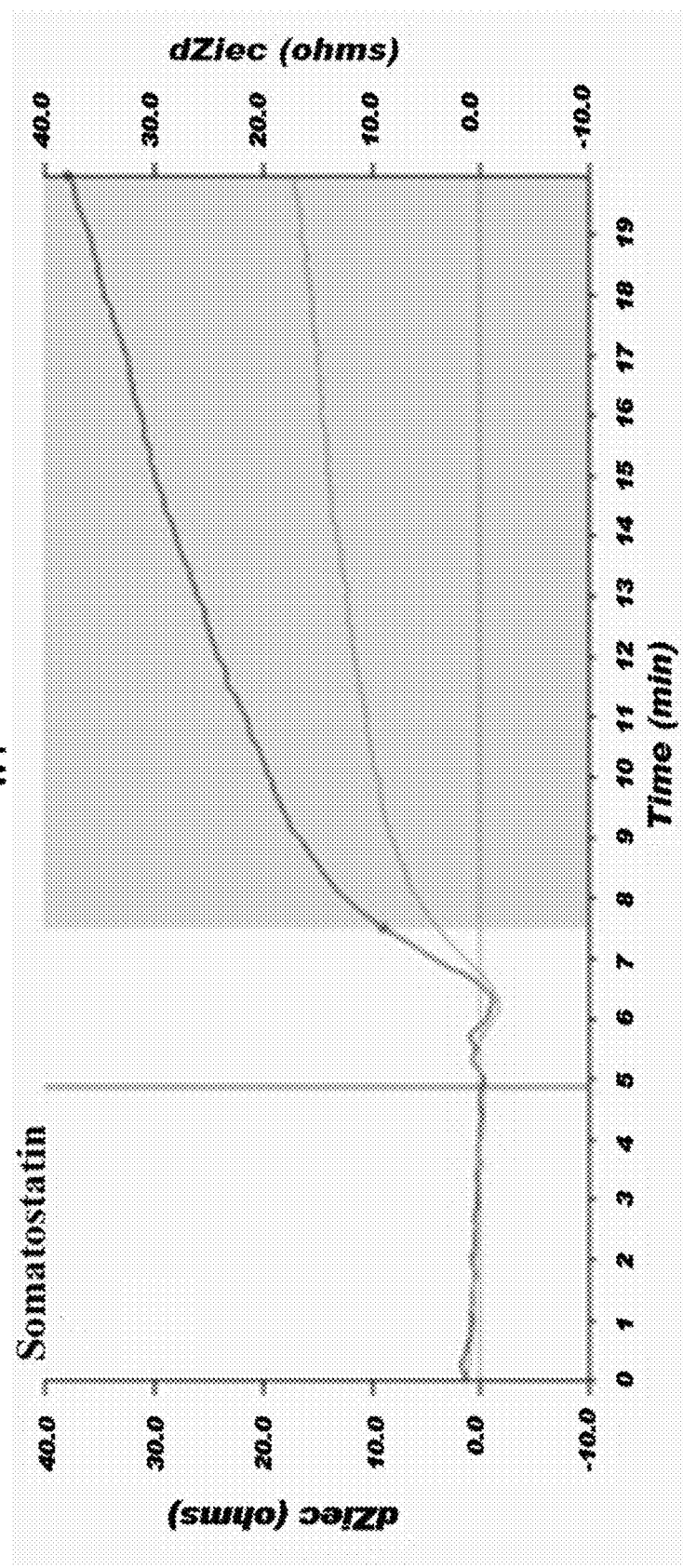
Figure 2C:
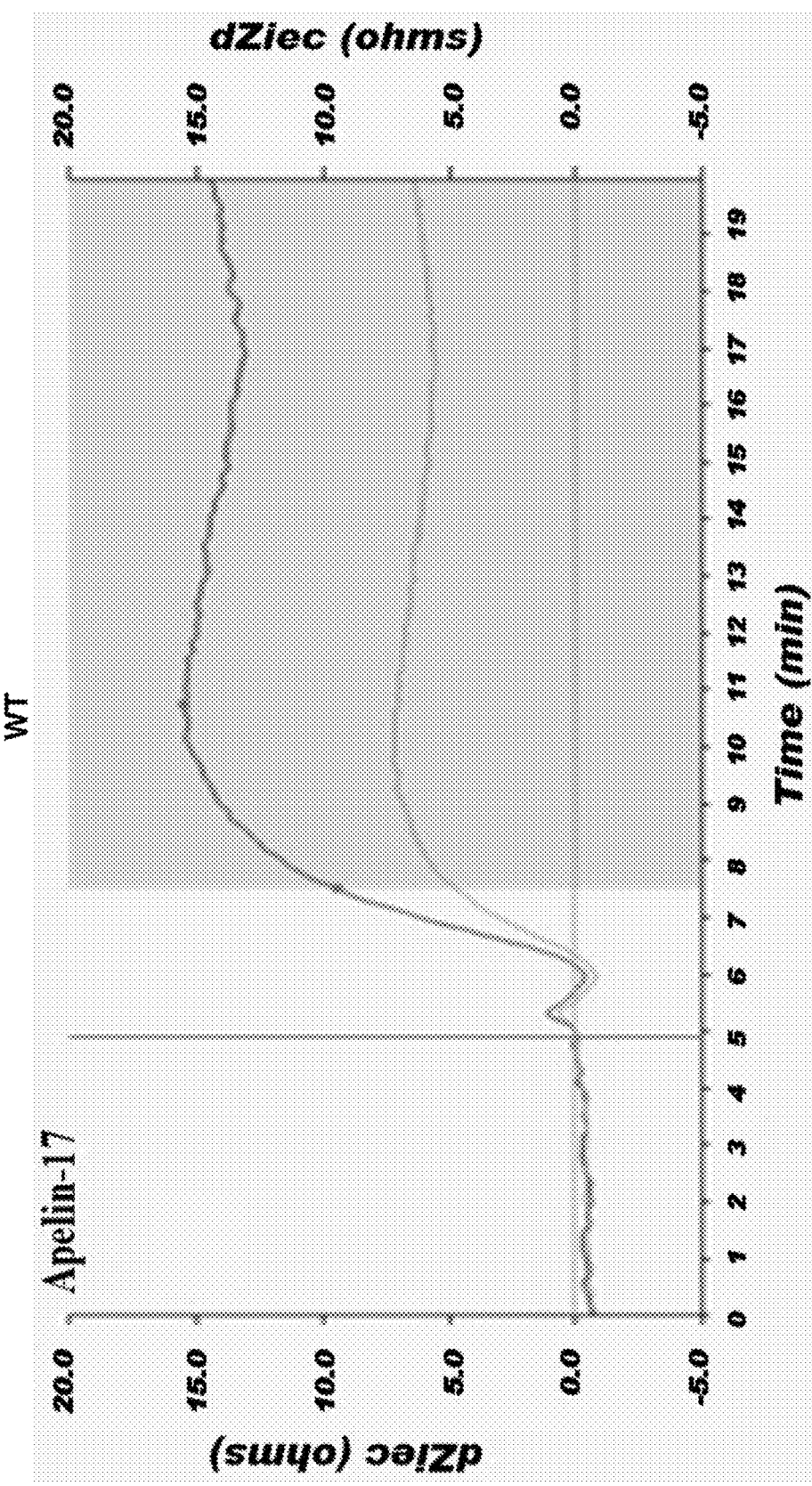
Figure 2D:
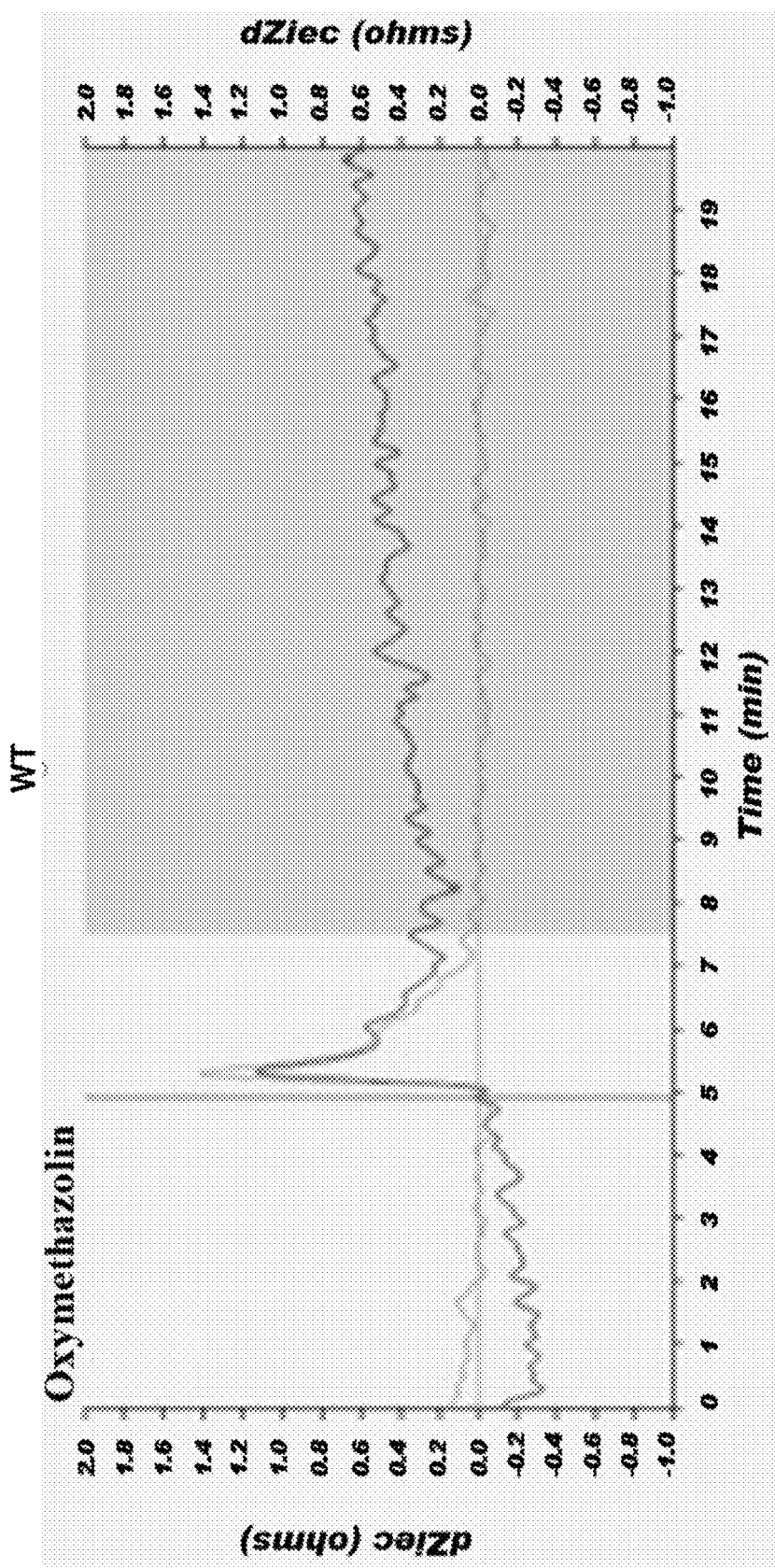
Figure 2E:
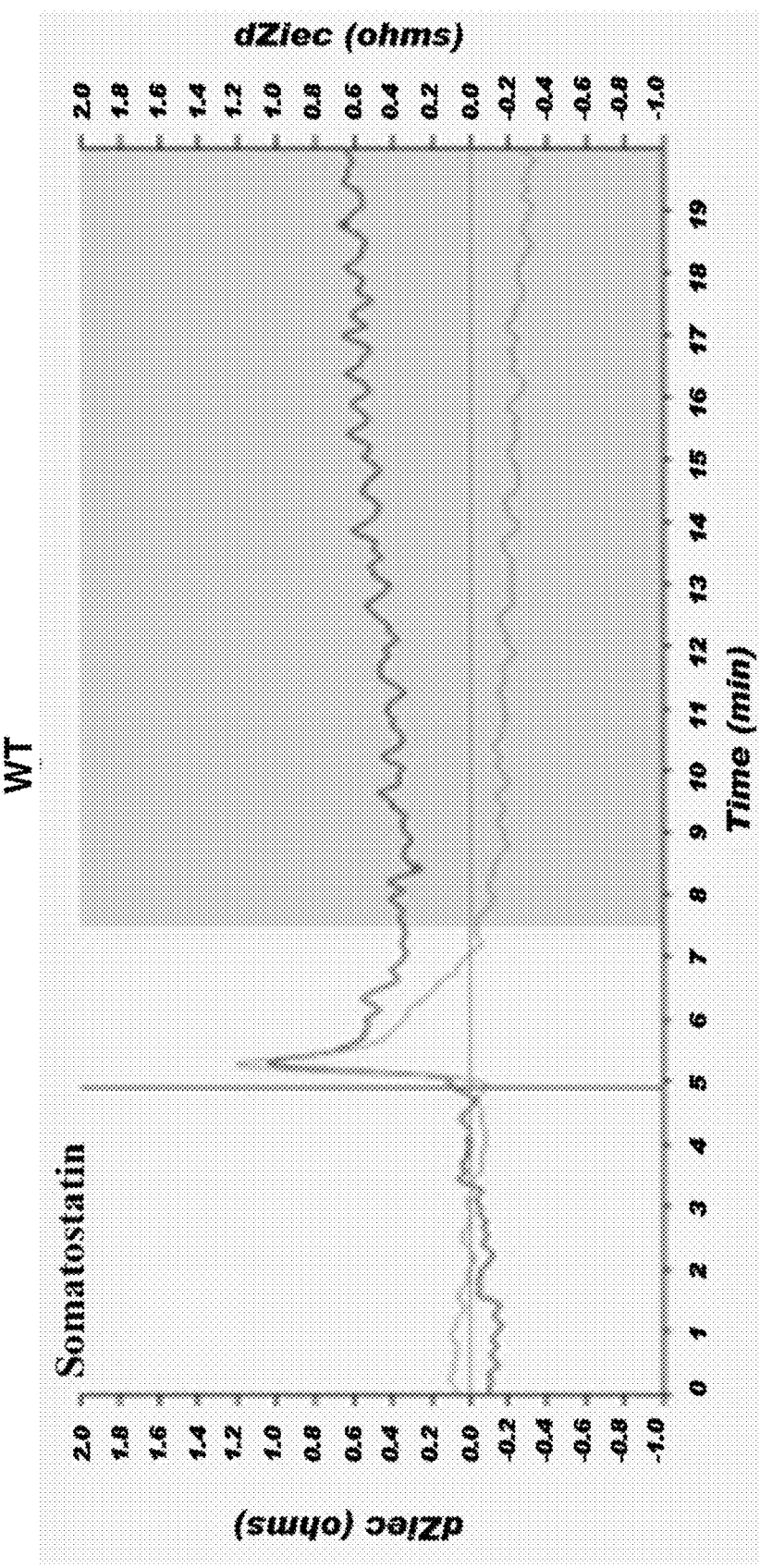
Figure 2F:
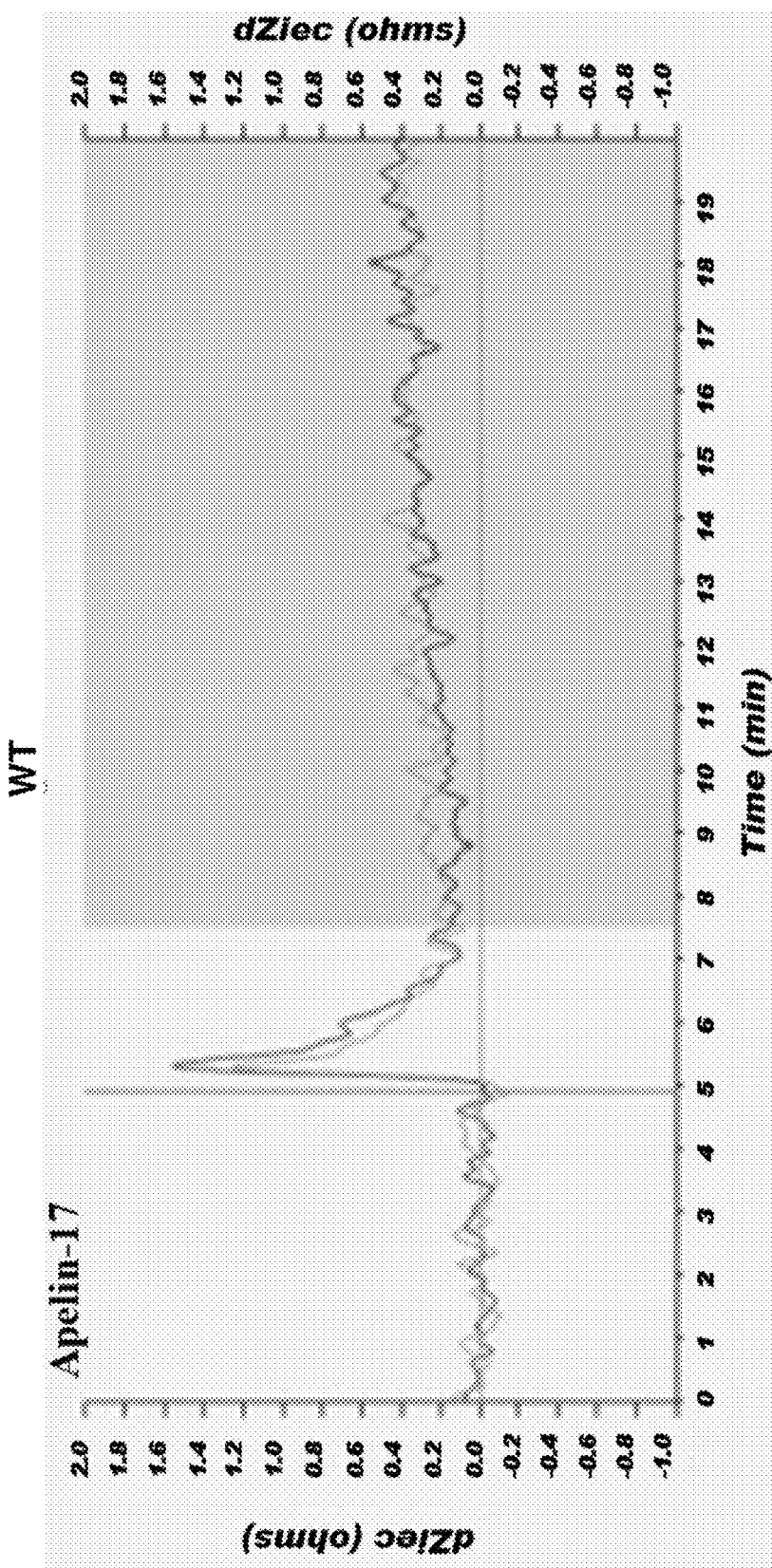
Figure 2G:
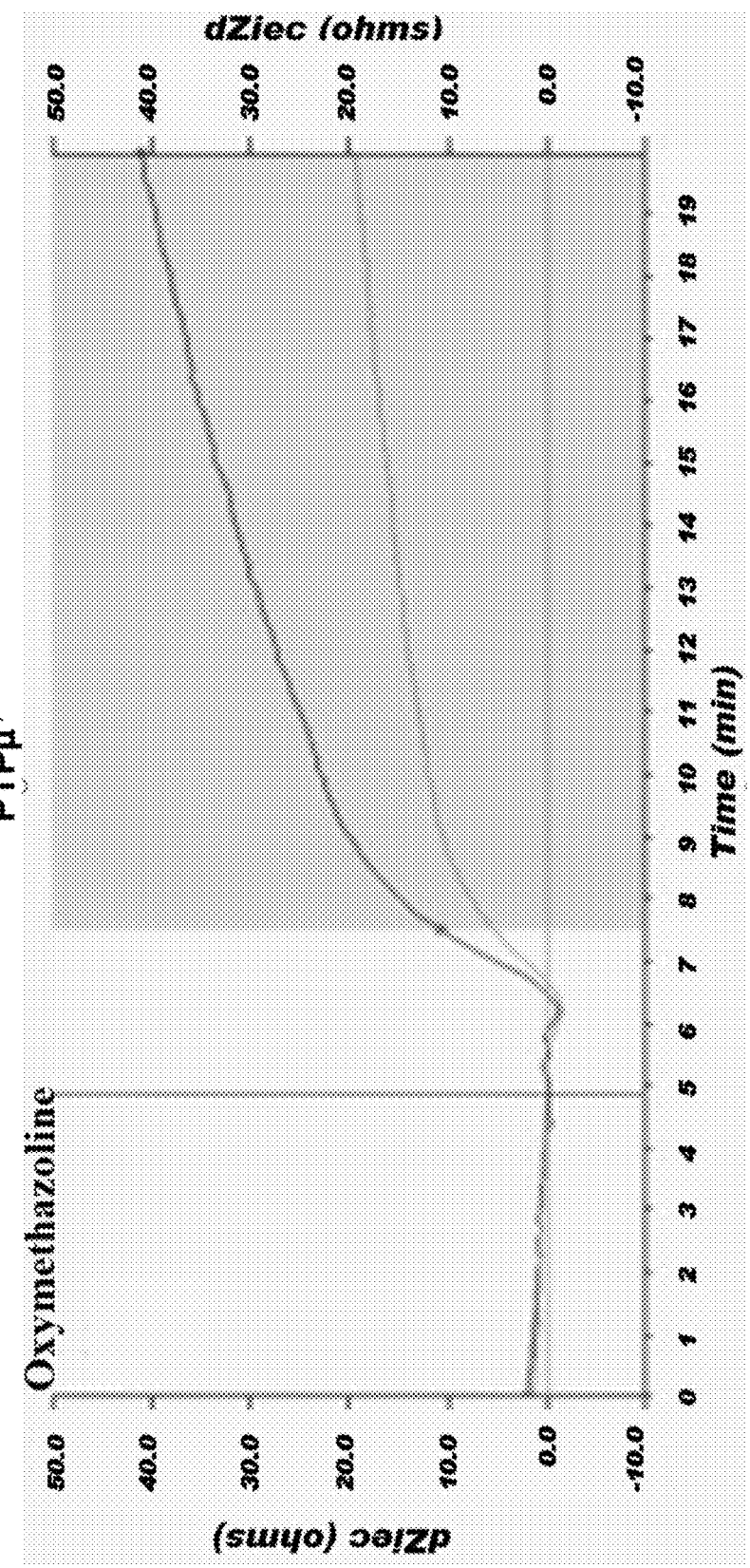
Figure 2H:
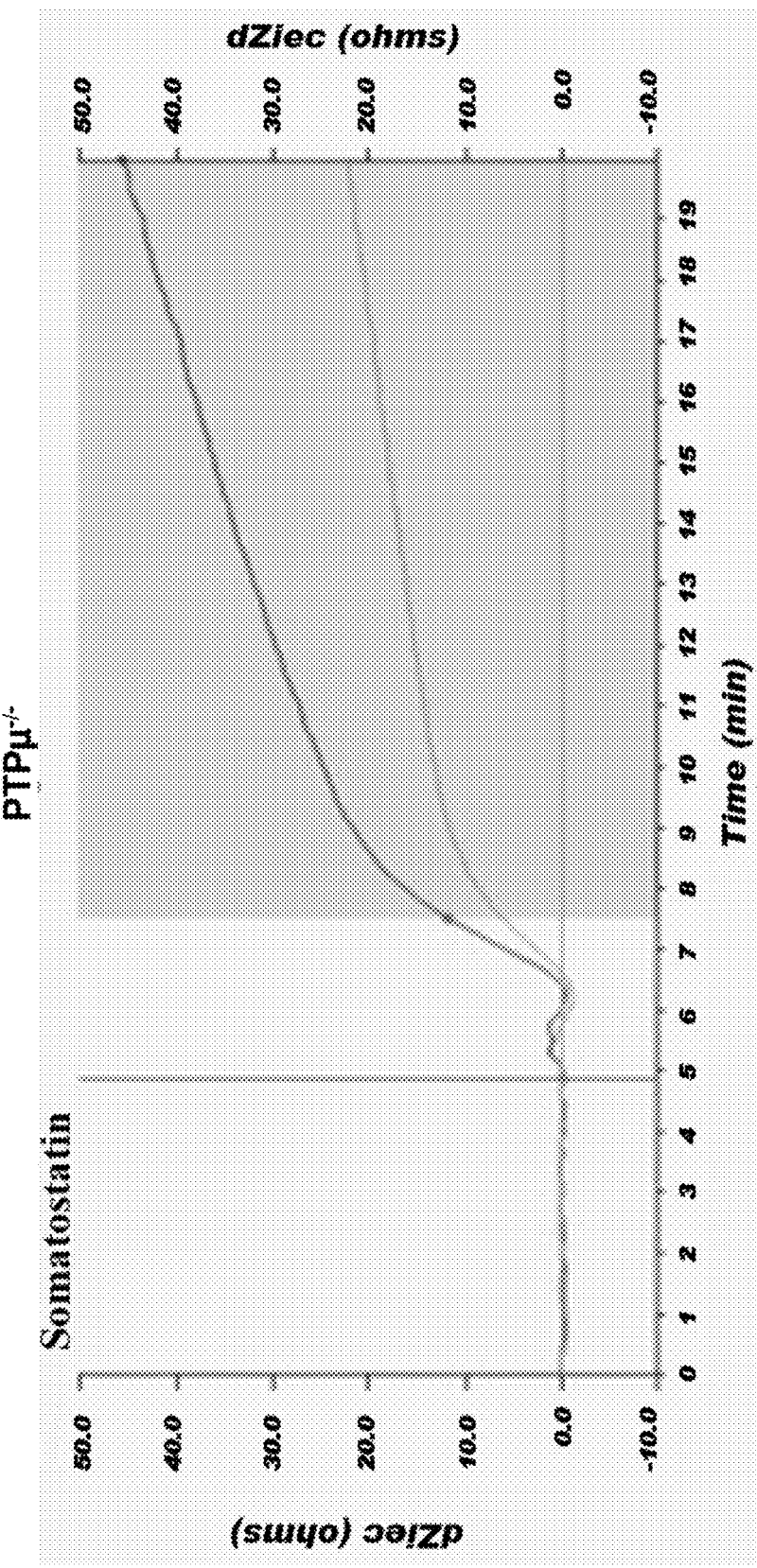
Figure 21:
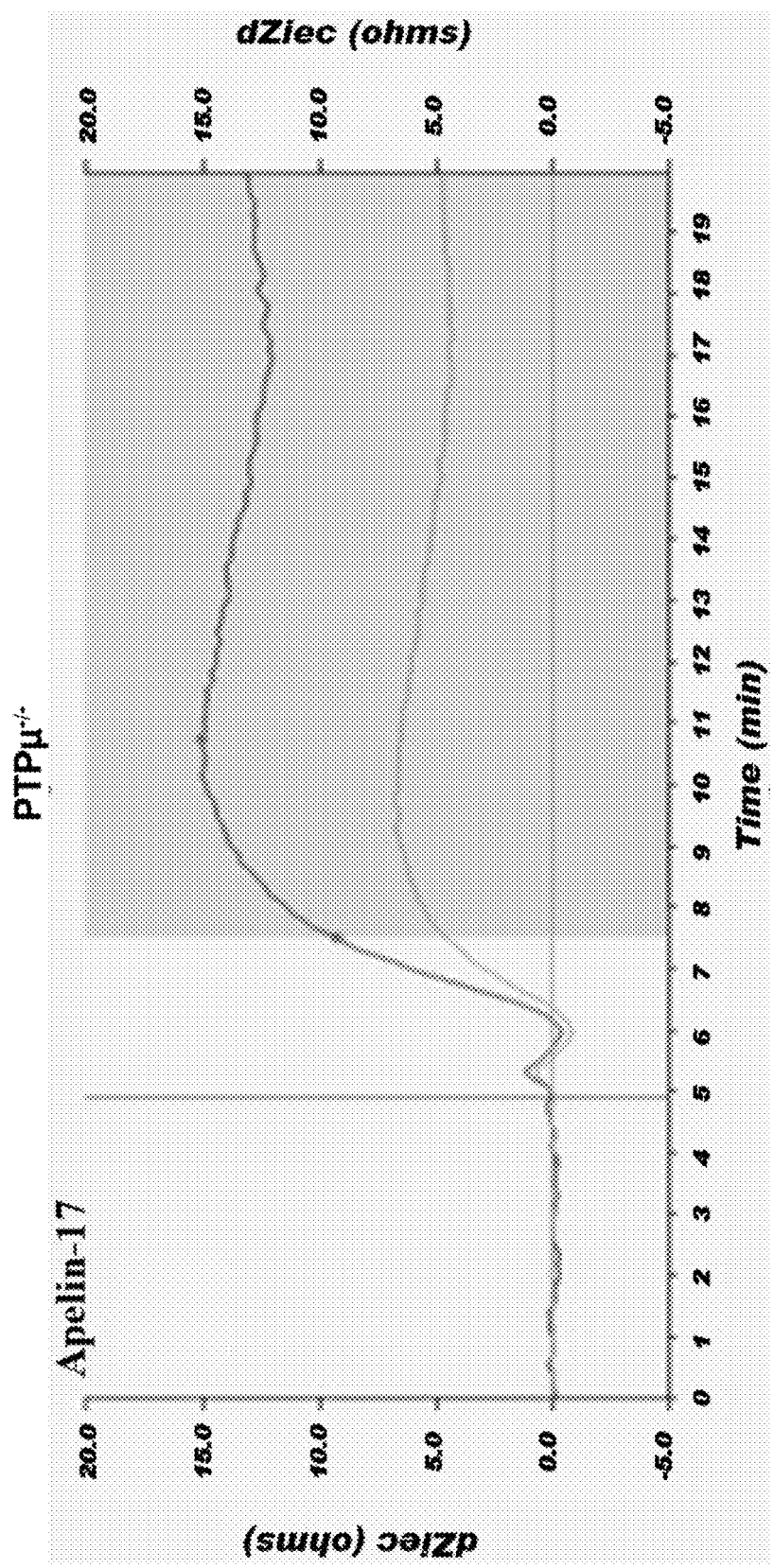
Figure 2J:
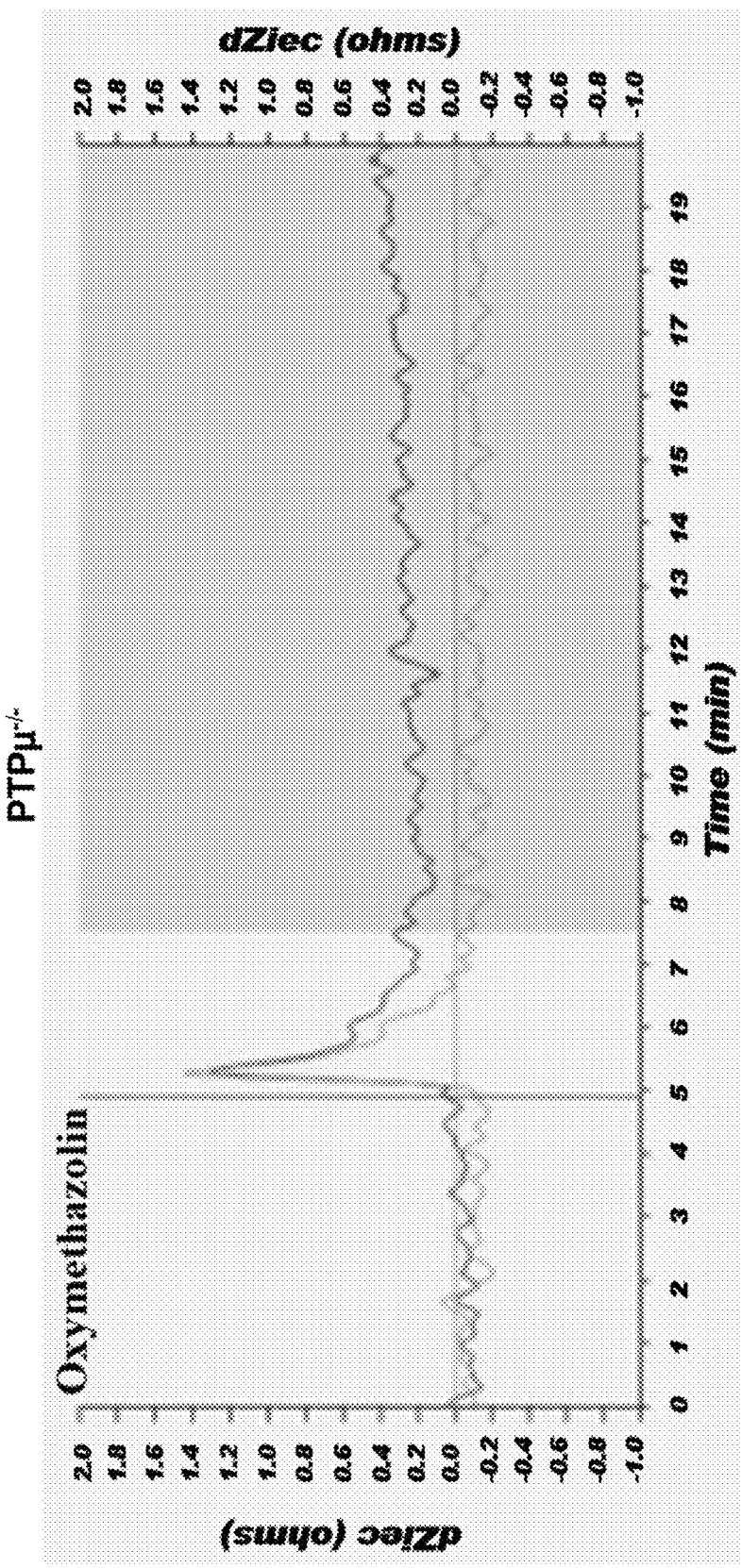
Figure 2K:
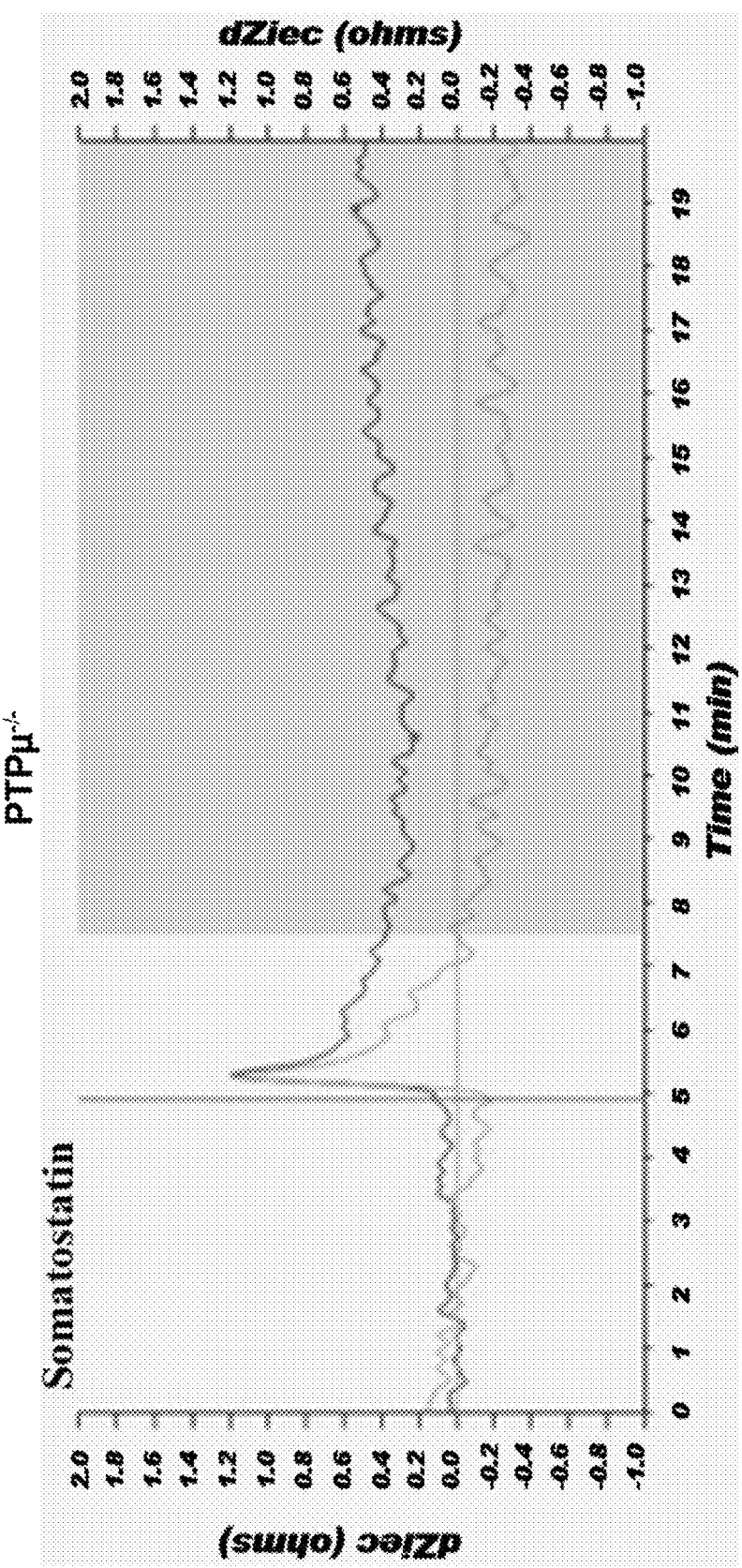
Figure 2L:
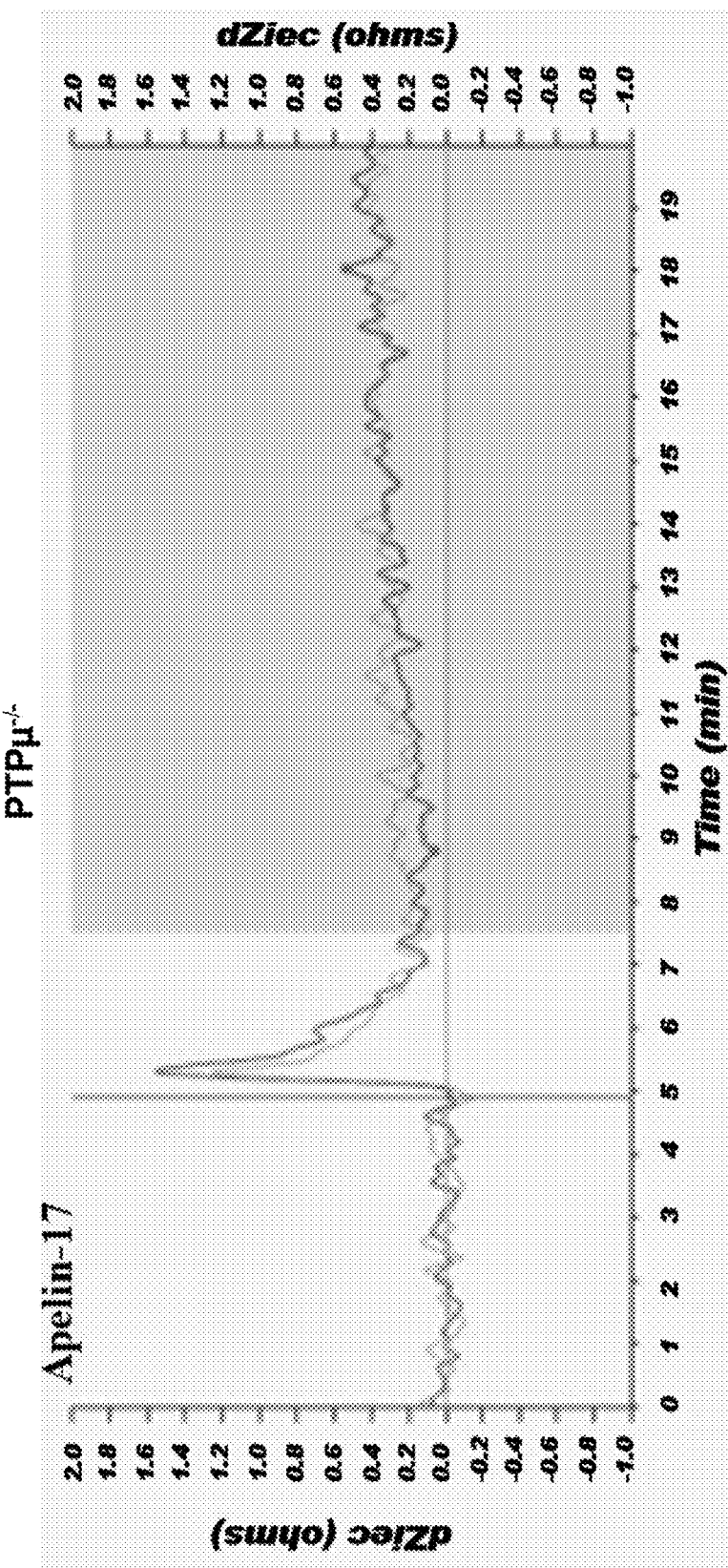
Figure 3A:
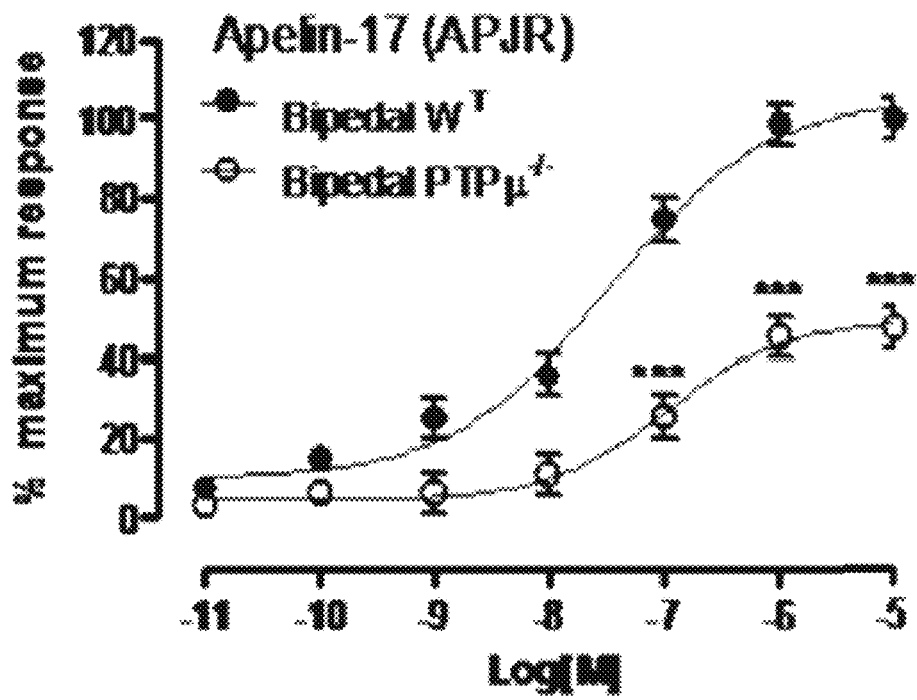
FIGS. 3A-H shows that the lack of PTPµ exacerbates the defective GiPCR signaling in bipedal mice.
Figure 3B:
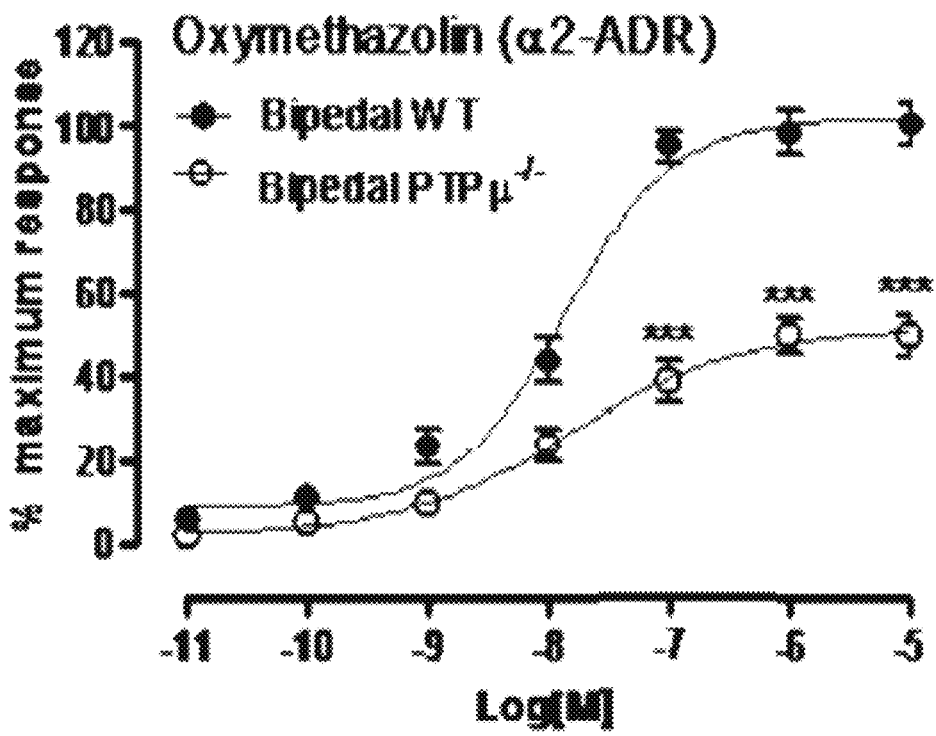
Figure 3C:
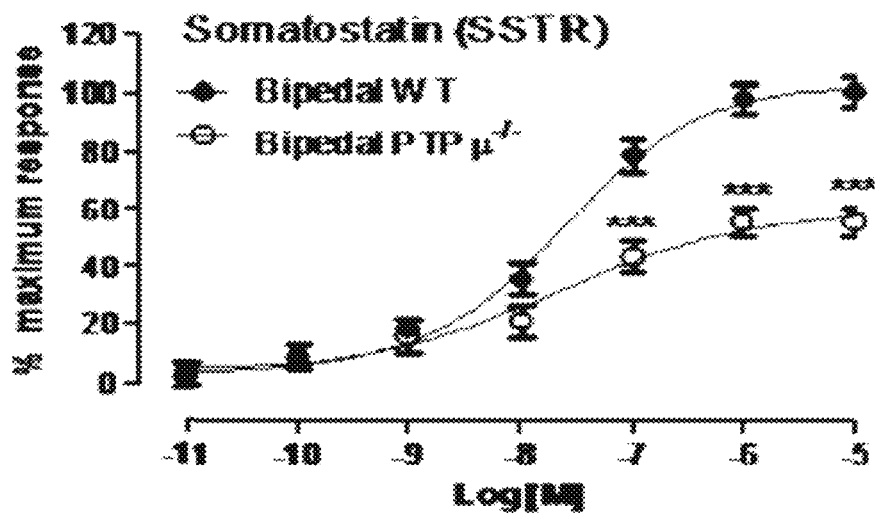
Figure 3D:
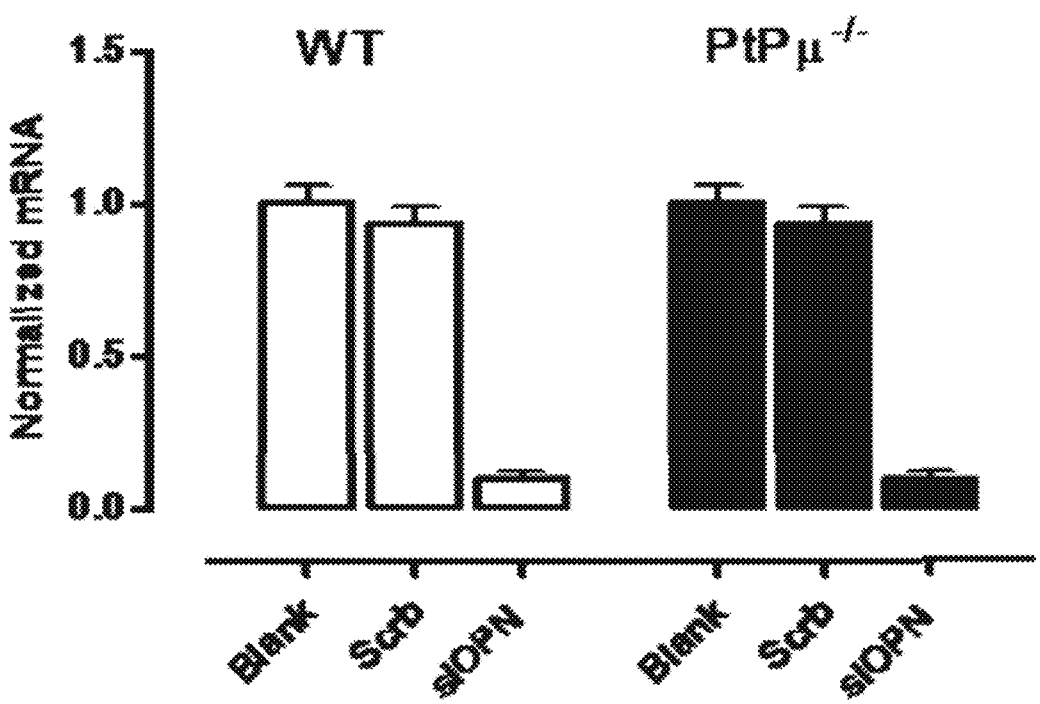
Figure 3E:
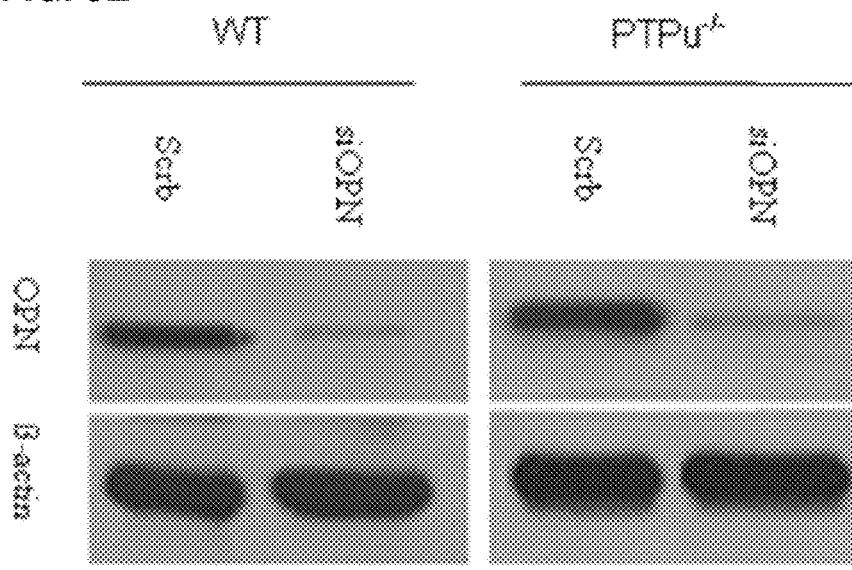
Figure 3F:
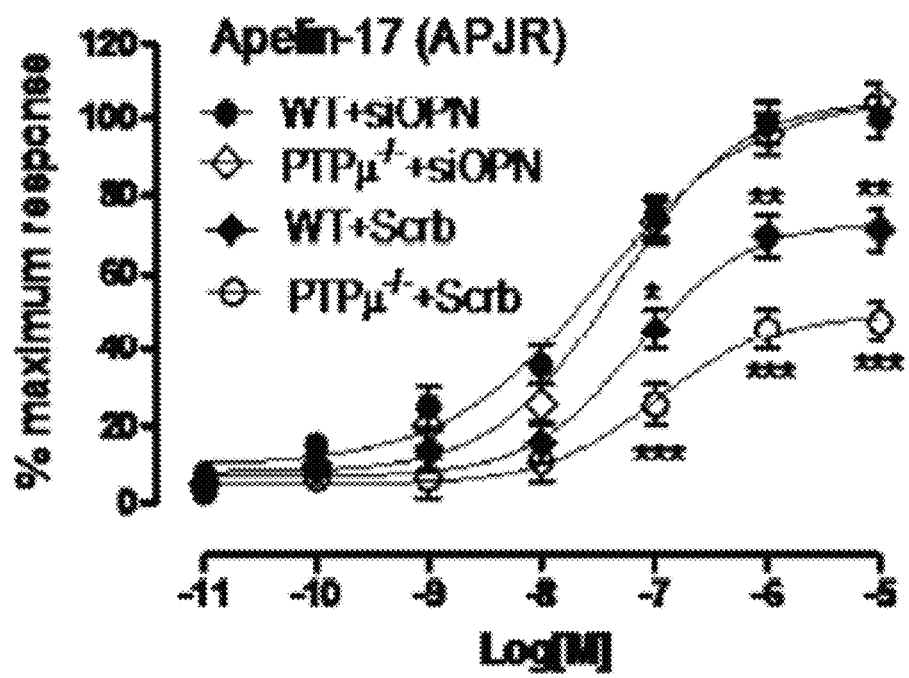
Figure 3G:
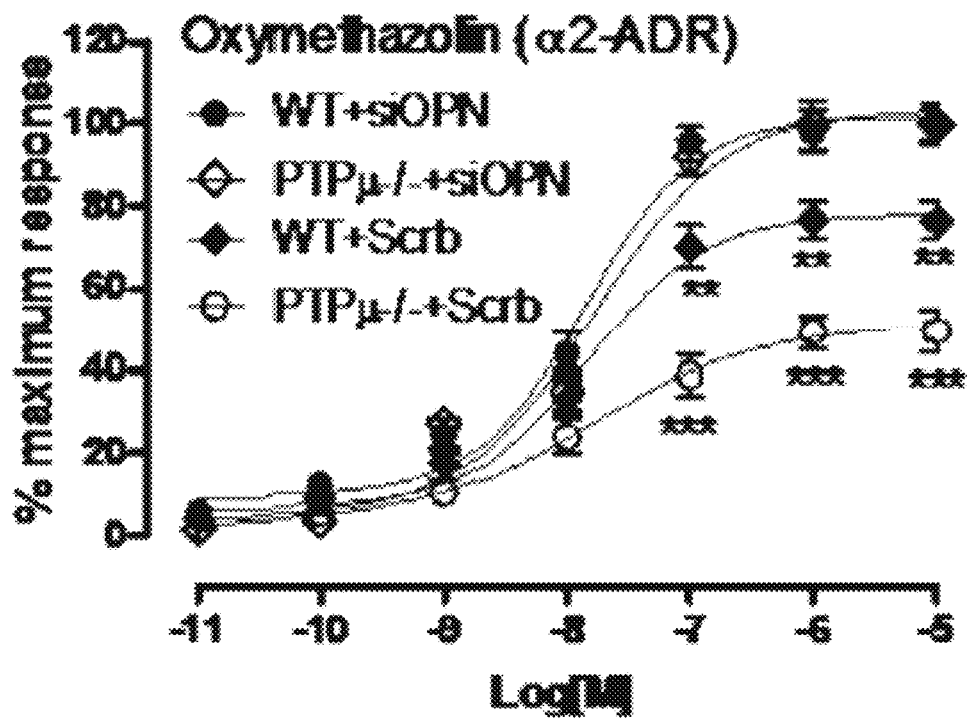
Figure 3H:
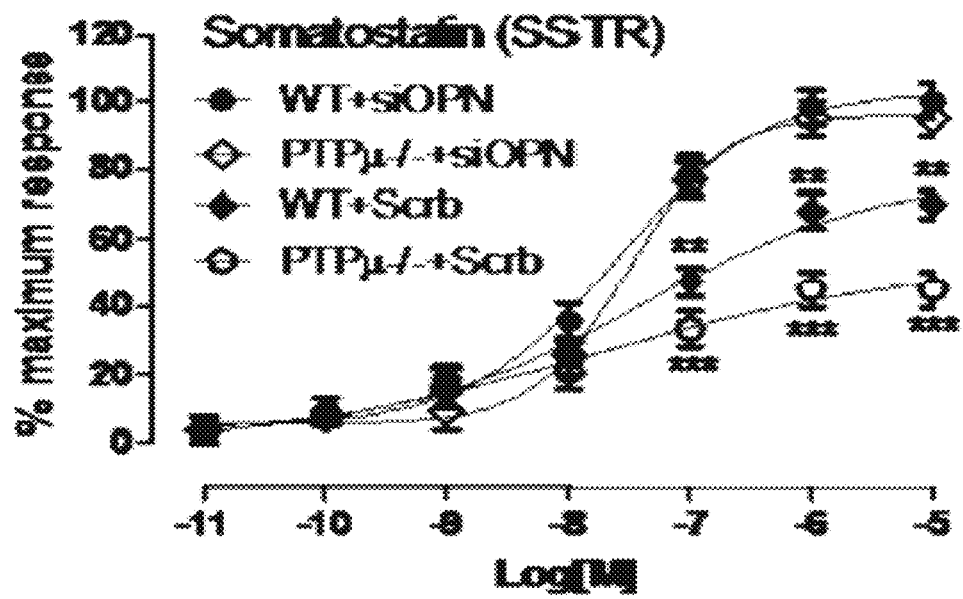

As used herein the terms "risk of developing scoliosis" refer to a genetic or metabolic predisposition of a subject to develop a scoliosis (i.e. spinal deformity) and/or to develop a more severe scoliosis at a future time (i.e., curve progression). For instance, an increase of the Cobb's angle of a subject (e.g. from 40° to 50°, or from 18° to 25°) is a "development" of scoliosis.

In an embodiment, the above-mentioned subject is a likely candidate for developing a scoliosis, such as idiopathic scoliosis (e.g., Infantile Idiopathic Scoliosis, Juvenile Idiopathic Scoliosis or Adolescent Idiopathic Scoliosis (AIS)). As used herein the expression "likely candidate for developing scoliosis" or "likely to develop scoiosis" include subjects (e.g., children) of which at least one parent has a scoliosis (e.g., adolescent idiopathic scoliosis). Among other factors, age (adolescence), gender and other family antecedent are factors that are known to contribute to the risk of developing a scoliosis and are used to a certain degree to assess the risk of developing a scoliosis. In certain subjects, scoliosis develops rapidly over a short period of time to the point of requiring a corrective surgery (often when the deformity reaches a Cobb's angle ≥50°). Current courses of action available from the moment a scoliosis such as AIS is diagnosed (when scoliosis is apparent) include observation (when Cobb's angle is around 10-25°), orthopedic devices (when Cobb's angle is around 25-30°), and surgery (over 45°). A more reliable determination of the risk of progression could enable to 1) select an appropriate diet to remove certain food products identified as contributors to scoliosis; 2) select the best therapeutic agent; and/or 3) select the least invasive available treatment such as postural exercises, orthopedic device, or less invasive surgeries or surgeries without fusions (a surgery that does not fuse vertebra and preserves column mobility). The present invention encompasses selecting the most efficient and least invasive known preventive actions or treatments in view of the determined risk of developing scoliosis.

As used herein the term 'subject' is meant to refer to any mammal including human, mouse, rat, dog, chicken, cat, pig, monkey, horse, etc. In a particular embodiment, it refers to a human.

A "subject in need thereof" or a "patient" in the context of the present invention is intended to include any subject that will benefit or that is likely to benefit from an increase in GiPCR signaling. In an embodiment, the subject in need thereof is a subject that will benefit or that is likely to benefit from i) an inhibitor of PIPK1γ tyrosine phosphorylation; ii) an activator of PIPK1γ tyrosine dephosphorylation (e.g., PTPµ, or any compound able to increase PTPµ's level (i.e., PTPµ expression at the transcriptional and/or translational level and/or PTPµ stability) or activity (e.g., dephosphorylating activity)); ii) an inhibitor of PIPK1γ expression or activity; or iv) any combination of the above. In an embodiment, a subject in need thereof is a subject diagnosed with a scoliosis (e.g., AIS). In another embodiment, the subject in need thereof is at risk of developing a scoliosis or is lkely to develop a scoliosis (e.g., AIS).

As used herein the terminology "biological sample" refers to any solid or liquid sample isolated from a living being. In a particular embodiment, it refers to any solid or liquid sample isolated from a human. Without being so limited it includes a biopsy material, blood, tears, saliva, maternal milk, synovial fluid, urine, ear fluid, amniotic fluid and cerebrospinal fluid. In a specific embodiment it refers to a blood sample.

As used herein the terminology "blood sample" is meant to refer to blood, plasma or serum.

As used herein the terminology "control sample" is meant to refer to a sample that does not come from a subject known to i) have decreased GiPCR signaling; i) have scoliosis or ii) be a likely candidate for developing a scoliosis. In methods for determining the risk of developing scoliosis in a subject that is pre-diagnosed with scoliosis, the control sample may however also come from the subject under scrutiny at an earlier stage of the disease or disorder. In a specific embodiment, the control sample can come from another subject diagnosed with scoliosis and belonging to the same functional group (e.g., FG1, FG2 or FG3) at an earlier (or later stage) of the disease or disorder.

As used herein the terminology "control" is meant to encompass "control sample". In certain embodiments, the term "control" also refers to the average or median value obtained following determination of PTPµ expression (e.g., protein level) and/or activity (e.g., phosphatase activity) and/or PIPK1γ expression (e.g., protein level) and/or activity (e.g., protein kinase activity in a plurality of samples (e.g., samples obtained from several subjects not known to have scoliosis and not known to be a likely candidate for developing scoliosis).

As used herein the term 'treating' or 'treatment' in reference to scoliosis is meant to refer to at least one of a reduction of Cobb's angle in a preexisting spinal deformity, improvement of column mobility, preservation/maintenance of column mobility, improvement of equilibrium and balance in a specific plan; maintenance/preservation of equilibrium and balance in a specific plan; improvement of functionality in a specific plan, preservation/maintenance of functionality in a specific plan, cosmetic improvement, and combination of any of the above.

As used herein the term "preventing" or "prevention" in reference to scoliosis is meant to refer to a at least one of a reduction in the progression of a Cobb's angle in a patient having a scoliosis or in an asymptomatic patient, a complete prevention of apparition of a spinal deformity, including changes affecting the rib cage and pelvis in 3D, and a combination of any of the above.

The terms "suppressor", "inhibitor" and "antagonist" are well known in the art and are used herein interchangeably. They include intracellular as well as extracellular inhibitors.

| Gene (GeneID) | Protein (accession No.) | mRNA sequence | Amino acid sequence |
|---|---|---|---|
| PIPK1γ (23396) | PIPK1γ isoform 1 (NP_001182662.1) (NM_001195733.1) | SEQ ID NO: 27 | SEQ ID NO: 28 |
| PIPK1γ (23396) | PIPK1γ isoform 2 (NP_036530.1) (NM_012398.2) | SEQ ID NO: 29 | SEQ ID NO: 30 |
| PIPK1γ (23396) | PIPK1γ isoform 3 (or X1) (XP_005259580.1) (XM_005259523) | SEQ ID NO: 31 | SEQ ID NO: 32 |
| PIPK1γ (23396) | PIPK1γ isoform 4 | N.A. | SEQ ID NO: 33 |
| PIPK1γ (23396) | PIPK1γ isoform X2 (XP_006722775) (XM_006722712.1) | SEQ ID NO: 34 | SEQ ID NO: 35 |
| PTPμ (5797) | PTPμ isoform 1 (NP_001098714.1) (NM_001105244) | SEQ ID NO: 36 | SEQ ID NO: 37 |
| PTPμ (5797) | PTPμ isoform 2 (NP_002836.3) (NM_002845.3) | SEQ ID NO: 38 | SEQ ID NO: 39 |

The terms "inhibitor of PIPK1γ activity" include any compound able to negatively affect PIPK1γ's (e.g., Gene ID: 23396, NM_012398.2, NP_036530.1) activity (e.g., catalytic activity) and include agents that promote the dephosphorylation of PIPK1γ (i.e., activator of PIPK1γ tyrosine dephosphorylation) and agents that inhibit the phosphorylation of PIPK1γ (i.e., inhibitor of PIPK1γ tyrosine phosphorylation). Inhibitors of PIPK1γ activity include, without being so limited, antibodies, antibody fragments, small molecules, peptides, etc. They further include, without being so limited, PP-242, R406, TG-100-115, ruboxistaurin, GSK690693, pazopanib, alvocidib, SB203580 and staurosporine. Relevant compounds can also be identified using a screening method for identifying an agent that modulates PIPK1γ trafficking of E-cadherin described in US20070161060A1.

In an embodiment, the inhibitor of PIPK1γ activity is a neutralizing antibody directed against (or specifically binding to) a human PIPK1γ polypeptide. Antibodies are further described below.

The terms "activator of PIPK1γ tyrosine dephosphorylation" include any compound able to negatively affect the tyrosine phosphorylation of PIPK1γ (i.e., reduce the phosphorylation level of PIPK1γ). Without being so limited, such activators include phosphatases such as PTPμ (e.g., NM_001105244.1, NP_001098714.1), and any compound able to increase the expression (i.e., at the transcriptional and/or translational level and/or stability) or activity (e.g., phosphatase activity) of PTPμ.

The expression "inhibitor of PIPK1γ tyrosine phosphorylation" includes any compound able to negatively affect the tyrosine phosphorylation of PIPK1γ. Without being so limited, such inhibitors include Scr inhibitors (e.g., PP2, from supplier Sigma Aldrich: Src-inhibitor-1 (4-(4'-(phenexyanilino)-6,7-dimethoxyquinazolne); from supplier Tocris: A419259 trihydrodoride, AZM 475271, Bosutinib, Herbimycin A, MNS, 1-Naphthyl PP1, PD 166285 dihydrochloride, PP1) and Fak inhibitors (e.g., inhibitor-14 (i.e. 1,2,4, 5-Benzenetetramine tetrahydrochloride), from supplier Sigma Aldrich (as supplier): PF-573228, from supplier Medkoo Bioscience: PF-562271; from supplier Seleckche: NVP-TAE226).

The terms "inhibitor of PIPK1γ expression" include any compound able to negatively affect PIPK1γ's expression (i.e., at the transcriptional and/or translational level) i.e. the level of PIPK1γ mRNA and/or protein or the stability of the protein. Without being so limited, such inhibitors include RNA interference agents (siRNA, shRNA, miRNA), antisense molecules, ribozymes, proteins (e.g., dominant negative, inactive variants), peptides, small molecules, antibodies, antibody fragments, etc. Such RNA interference agents are designed to specifically hybridize with their target nucleic acid under suitable conditions and are thus substantially complementary their target nucleic acid.

The terms "stimulator/enhancer of PTPμ expression" include any compound able to positively affect PTPμ's expression (i.e., at the transcriptional and/or translational level) i.e. the level of PTPμ mRNA and/or protein or the stability of the protein.

The present invention also relates to methods for the determination of the level of expression (i.e. transcript (RNA) or translation product (protein)), stability, and/or activity, of PTPμ and/or PIPK1γ. In specific embodiments, it also includes a method that comprises the determination of the level of expression and/or activity of one or more other scoliosis markers. For example, it may include the determination of the level of expression (i.e. transcript or translation product) and/or activity of OPN, sCD44, etc. as disclosed in WO 2008/119170 to Moreau. The present invention therefore encompasses any known method for such determination including Elsa (Enzyme Unked Immunosorbent Assay), RIA (Radioimmunoassay), immunofluorescence, real time PCR and competitive (or quantitative) PCR (qPCR), Northern blots, nuclease protection, plaque hybridization and slot blots.

The present invention also concerns isolated nucleic acid molecules including probes and primers to detect PTPμ and/or PIPK1γ (and optionally other scoliosis markers (e.g., OPN, sCD44, etc). In specific embodiments, the isolated nucleic acid molecules have no more than 300, or no more than 200, or no more than 100, or no more than 90, or no more than 80, or no more than 70, or no more than 60, or no more than 50, or no more than 40 or no more than 30 nucleotides. In specific embodiments, the isolated nucleic acid molecules have at least 17, or at least 18, or at least 19, or at least 20, or at least 30, or at least 40 nucleotides. In other specific embodiments, the isolated nucleic acid molecules have at least 20 and no more than 300 nucleotides. In other specific embodiments, the isolated nucleic acid molecules have at least 20 and no more than 200 nucleotides. In other specific embodiments, the isolated nucleic acid molecules have at least 20 and no more than 100 nucleotides. In other specific embodiments, the isolated nucleic acid molecules have at least 20 and no more than 90 nucleotides. In other specific embodiments, the isolated nucleic acid molecules have at least 20 and no more than 80 nucleotides. In other specific embodiments, the isolated nucleic acid molecules have at least 20 and no more than 70 nucleotides. In other specific embodiments, the isolated nucleic acid molecules have at least 20 and no more than 60 nucleotides. In other specific embodiments, the isolated nucleic acid molecules have at least 20 and no more than 50 nucleotides. In other specific embodiments, the isolated nucleic acid molecules have at least 20 and no more than 40 nucleotides. In other specific embodiments, the isolated nucleic acid molecules have at least 17 and no more than 40 nucleotides. In other specific embodiments, the isolated nucleic acid molecules have at least 20 and no more than 30 nucleotides. In other specific embodiments, the isolated nucleic acid molecules have at least 17 and no more than 30 nucleotides. In other specific embodiments, the isolated nucleic acid molecules have at least 30 and no more than 300 nucleotides. In other specific embodiments, the isolated nucleic acid molecules have at least 30 and no more than 200 nucleotides. In other specific embodiments, the isolated nucleic acid molecules have at least 30 and no more than 100 nucleotides. In other specific embodiments, the isolated nucleic acid molecules have at least 30 and no more than 90 nucleotides. In other specific embodiments, the isolated nucleic acid molecules have at least 30 and no more than 80 nucleotides. In other specific embodiments, the isolated nucleic acid molecules have at least 30 and no more than 70 nucleotides. In other specific embodiments, the isolated nucleic acid molecules have at least 30 and no more than 60 nucleotides. In other specific embodiments, the isolated nucleic acid molecules have at least 30 and no more than 50 nucleotides. In other specific embodiments, the isolated nucleic acid molecules have at least 30 and no more than 40 nucleotides. It should be understood that in real-time PCR, primers also constitute probe without the traditional meaning of this term. Primers or probes appropriate to detect PTPµ and/or PIPK1γ in the methods of the present invention can be designed with known methods using sequences distributed across their respective nucleotide sequence. The probes and/or primers of the present invention are designed to specifically hybridize with their target nucleic acid (PIPK1γ (e.g., SEQ ID NO: 27, 29, 31 and/or 34) and PTPµ (SEQ ID NO: 36 and/or 38). In an embodiment, the primers and probes of the present invention are substantially complementary to their target nucleic acid.

Substantially complementary nucleic acids are nucleic acids in which the complement of one molecule is substantially identical to the other molecule. Two nucleic acid or protein sequences are considered substantially identical if, when optimally aligned, they share at least about 70% sequence identity. In alternative embodiments, sequence identity may for example be at least 75%, at least 80%, at least 85%, at least 90%, at least 95%, at least 96%, at least 98% or at least 99%. Optimal alignment of sequences for comparisons of identity may be conducted using a variety of algorithms, such as the local homology algorithm of Smith and Waterman, 1981, Adv. Appl. Math 2: 482, the homology alignment algorithm of Needleman and Wunsch, 1970, J. Mol. Biol. 48:443, the search for similarity method of Pearson and Lipman, and the computerized implementations of these algorithms (such as GAP, BESTFIT, FASTA and TFASTA in the Wisconsin Genetics Software Package, Genetics Computer Group, Madison, Wis., U.S.A). Sequence identity may also be determined using the BLAST algorithm, described in Altschul et al. 1990 (using the published default settings). Software for performing BLAST analysis may be available through the National Center for Biotechnology Information (through the internet at www.ncbi.nlm.nih.gov). The BLAST algorithm involves first identifying high scoring sequence pairs (HSPs) by identifying short words of length W in the query sequence that either match or satisfy some positive-valued threshold score T when aligned with a word of the same length in a database sequence. T is referred to as the neighborhood word score threshold. Initial neighborhood word hits act as seeds for initiating searches to find longer HSPs. The word hits are extended in both directions along each sequence for as far as the cumulative alignment score can be increased. Extension of the word hits in each direction is halted when the following parameters are met: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T and X determine the sensitivity and speed of the alignment. One measure of the statistical similarity between two sequences using the BLAST algorithm is the smallest sum probability (P(N)), which provides an indication of the probability by which a match between two nucleotide or amino acid sequences would occur by chance. In alternative embodiments of the invention, nucleotide or amino acid sequences are considered substantially identical if the smallest sum probability in a comparison of the test sequences is less than about 1, preferably less than about 0.1, more preferably less than about 0.01, and most preferably less than about 0.001.

An alternative indication that two nucleic acid sequences are substantially complementary is that the two sequences hybridize to each other under moderately stringent, or preferably stringent, conditions. Hybridization to filter-bound sequences under moderately stringent conditions may, for example, be performed in 0.5 M NaHPO4, 7% sodium dodecyl sulfate (SDS), 1 mM EDTA at 65° C., and washing in 0.2×SSC/0.1% SDS at 42° C. Alternatively, hybridization to filter-bound sequences under stringent conditions may, for example, be performed in 0.5 M NaHPO4, 7% SDS, 1 mM EDTA at 65° C., and washing in 0.1×SSC/0.1% SDS at 68° C. Hybridization conditions may be modified in accordance with known methods depending on the sequence of interest Generally, stringent conditions are selected to be about 5° C. lower than the thermal melting point for the specific sequence at a defined ionic strength and pH.

Probes of the invention can be utilized with naturally occurring sugar-phosphate backbones as well as modified backbones including phosphorothioates, dithionates, alkyl phosphonates and α-nucleotides and the like. Modified sugar-phosphate backbones are generally known. Probes of the invention can be constructed of either ribonucleic acid (RNA) or deoxyribonucleic acid (DNA), and preferably of DNA.

The types of detection methods in which probes can be used include Southern blots (DNA detection), dot or slot blots (DNA, RNA), and Northern blots (RNA detection).

Although less preferred, labeled proteins could also be used to detect a particular nucleic acid sequence to which it binds. Other detection methods include kits containing probes on a dipstick setup and the like.

As used herein the terms "detectably labeled" refer to a marking of a probe or an antibody in accordance with the presence invention that will allow the detection of PTPµ and/or PIPK1γ in accordance with the present invention. Although the present invention is not specifically dependent on the use of a label for the detection of a particular nucleic acid sequence, such a label might be beneficial, by increasing the sensitivity of the detection. Furthermore, it enables automation. Probes can be labeled according to numerous well known methods. Non-limiting examples of labels include $^3H$, $^{14}C$, $^{32}P$, and $^{36}S$. Non-limiting examples of detectable markers include ligands, fluorophores, chemiluminescent agents, enzymes, and antibodies. Other detectable markers for use with probes, which can enable an increase in sensitivity of the method of the invention, include biotin and radionucleotides. It will become evident to the person of ordinary skill that the choice of a particular label dictates the manner in which it is bound to the probe.

As commonly known, radioactive nucleotides can be incorporated into probes of the invention by several methods. Non-limiting examples thereof include kinasing the 5' ends of the probes using gamma 32P ATP and polynucleotide kinase, using the Klenow fragment of Pol I of *E. coli* in the presence of radioactive dNTP (e.g. uniformly labeled DNA probe using random oligonucleotide primers in low-melt gels), using the SP6T7 system to transcribe a DNA segment in the presence of one or more radioactive NTP, and the like.

The present invention also relates to methods of selecting compounds. As used herein the term 'compound' is meant to encompass natural, synthetic or semi-synthetic compounds, including without being so limited chemicals, macromolecules, cell or tissue extracts (from plants or animals), nucleic acid molecules, peptides, antibodies and proteins.

The present invention also relates to arrays. As used herein, an "array" is an intentionally created collection of molecules which can be prepared either synthetically or biosynthetically. The molecules in the array can be identical or different from each other. The array can assume a variety of formats, e.g., libraries of soluble molecules; libraries of compounds tethered to resin beads, silica chips, or other solid supports.

As used herein "array of nucleic acid molecules" is an intentionally created collection of nucleic acids which can be prepared either synthetically or biosynthetically in a variety of different formats (e.g., libraries of soluble molecules; and libraries of oligonucleotides tethered to resin beads, silica chips, or other solid supports). Additionally, the term "array" is meant to include those libraries of nucleic acids which can be prepared by spotting nucleic acids of essentially any length (e.g., from 1 to about 1000 nucleotide monomers in length) onto a substrate. The term "nucleic acid" as used herein refers to a polymeric form of nucleotides of any length, either ribonucleotides, deoxyribonucleotides or peptide nucleic acids (PNAs), that comprise purine and pyrimidine bases, or other natural, chemically or biochemically modified, non-natural, or derivatized nucleotide bases. The backbone of the polynucleotide can comprise sugars and phosphate groups, as may typically be found in RNA or DNA, or modified or substituted sugar or phosphate groups. A polynucleotide may comprise modified nucleotides, such as methylated nucleotides and nucleotide analogs. The sequence of nucleotides may be interrupted by non-nucleotide components. Thus the terms nucleoside, nucleotide, deoxynucleoside and deoxynucleotide generally include analogs such as those described herein. These analogs are those molecules having some structural features in common with a naturally occurring nucleoside or nucleotide such that when incorporated into a nucleic acid or oligonucleotide sequence, they allow hybridization with a naturally occurring nucleic acid sequence in solution. Typically, these analogs are derived from naturally occurring nucleosides and nucleotides by replacing and/or modifying the base, the ribose or the phosphodiester moiety. The changes can be tailor made to stabilize or destabilize hybrid formation or enhance the specificity of hybridization with a complementary nucleic acid sequence as desired.

As used herein "sold support", "support", and "substrate" are used interchangeably and refer to a material or group of materials having a rigid or semi-rigid surface or surfaces. In many embodiments, at least one surface of the solid support will be substantially flat, although in some embodiments it may be desirable to physically separate synthesis regions for different compounds with, for example, wells, raised regions, pins, etched trenches, or the like. According to other embodiments, the solid support(s) will take the form of beads, resins, gels, microspheres, or other geometric configurations.

Any known nucleic acid arrays can be used in accordance with the present invention. For instance, such arrays include those based on short or longer oligonucleotide probes as well as cDNAs or polymerase chain reaction (PCR) products. Other methods include serial analysis of gene expression (SAGE), differential display, as well as subtractive hybridization methods, differential screening (DS), RNA arbitrarily primer (RAP)-PCR, restriction endonucleolytic analysis of differentially expressed sequences (READS), amplified restriction fragment-length polymorphisms (AFLP).

Antibodies

The present invention encompasses using antibodies for detecting or determining PTPµ and/or PIPK1γ (e.g., tyrosine phosphorylated PIPK1γ) levels for instance in the samples of a subject and for including in kits of the present invention. Neutralizing antibodies may also be used to inhibit PIPK1γ's phosphorylation to increase GiPCR signaling in cells (e.g., in a subject in need thereof). Antibodies that specifically bind to these biological markers can be produced routinely with methods further described below. The present invention also encompasses using antibodies commercially available. Without being so limited antibodies that specifically bind to PTPµ and/or PIPK1γ include those listed in Table 1 below.

TABLE 1 commercially available antibodies and ELISA kits for PTPµ and PIPKγ (e.g., tyrosine phosphorylated)

| Description | Supplier | Catalogue number | Host | Reactivity | Applications |
|---|---|---|---|---|---|
| Mouse monoclonal SK15 to PTPu | Abcam | AB30321 | mouse | Human | IP, WB |

TABLE 1-continued commercially available antibodies and ELISA kits for PTPµ and PIPKγ (e.g., tyrosine phosphorylated)

| Description | Supplier | Catalogue number | Host | Reactivity | Applications |
|---|---|---|---|---|---|
| Anti-PTP mu antibody | Abcam | AB111207 | goat | Human | ELISA, IHC-P |
| PTPRM monoclonal antibody, clone T10-AF1A8 | Abnova | MAB6540 | mouse | Human | WB, IP |
| PTPRM polyclonal antibody | Abnova | PAB7422 | goat | Human | ELISA |
| PTPRM antibody | Acris Antibodies | 18315-1-AP | rabbit | human, mouse | WB, ELISA |
| PTPRM antibody | Acris Antibodies | AM05259PU-N | mouse | human, mouse, rat, cow | WB |
| PTPRM antibody | Acris Antibodies | AM12097PU-N | mouse | Human | IP, WB |
| PTPRM antibody | Acris Antibodies | AM32664SU-N | mouse | human, mouse, rat, cow, dog | IP, IH, WB |
| PTPRM antibody | Acris Antibodies | H00005797-A01 | mouse | Human | ELISA, WB |
| PTP mu antibody | antibodies-online.com | ABIN306639 | mouse | human, mouse | WB, ELISA |
| PTPRM Antibody | Aviva Systems Biology | OAEB00215 | goat | bovine, dog, human, mouse, rat, rabbit, chicken | ELISA |
| PTPRM Polyclonal Antibody II | Biorbyt | orb19714 | goat | human, mouse, dog | ELISA |
| Anti-PTP mu Antibody | Everest Biotech | EB08229 | goat | Human | ELISA |
| PTP mu | Exalpha | P100M | mouse | Human | WB |
| PTP mu | Exalpha Biologicals | P100M | mouse | human, mouse | WB |
| RPTP Mu antibody | Fitzgerald | 10R-8633 | mouse | Human | IP, WB |
| PTPRM antibody [SK15] | Gene Tex | GTX78230 | mouse | Human | IP, WB |
| PTPRM antibody [SK15], PTPRM antibody, Internal | Gene Tex | GTX88875 | goat | human, mouse, dog | ELISA |
| Peptide-affinity Purified Polyclonal Antibody to PTPRM | Imgenex | IMX-30612 | goat | dog, human, mouse | ELISA |
| Anti-PTPRM/PTP Mu Antibody LS-B4352 IHC-plus | LifeSpan BioSciences, Inc. | LS-B4352 | goat | Human | ELISA, IHC-P |
| Anti-PTPRM/PTP Mu Antibody LS-B4352 IHC-plus | LifeSpan BioSciences, Inc. | LS-C3174 | rabbit | Human | ELISA |
| Anti-PTPRM/PTP Mu Antibody LS-B4352 IHC-plus | LifeSpan BioSciences, Inc. | LS-C26528 | mouse | bovine, human, mouse, rat | WB |
| Anti-PTPRM/PTP Mu Antibody LS-B4352 IHC-plus | LifeSpan BioSciences, Inc. | LS-C75231 | mouse | human, mouse, rat | WB, ELISA |
| Anti-Protein Tyrosine Phosphatase µ Antibody, clone BK2 | Millipore | MAB3740(CH) | mouse | human, mouse, rat, cow, frog | ICC, IP, WB |
| Anti-Protein Tyrosine Phosphatase µ Antibody, clone SBK15 | Millipore | MAB3741(CH) | mouse | human, mouse, rat, dog, cow | ICC, IP, WB |
| PTPmu (BK2) mouse mAb | New England Biolabs | 4485S | mouse | huma, rat, mink | WB, IP |
| PTPRM Antibody (SK15) | Pierce Antibodies | MA1-90601 | mouse | Human | IP, WB |
| PTPu(2C10) | Santa Cruz | sc-56957 | mouse | mouse, rat, human, mink | WB, IP, FCM |
| PTPu(BK2) | Santa Cruz | sc-33651 | mouse | Human | WB, IP, IF |
| PTPu(SBK10) | Santa Cruz | sc-65228 | mouse | mouse, rat, human | WB, IP |
| PTPu(H80) | Santa Cruz | sc-25433 | rabbit | mouse, rat, human, horse, cow, bird | WB, IP, IF, ELISA |
| PTPu(SK15) | Santa Cruz | sc-56959 | mouse | Human | WB, IP |
| PTPu(C-20) | Santa Cruz | sc-1115 | goat | mouse, rat, human, horse, dog, cow, pig, bird | WB, IF, ELISA |
| Monoclonal Anti-Protein Tyrosine Phosphatase µ antibody produced in mouse | Sigma Aldrich | P8984 | mouse | rat, mouse, human, cow | WB, IP |
| Protein Tyrosine Phoshatase, Receptor Type, M (PTPRM) | antibodies-online.com | ABIN1154945 | | | Human ELISA |
| PIPKI g Polyclonal Antibody | ImmunoWay | YT3735 | rabbit | Human | WB, ELISA |
| PIPK I alpha Antibody | Pierce Antibodies | PA5-28215 | rabbit | Human | WB |
| PIPK I γ (H-9) | Santa Cruz | sc-377061 | mouse | mouse, rat, human | WB, IP, IF, IHC(P), ELISA |
| PIPK I γ (A-19) | Santa Cruz | sc-11782 | goat | Human | WB, IP, IF, ELISA |
| PIP5KIC Antibody | MyBiosource.com | MBS856298 | rabbit | Human | WB, ELISA |

Both monoclonal and polyclonal antibodies directed to PTPµ and/or PIPK1γ are included within the scope of this invention as they can be produced by well established procedures known to those of skill in the art. Additionally, any secondary antibodies, either monoclonal or polyclonal, directed to the first antibodies would also be included within the scope of this invention.

As used herein, the expression "anti-PTPµ antibody" or "immunologically specific anti-PTPµ antibody" refers to an antibody that specifically binds to (interacts with) a PTPµ protein and displays no substantial binding to other naturally occurring proteins other than the ones sharing the same antigenic determinants as the PTPµ protein. Similarly, the expression "anti-PIPK1γ antibody" encompassing "anti-phospho-tyrosine PIPK1γ-antibody" refers to an antibody that specifically binds to (interacts with) PIPK1γ (e.g., tyrosine phosphorylated PIPK1γ protein) and displays no substantial binding to other naturally occurring proteins other than the ones sharing the same antigenic determinants as PIPK1γ (e.g., tyrosine phosphorylated PIPK1γ protein). The term antibody or immunoglobulin is used in the broadest sense, and covers monoclonal antibodies (including full length monoclonal antibodies), polyclonal antibodies, multispecific antibodies, and antibody fragments so long as they exhibit the desired biological activity. Antibody fragments comprise a portion of a full length antibody, generally an antigen binding or variable region thereof. Examples of antibody fragments include Fab, Fab', F(ab')$_2$, and Fv fragments, diabodies, linear antibodies, single-chain antibody molecules, single domain antibodies (e.g., from camelids), shark NAR single domain antibodies, and multispecific antibodies formed from antibody fragments. Antibody fragments can also refer to binding moieties comprising CDRs or antigen binding domains including, but not limited to, VH regions ($V_H$, $V_H$—$V_H$), anticains, PepBodies™, antibody-T-cel epitope fusions (Troybodies) or Peptibodies. Additionaly, any secondary antibodies, either monoclonal or polyclonal, directed to the first antibodies would also be included within the scope of this invention.

In general, techniques for preparing antibodies (including monoclonal antibodies and hybridomas) and for detecting antigens using antibodies are well known in the art (Campbel, 1984, In "Monodonal Antibody Technology: Laboratory Techniques in Biochemistry and Molecular Biology", Elsevier Science Publisher, Amsterdam, The Netherlands) and in Harlow et al., 1988 (in: Antibody A Laboratory Manual, CSH Laboratories). The term antibody encompasses herein polyclonal, monoclonal antibodies and antibody variants such as single-chain antibodies, humanized antibodies, chimeric antibodies and immunologically active fragments of antibodies (e.g. Fab and Fab' fragments) which inhibit or neutralize their respective interaction domains in Hyphen and/or are specific thereto.

Polyclonal antibodies are preferably raised in animals by multiple subcutaneous (sc), intravenous (iv) or intraperitoneal (ip) injections of the relevant antigen with or without an adjuvant. It may be useful to conjugate the relevant antigen to a protein that is immunogenic in the species to be immunized, e.g., keyhole limpet hemocyanin, serum albumin, bovine thyroglobulin, or soybean trypsin inhibitor using a bifunctional or derivatizing agent, for example, maleimidobenzoyl sulfosuccinimide ester (conjugation through cysteine residues), N-hydroxysuccinimide (through lysine residues), glutaraldehyde, succinic anhydride, $SOCl_2$, or $R^1N=C=NR$, where R and $R^1$ are different alkyl groups.

Animals may be immunized against the antigen, immunogenic conjugates, or derivatives by combining the antigen or conjugate (e.g., 100 µg for rabbits or 5 µg for mice) with 3 volumes of Freund's complete adjuvant and injecting the solution intradermally at multiple sites. One month later the animals are boosted with the antigen or conjugate (e.g., with ⅕ to ⅒ of the original amount used to immunize) in Freund's complete adjuvant by subcutaneous injection at multiple sites. Seven to 14 days later the animals are bled and the serum is assayed for antibody titer. Animals are boosted until the titer plateaus. Preferably, for conjugate immunizations, the animal is boosted with the conjugate of the same antigen, but conjugated to a different protein and/or through a different cross-linking reagent. Conjugates also can be made in recombinant cell culture as protein fusions. Also, aggregating agents such as alum are suitably used to enhance the immune response.

Monoclonal antibodies may be made using the hybridoma method first described by Kohler et al., Nature, 256: 495 (1975), or may be made by recombinant DNA methods (e.g., U.S. Pat. No. 6,204,023). Monoclonal antibodies may also be made using the techniques described in U.S. Pat. Nos. 6,025,155 and 6,077,677 as well as U.S. Patent Application Publication Nos. 2002/0160970 and 2003/0083293.

In the hybridoma method, a mouse or other appropriate host animal, such as a rat, hamster or monkey, is immunized (e.g., as hereinabove described) to elicit lymphocytes that produce or are capable of producing antibodies that will specifically bind to the antigen used for immunization. Alternatively, lymphocytes may be immunized in vitro. Lymphocytes then are fused with myeloma cells using a suitable fusing agent, such as polyethylene glycol, to form a hybridoma cell.

The hybridoma cells thus prepared are seeded and grown in a suitable culture medium that preferably contains one or more substances that inhibit the growth or survival of the unfused, parental myeloma cells. For example, if the parental myeloma cells lack the enzyme hypoxanthine guanine phosphoribosyl transferase (HGPRT or HPRT), the culture medium for the hybridomas typically will include hypoxanthine, aminopterin, and thymidine (HAT medium), which substances prevent the growth of HGPRT-deficient cells.

As used herein, the term "purified" in the expression "purified antibody" is simply meant to distinguish man-made antibody from an antibody that may naturally be produced by an animal against its own antigens. Hence, raw serum and hybridoma culture medium containing anti-OPN antibody are "purified antibodies" within the meaning of the present invention.

The present invention also encompasses arrays to detect and/or quantify the translation products of PTPµ and/or PIPK1γ. Such arrays include protein micro- or macroarrays, gel technologies including high-resolution 2D-gel methodologies, possibly coupled with mass spectrometry imaging system at the cellular level such as microscopy combined with a fluorescent labeling system.

The present invention also encompasses methods to screen/select for potential useful therapeutic agents using whole cells assays, the therapeutic compound being able to increase i) the transcription and/or synthesis and/or stability of PTPµ; ii) the activity (phosphatase) of PTPµ; and/or able to decrease i) the transcription and/or synthesis and/or stability of PIPK1γ; or i) the activity of PIPK1γ (e.g., by decreasing the tyrosine phosphorylation of PIPK1γ). Cells for use in such methods includes cells of any source (including in house or commercially available cell lines) and type (any tissue). In house cell lines could be made for instance by immortalizing cells from AIS subjects. In specific embodiments, methods of screening of the invention seek to identify agents that inhibit the tyrosine phosphorylation of PIPK1γ and agents that increase PTPµ expression (transcription and/or translation), stability or activity (e.g., phosphatase). Useful cell lines for these embodiments include those producing low levels of PTPµ and/or high levels of tyrosine phosphorylated PIPK1γ. Useful cell lines also include PBMCs.

In a particular embodiment, it includes cells of any cell type derived from a scoliotic patient (whole cell assay). In specific embodiments, it includes osteoblasts, chondrocytes, myoblasts or blood cells including PBMCs including lymphocytes. As used herein, the term "cell derived from a scoliotic patient" refers to cells isolated directly from scoliotic patients, or immortalized cell ines originating from cells isolated directly from scoliotic patients. In specific embodiments, the cells are paraspinal muscle cells. Such cells may be isolated by a subject through needle biopsies for instance.

The present invention also concerns pharmaceutical compositions for modulating (increasing or decreasing) GiPCR cell signaling. In an embodiment, such compositions include agents for increasing GiPCR signaling in a subject in need thereof. For instance, pharmaceutical compositions of the present invention may comprise agents which increase i) the transcription and/or synthesis and/or stability of PTPµ; or ii) the activity (phosphatase) of PTPµ; and/or decrease ii) the transcription and/or synthesis of PIPK1γ (e.g., siRNAs) and/or stability; or iv) the activity of PIPK1γ (e.g., by decreasing the tyrosine phosphorylation of PIPK1γ). Pharmaceutical compositions can be administered by any suitable routes such as nasally, intravenously, intramuscularly, subcutaneously, sublingually, intrathecally, or intradermally. The route of administration can depend on a variety of factors, such as the environment and therapeutic goals.

Dosage

Any suitable amount of a pharmaceutical composition can be administered to a subject. The dosages will depend on many factors including the mode of administration. Typically, the amount of anti-scoliosis composition (e.g., agent that increase GiPCR cell signaling in a subject in need thereof, such as an agent which increases PTPµ expression or activity or that decreases PIPK1γ expression or activity) contained within a single dose will be an amount that effectively prevents, delays or reduces scoliosis without inducing significant toxicity "therapeutically effective amount".

The effective amount of the agent that increases PTPµ may also be measured directly. The effective amount may be given daily or weekly or fractions thereof. Typically, a pharmaceutical and/or nutraceutical and/or dietary supplement composition of the invention can be administered in an amount from about 0.001 mg up to about 500 mg per kg of body weight per day (e.g., 10 mg, 50 mg, 100 mg, or 250 mg). Dosages may be provided in either a single or multiple dosage regimen. For example, in some embodiments the effective amount is a dose that ranges from about 1 mg to about 25 grams of the anti-scoliosis preparation per day, about 50 mg to about 10 grams of the anti-scoliosis preparation per day, from about 100 mg to about 5 grams of the anti-scoliosis preparation per day, about 1 gram of the anti-scoliosis/GiPCR signaling preparation per day, about 1 mg to about 25 grams of the anti-scoliosis/GiPCR signaling preparation per week, about 50 mg to about 10 grams of the anti-scoliosis/GiPCR signaling preparation per week, about 100 mg to about 5 grams of the anti-scoliosis/GiPCR signaling preparation every other day, and about 1 gram of the anti-scoliosis/GiPCR signaling preparation once a week.

By way of example, a pharmaceutical composition (e.g., containing an agent that increases GiPCR cell signaling in a subject in need thereof, such as an agent which increases PTPµ expression and/or activity or that decreases PIPK1γ expression and/or activity) of the invention can be in the form of a liquid, solution, suspension, pill, capsule, tablet, gelcap, powder, gel, ointment, cream, nebulae, mist, atomized vapor, aerosol, or phytosome. For oral administration, tablets or capsules can be prepared by conventional means with at least one pharmaceutically acceptable excipient such as binding agents, filers, lubricants, disintegrants, or wetting agents. The tablets can be coated by methods known in the art. Liquid preparations for oral administration can take the form of, for example, solutions, syrups, or suspension, or they can be presented as a dry product for constitution with saline or other suitable liquid vehicle before use. Preparations for oral administration also can be suitably formulated to give controlled release of the active ingredients.

In addition, a pharmaceutical (e.g., containing an agent that increases GiPCR cell signaling in a subject in need thereof, such as an agent which increases PTPµ expression or activity or that decreases PIPK1γ expression or activity) composition of the invention can contain a pharmaceutically acceptable carrier for administration to a mammal, including, without limitation, sterile aqueous or non-aqueous solutions, suspensions, and emulsions. Examples of non-aqueous solvents include, without imitation, propylene glycol, polyethylene glycol, vegetable oils, and injectable organic esters. Aqueous carriers include, without imitation, water, alcohol, saline, and buffered solutions. Pharmaceutically acceptable carriers also can include physiologically acceptable aqueous vehicles (e.g., physiological saline) or other known carriers appropriate to specific routes of administration.

An agent that increases GiPCR cell signaling (e.g., that increases PTPµ expression or activity or that decreases PIPK1γ expression or activity) may be incorporated into dosage forms in conjunction with any of the vehicles which are commonly employed in pharmaceutical preparations, e.g. talc, gum arabic, lactose, starch, magnesium stearate, cocoa butter, aqueous or non-aqueous solvents, oils, paraffin derivatives or glycols. Emulsions such as those described in U.S. Pat. No. 5,434,183, may also be used in which vegetable oil (e.g., soybean oil or safflower oil), emulsifying agent (e.g., egg yolk phospholipid) and water are combined with glycerol. Methods for preparing appropriate formulations are well known in the art (see e.g., Remington's Pharmaceutical Sciences, 16th Ed., 1980, A. Oslo Ed., Easton, Pa.).

In cases where parenteral administration is elected as the route of administration, preparations containing agent that increases GiPCR cell signaling (e.g., that increases PTPµ expression or activity or that decreases PIPK1γ expression or activity) may be provided to patients in combination with pharmaceutically acceptable sterile aqueous or non-aqueous solvents, suspensions or emulsions. Examples of non-aqueous solvents are propylene glycol, polyethylene glycol, vegetable oil, fish oil, and injectable organic esters. Aqueous carriers include water, water-alcohol solutions, emulsions or suspensions, including saline and buffered medical parenteral vehicles including sodium chloride solution, Ringer's dextrose solution, dextrose plus sodium chloride solution, Ringer's solution containing lactose, or fixed oils. Intravenous vehicles may include fluid and nutrient replenishers, electrolyte replenishers, such as those based upon Ringer's dextrose, and the like.

These are simply guidelines since the actual dose must be carefully selected and titrated by the attending physician based upon clinical factors unique to each patient or by a nutritionist. The optimal daily dose will be determined by methods known in the art and will be influenced by factors such as the age of the patient and other clinically relevant factors. In addition, patients may be taking medications for other diseases or conditions. The other medications may be continued during the time that the agent that increases GiPCR cell signaling (e.g., that increases PTPμ expression or activity or that decreases PIPK1γ expression or activity) is given to the patient, but it is particularly advisable in such cases to begin with low doses to determine if adverse side effects are experienced.

The present invention also relates to kits. Without being so limited, it relates to kits for stratifying scoliotic subjects and/or predicting whether a subject is at risk of developing a scoliosis comprising an isolated nucleic acid, a protein or a ligand such as an antibody in accordance with the present invention as described above. For example, a compartmentalized kit in accordance with the present invention includes any kit in which reagents are contained in separate containers. Such containers include small glass containers, plastic containers or strips of plastic or paper. Such containers allow the efficient transfer of reagents from one compartment to another compartment such that the samples and reagents are not cross-contaminated and the agents or solutions of each container can be added in a quantitative fashion from one compartment to another. Such containers will include a container which will accept the subject sample (DNA genomic nucleic acid, cell sample or blood samples), a container which contains in some kits of the present invention, the probes used in the methods of the present invention, containers which contain enzymes, containers which contain wash reagents, and containers which contain the reagents used to detect the extension products. Kits of the present invention may also contain instructions to use these probes and or antibodies to stratify scoliotic subjects or predict whether a subject is at risk of developing a scoliosis.

The articles "a," "an" and "the" are used herein to refer to one or to more than one (i.e., to at least one) of the grammatical object of the article.

The term "including" and "comprising" are used herein to mean, and re used interchangeably with, the phrases "including but not limited to" and "comprising but not limited to".

The terms "such as" are used herein to mean, and is used interchangeably with, the phrase "such as but not limited to".

The term "about" is used to indicate that a value includes the standard deviation of error for the device or method being employed to determine the value. In general, the terminology "about" is meant to designate a possible variation of up to 10%. Therefore, a variation of 1, 2, 3, 4, 5, 6, 7, 8, 9 and 10% of a value is included in the term "about".

The present invention is illustrated in further details by the following non-limiting examples.

EXAMPLE 1

Materials and Methods

Patient Recruitment

The Institutional Review Board of the Sainte-Justine Hospital, Montreal, Quebec approved this study. Parents or legal guardians of all participants gave their written informed consent, and minors gave their assent. An orthopedic surgeon at the Saint-Justine Children's hospital clinically assessed each patient, and all bone biopsies were collected during corrective surgeries.

TABLE II

Clinical data of patients used to test PTPμ and PIPKγ, by qPCR and Western Blot.

| Patient Number | Gender | Age | Diagnosis | Cobb Angle | Type of Curvature | Pain | Family History of Scoliosis | Medical History | Group |
|---|---|---|---|---|---|---|---|---|---|
| T-26 | Male | 14.6 | Trauma | N/A | N/A | No | N/A | N/A | Control |
| T-29 | Male | 15.8 | Trauma | N/A | N/A | No | N/A | N/A | Control |
| T-32 | Female | 8.8 | Trauma | N/A | N/A | No | N/A | N/A | Control |
| T-22 | Female | 14.0 | Trauma | N/A | N/A | No | N/A | N/A | Control |
| T-8 | Female | 15.1 | Trauma | N/A | N/A | No | N/A | Osteochondrosis | Control |
| T-19 | Female | 15.5 | Trauma | N/A | N/A | No | N/A | Clubfoot | Control |
| T-34 | Male | 14.1 | Trauma | N/A | N/A | No | N/A | N/A | Control |
| T-44 | Male | 12.6 | Trauma | N/A | N/A | No | N/A | N/A | Control |
| T-18 | Female | 19.0 | Trauma | N/A | N/A | No | N/A | N/A | Control |
| T-51 | Female | N/A | Trauma | N/A | N/A | No | N/A | N/A | Control |
| T-41 | Male | 17.2 | Trauma | N/A | N/A | No | N/A | N/A | Control |
| T-14 | Female | 11.6 | Trauma | N/A | N/A | No | N/A | N/A | Control |
| T-2 | Female | 14.1 | Trauma | N/A | N/A | No | N/A | N/A | Control |
| T-11 | Female | 15.7 | Trauma | N/A | N/A | No | N/A | N/A | Control |
| T-20 | Female | 18.7 | Trauma | N/A | N/A | No | N/A | N/A | Control |
| T-1 | Female | 15.9 | Trauma | N/A | N/A | No | N/A | N/A | Control |
| T-13 | Female | 18.7 | Trauma | N/A | N/A | No | N/A | N/A | Control |
| 1075 | Female | 13.1 | AIS | 59-73 | rTIL | No | Aunt, uncle | N/A | 1 |
| 1032 | Female | 11.4 | AIS | 62-47 | rTIL | No | N/A | N/A | 1 |
| 1038 | Female | 17.2 | AIS | 47 | ITL | No | N/A | N/A | 1 |
| 1267 | Male | 14.6 | AIS | 54 | rTL | No | mother | N/A | 1 |
| 1388 | Female | 14.6 | AIS | 46 | rTL | No | N/A | N/A | 1 |
| 1025 | Female | 15.3 | AIS | 53-42 | rTIL | No | N/A | N/A | 1 |
| 1090 | Female | 18.0 | AIS | 45-57 | rTIL | Yes | Half-sister, mother | Atrial Septal Defect, Asthma, Tonsillectomy | 1 |
| 1423 | Female | 14.6 | AIS | 73-45 | rTIL | Yes | N/A | N/A | 1 |
| 1237 | Female | 11.7 | AIS | 63 | rT | No | N/A | N/A | 1 |
| 1061 | Male | 12.8 | AIS | 75 | rT | No | N/A | Syringomyelia | 1 |
| 1012 | Female | 11.8 | AIS | 74-56 | rTIL | No | N/A | N/A | 1 |
| 1266 | Male | 15.6 | AIS | 52 | rT | Yes | N/A | N/A | 1 |
| 1282 | Female | 16.4 | AIS | 49 | rTL | Yes | N/A | N/A | 2 |

TABLE II-continued

Clinical data of patients used to test PTPµ and PIPKγ, by qPCR and Western Blot.

| Patient Number | Gender | Age | Diagnosis | Cobb Angle | Type of Curvature | Pain | Family History of Scoliosis | Medical History | Group |
|---|---|---|---|---|---|---|---|---|---|
| 1081 | Female | 13.6 | AIS | 60 | ITL | Yes | N/A | N/A | 2 |
| 1391 | Female | 15.0 | AIS | 54 | IL | Yes | N/A | Hemivertebra Surgery | 2 |
| 1418 | Female | 13.1 | AIS | 41 | rT | No | N/A | Mental Retardation, Epilepsy | 2 |
| 1066 | Female | 17.3 | AIS | 53 | rT | No | Aunt | Myasthenia gravis | 2 |
| 1063 | Female | 14.8 | AIS | 67 | rT | Yes | N/A | N/A | 2 |
| 1013 | Female | 15.0 | AIS | 54 | rT | Yes | Aunt, mother | N/A | 2 |
| 1060 | Female | 14.4 | AIS | 53-55 | rTIL | No | Grandmother | Tonsillectomy, Adenoidectomy | 2 |
| 1042 | Female | 14.2 | AIS | 70-48 | rTIL | No | Brother, mother | N/A | 2 |
| 1112 | Female | 13.3 | AIS | 58-49 | rTIL | No | Aunt | Chiari, Syringomyelia, Asthma | 2 |
| 1020 | Female | 13.3 | AIS | 59-57 | rTIL | Yes | N/A | N/A | 3 |
| 1143 | Female | 16.9 | Neurological Scoliosis | 83 | rT | No | N/A | Spina Bifida, Chiari, Strabismus Surgery | 3 |
| 1071 | Female | 15.9 | AIS Kyphosis | 57-60 | rTIL | Yes | N/A | Septal Surgery | 3 |
| 1373 | Female | 14.6 | AIS | 41-48 | rTIL | Yes | N/A | Concussion (3 years old) | 3 |
| 1036 | Female | 13.0 | AIS | 57 | rT | No | N/A | N/A | 3 |
| 1003 | Male | 18.0 | AIS | 64-54 | rTIL | No | N/A | Asthma | 3 |
| 1064 | Female | 15.2 | AIS | 90-90 | rTIL | No | N/A | Elbow fracture | 3 |
| 1665 | Female | 12.6 | AIS | 28-58-21 | rTITIL | Yes | N/A | N/A | 3 |
| 1653 | Female | 11.2 | JIS | 68 | rT | Yes | Mother | Asthma, Epistaxis | 3 |
| 1439 | Female | 17.7 | AIS | 69 | rT | Yes | Mother | N/A | 3 |
| 1058 | Female | 14.4 | AIS | 90-66 | rTIL | Yes | N/A | N/A | 3 |

Experimental Animal Models

The Institutional Review Board for the care and handing of animals used in research (CHU Sainte-Justine) has approved the protocol in accordance with the guidelines of the Canadian Council of Animal Care.

The bipedal mouse models have been generated as described by Oyama et al. (2006). Amputation of the fore-limbs and tail was performed under anesthesia after weaning (5-weeks after birth), as reported by Oyama et al. (2006) and (Machida et al., 2006). A Faxitron™ X-ray instrument (Faxitron™ MX20- Faxitron Co., Arizona, USA) was used to image and examine the spine of these mice monthly post-weaning, up until their sacrifice at nine months of age. Bipedal surgeries were performed on 120 mice from each wild type and PTPµ knockout (a gift from Dr. Gebbink M F, Laboratory of Thrombosis and Haemostasis, Department of Clinical Chemistry and Haematology, University Medical Center Utrecht, Heideberglaan 100, 3584 CX Utrecht, The Netherlands).

Derivation of Primary Osteoblast Cultures

In human subjects, primary osteoblast cell cultures were derived from AIS and control patient biopsies that were obtained intra-operatively. For AIS patients, bone specimens were obtained intra-operatively from vertebrae (varying from T3 to L4 according to the surgical procedure performed), while with trauma cases (used as non-scoliotic controls), bone specimens were obtained from other anatomical sites (tibia, femur or iliac crest).

Bone specimens from mice were obtained from the spine after euthanasia. Bone fragments were reduced to smaller pieces with a cutter in sterile conditions. The small bone pieces were incubated in αMEM medium containing 10% fetal bovine serum (FBS; certified FBS, Invitrogen, Burlington, ON, Canada) and 1% penicillin/streptomycin (Invitrogen) at 37° C. in 5% $CO_2$, in a 10-cm² culture dish. After one month, osteoblasts emerging from the bone pieces were separated from the remaining bone fragments by trypsinization. RNA was extracted from the osteoblasts using the TRIzol™ method, (Invitrogen). Expression profiles of the PTPµ and PIPK1γ genes were studied by qPCR. Transcript expression was assessed with the Stratagene™ Mx3000P (Agilent Technologies, La Jolla, Calif.).

Quantitative Reverse Transcription-polymerase Chain Reaction (qPCR)

Thermo-Script™ reverse transcriptase (Invitrogen) was used to reverse mRNA into cDNA (1 mg total concentration). Several dilutions were tested to choose the concentration that yielded the most efficient amplification. The human primers used were the following:

```
β-actin forward
                                          (SEQ ID NO: 1)
5'-GGAAATCGTGCGTGACAT-3', β-actin reverse
                                          (SEQ ID NO: 2)
5'-TCATGATGGAGTTGAAGGTAGTT-3', PTPµ forward
                                          (SEQ ID NO: 3)
5'-GGCCGGACTTTTGCTAACT-3', PTPµ reverse
                                          (SEQ ID NO: 4)
5'-TGTGCTATACGGCTCATCAAA-3',
```

-continued

CD44 forward
(SEQ ID NO: 5)
5'-AGCATCGGATTTGAGACCTG-3',

CD44 reverse
(SEQ ID NO: 6)
5'-TGAGTCCACTTGGCTTTCTG-3',

β1 integrin forward
(SEQ ID NO: 7)
5'-ATGTGTCAGACCTGCCTTG-3',

β1 integrin reverse
(SEQ ID NO: 8)
5'-TTGTCCCGACTTTCTACCTTG-3',

β3 integrin forward
(SEQ ID NO: 9)
5'-GGAAAGTCCATCCTGTATGTGG-3',

β3 integrin reverse
(SEQ ID NO: 10)
5'-GAGTTTCCAGATGAGCAGGG-3',

αv integrin forward
(SEQ ID NO: 11)
5'-GTCCCACAGTAGACACATATG-3',

αv integrin reverse
(SEQ ID NO: 12)
5'-TCAACTCCTCGCTTTCCATG-3',

α1 integrin forward
(SEQ ID NO: 13)
5'-GACATTTGGATGAACTTTAGTCACC-3',

α1 integrin reverse
(SEQ ID NO: 14)
5'-GGCAATGGAATTCACGACTTG-3',

α4 integrin forward
(SEQ ID NO: 15)
5'-GGATGAGACTTCAGCACTCAAG-3',

α4 integrin reverse
(SEQ ID NO: 16)
5'-GGTGAAATAACGTTTGGGTCTTTG-3',

β3 integrin forward
(SEQ ID NO: 17)
5'-GGAAAGTCCATCCTGTATGTGG-3',

β3 integrin reverse
(SEQ ID NO: 18)
5'-GAGTTTCCAGATGAGCAGGG-3',

β5 integrin forward
(SEQ ID NO: 19)
5'-CTTGCACTCCTGGCTATCTG-3',

β5 integrin reverse
(SEQ ID NO: 20)
5'-TGCGTGGAGATAGGCTTTC-3',

β8 integrin forward
(SEQ ID NO: 21)
5'-GATTGGGTTGCTTAAAGTCCTG-3',

β8 integrin reverse
(SEQ ID NO: 22)
5'-GGTAGGTGACTGCT CTTGTG-3',

PIPK1γ forward
(SEQ ID NO: 23)
5'-CAGATTACAGTGCAGGTGGAG-3',

PIPK1γ reverse
(SEQ ID NO: 24)
5'-GCTGGCAGTTTCTACTTCAAC-3'.

Each amplification was performed in duplicate using 5 ml of diluted cDNA, 7.5 ml of 3 mM primer solution and 12.5 nm of 2× QuantiTect™ SYBR Green PCR Master Mix (QIAGEN Inc, Ontario, Canada). All reaction mixes were run on Mx3000P system from Stratagene (Agilent Technologies Company, La Jolla, Calif.) and analyzed with MxPro™ QPCR Software also from Stratagene. Relative quantification was calculated with the delta CT method using β-actin as the endogenous control.

Isolation of Plasma Membrane (PM) Proteins from Cell Culture

Osteoblasts from human subjects were washed 3 times with cold PM (plasma membrane) buffer [0.25 M Sucrose, 1 mM EDTA and 20 mM Tricine] and 2 ml of cold PMC buffer (PM buffer plus 1× protease inhibitors, 1 mM PMSF, 0.4 mM Sodium Orthovanadate) was added. The cells were scraped from the petri dishes and centrifuged at 1000×g for 5 min. The pellet (5 cm) was dissolved in 600 µl of cold PMC buffer. The pellet was then homogenized using ceramic beads (Precelys™) 3×5500×g for 20" with 2 min between each cycle, and then centrifuged at 1000×g for 10 min at 4° C. The Post-Nuclear Supernatant (PNS) was kept on ice. The pellet was resuspended in 300 µl PMC buffer, the homogenization step was repeated once more and then centrifuged at 1000×g for 10 min at 4'C. The protein concentration was measured; PNS was layered on the top of 15 ml of 30% percoll with PMC buffer (in 25×89 mm tubes). The samples were centrifuged in a fixed angle rotor at 84,000×g (50.2 Ti rotor) for 30 min at 4° C. PM fraction was visible as a band at a distance of 5.7 cm from the bottom of tube. To remove any trace of percoll, the samples were centrifuged in a S45-A rotor in a sorval M150 micro-ultracentrifuge at 105,000×g (TLA100.4 rotor) for 90 min. A tightly packed pellet was formed by the percoll and PM fraction was carefully removed and stored at −80° C. for immunoprecipitation and western blot methods. The concentration of protein was measured using, Protein Bio Rad, (Bio-Rad laboratories, California, U.S.A).

Immunoprecipitation and Western Blot

A pre-clearing step was done to reduce the non-specific binding of proteins to agarose or sepharose beads. Briefly, 25 µl of protein sepharose (A) beads (GE Healthcare Bioscience AB, Canada) were added to the PM protein solution (1.5 mg). The mix was incubated for 30 minutes at 4° C. with gentle agitation. The solution was then centrifuged at 16,200×g at 4° C. for 1 minute. The pellet was discarded and the supernatant was kept for immunoprecipitation. To immunoprecipitate the PTPµ 1 µg of anti-PTPµ antibody (SC-25433), (Santa Cruz Biotechnology Inc., Santa Cruz, Calif.)/1 mg protein was added. The sample was incubated with the antibody overnight at 4° C. with agitation. To each sample, 50 µl of protein sepharose (A) beads were added and then mixed gently using wide-mouthed pipette tips. The lysate-beads mixture was incubated at 4° C. with agitation for 2 hours. After incubation the tubes were centrifuged, the supernatant was removed and the beads were washed in PM buffer three times (each time centrifuging at 4° C. and removing the supernatant). Finally, the supernatant was removed and 50 µl of 3× loading (Laemmli) buffer was added. Samples were boiled at 100° C. for 5 minutes to denature the protein and separate it from the beads, then samples were centrifuged and the supernatant was kept for the protein marker. Samples were subjected to 5%-12% gradient SDS-PAGE, transferred to PVDF (polyvinylidene fluoride) membrane and immunoblotted using anti-PTPµ anti-mouse (1:500 dilution of primary antibodies; Santa Cruz Biotechnology Inc., Santa Cruz, Calif.; 1:10,000 dilution of horseradish peroxidase-conjugated secondary antibodies, BioSource Inc. Camarillo, Calif.). Reactive bands were visualized using an enhanced chemiluminescent kit (BM Chemiluminescent blotting substrate POD) according to the manufacturer's specifications (Roche Diagnostic Corp., Indianapolis, Ind.). The same protocol was used to immunoprecipitate PIPK1γ. Mouse anti-PIPK1γ (H-9, #sc-377061 from Santa Cruz) which recognizes mouse, rat and human PIPK1γ and Anti-phosphotyrosine antibody [PY20] (#ab10321, from abcam) were used.

Similarly, in order to validate the interaction between OPN and its cognate receptors, the different receptors for OPN were immunoprecipitated using different antibodies. For each receptor 1 µg was added per 1 mg protein these antibodies, integrin β1 (SC-6622), integrin β3 (SC-6627), integrin β5 (SC-5401), integrin α4 (sc-6589), integrin α5 (sc-166681), integrin α8 (sc-30983) (Santa Cruz Biotechnology Inc., Santa Cruz, Calif.) and integrin αv (4711) (Cell signaling technology, Ontario, Ca). This immunoprecipitation was followed by Western blot using anti-OPN anti mouse (1/2000) (courtesy of Dr. Marc D. McKee, McGill University). The previous antibodies were used for Western blot detection (1/1000).

Analysis of G protein Signaling

The signaling capacity of G proteins was assessed from osteoblast cultures using cellular dielectric spectroscopy (CDS) performed on a CellKey™ apparatus (MDS Sciex, San Francisco, Calif.), as described in Akoume, et al., 2010 and WO 2010/040234, 2010 to Moreau et al. To assess GiPCR cell signaling, specific agonists that bind to GiPCR and regulate Gi proteins were used: Apelin-17, Oxymethazolin and Somatostatin (Som) (Tocris Bioscience, Canada).

Furthermore, Pertussis toxin (PTX) (Sigma Aldrich, Canada) was used to determine if the effect of the agonists was related to G αi proteins. This toxin is produced by *Bordetella pertussis* and it catalyzes the adenosine diphosphate (ADP)-ribosylation of some G-proteins at a cysteine residue near the C-terminus resulting in uncoupling of receptor and G-protein.

Cell Lines and siRNA Transfection

Primary osteoblast cell cultures from C57Bl/6j WT and C57B/6j PTPμ$^{-/-}$ were cultured (as described above). Lipofectamine™ RNAiMAX (Invitrogen) was applied for siRNA transfection according to the manufacturer's instructions. The sequence of RNA oligo used for the knockdown of OPN is (CCA CAG CCA CAA GCA GUC CAG AUU A (SEQ ID NO: 25)). The cells were harvested for RNA extraction after 48 hrs. The same procedure was followed for phosphatidylinositol-phosphate kinase type I gamma (PIPK1γ). The sequence of RNA oligo used for the knockdown of PIPK1γ is (CCU CCA CAU CGG GAU UGA UAU U (SEQ ID NO: 26)).

Osteopontin Immunosorbent Assays

Peripheral blood samples from mice were collected in EDTA-treated tubes and then centrifuged. Derived plasma samples were aliquoted and kept frozen at −80° C. until thawed and analyzed. Plasma concentrations of OPN were measured by capture enzyme-inked immunosorbant assays (ELISA) according to protocols provided by the manufacturer (IBL, Hamburg, Germany). The OPN ELISA kit measures total concentration of both phosphorylated and non-phosphorylated forms of OPN in plasma. All ELISA tests were performed in duplicate and reading were performed at 450 nm using a DTX880 microplate reader (Beckman Coulter, USA).

Statistical Analysis

Data are presented as mean±SE, and were analyzed by ANOVA or Students t test using GraphPad™ Prism 4.0 software. Multiple comparisons of means were performed with one-way ANOVA followed by a post-hoc test of Dunnett. Only P values <0.05 were considered significant.

EXAMPLE 2

Lack of PTPμ Influences the Nature of Scoliosis Associated with High Plasma OPN in Bipedal Mice Amputation of forelimbs and tails induces scoliosis in mice after 40 weeks of bipedal ambulation [16, 15] and increases their plasma OPN levels. Consistent with this approach, scoliosis was induced in female wild type (WT) and PTPμ knockout (PTPμ$^{-/-}$) mice to examine the impact of PTPμ deficiency on the development of scoliosis under high plasma OPN conditions. Measurements of OPN in plasma from PTPμ$^{-/-}$ mice were performed each 12 weeks during the experimental period. Results presented in FIG. 1-A, have revealed no significant difference in plasma OPN level between normal scoliotic C57Bl/6 bipedal mice and PTPμ scoliotic ones. At all time points, levels of plasma OPN in WT and PTPμ$^{-/-}$ mice were similar. Of all mice examined by radiography at the final time point 36$^{th}$ postoperative week, lateral curvature was apparent in 55% of WT and 85% of PTPμ$^{-/-}$ mice, indicating a higher incidence of scoliosis in PTPμ$^{-/-}$ than in WT mice (FIG. 1-B). The lateral curvature was also more pronounced in PTPμ$^{-/-}$ mice, as illustrated by representative radiographs in FIGS. 1-C and D, suggesting that scoliosis is more severe in PTPμ$^{-/-}$ than in WT mice. These data emphasize that lack of PTPμ exacerbates spinal deformity progression and support a ink between development of scoliosis and high plasma OPN in bipedal mice.

EXAMPLE 3

Lack of PTPμ Amplifies the Defective GiPCR Signaling in Bipedal Mice

Evidences for the occurrence of defective GiPCR signaling in bipedal mice was demonstrated by a reduced ability of various GiPCR selective agonists to promote cell signaling as measured by CDS (WO 2010/040234 Moreau et al.). To examine the impact of PTPμ deficiency on this defect, osteoblasts from bipedal WT and PTPμ$^{-/-}$ mice were screened for their response to three GiPCR selective agonists identified in (FIG. 2). In agreement with previous results (Akoume et al Spine 2010), all three compounds evoked typical CDS response profiles of GiPCR in WT osteoblasts. Consistent with Gi coupling for their cognate receptors in these cells, response to each of the three tested compounds was blocked by pre-treatment with PTX (FIGS. 2 A-F). Similar results were obtained with PTPμ$^{-/-}$ osteoblasts (FIGS. 2 G-L). Results illustrated in FIG. 3 show that all three compounds increased response in a concentration-dependent manner in osteoblasts from WT and PTPμ$^{-/-}$ mice. However, in each case, osteoblasts from PTPμ$^{-/-}$ mice were less responsive than those from WT mice, but EC50 values were similar in both groups (FIGS. 3 A-C). These results suggest that lack of PTPμ affects Gi protein activity independently of the receptor.

EXAMPLE 4

Lack of PTPμ Amplifies Inhibitory Effect of OPN on GiPCR Signaling—OPN Silencing To relate these findings to the OPN action, the small interference RNA (siRNA) approach was used to knockdown the expression of OPN in WT and PTPμ$^{-/-}$ osteoblasts. The efficiency of siRNA in these osteoblasts was demonstrated by qPCR and Western blot analysis (FIGS. 3 D and E). It was found that the deletion of OPN enhanced response to GiPCR stimulation in WT and PTPμ$^{-/-}$ osteoblasts and abrogated the difference in the degree of their responses (FIGS. 3 F-H). These results support a role for OPN in the defective GiPCR signaling in bipedal mice and suggest that lack of PTPμ exacerbates the inhibitory effect of OPN on GiPCR signaling.

EXAMPLE 5

Figure 4A:
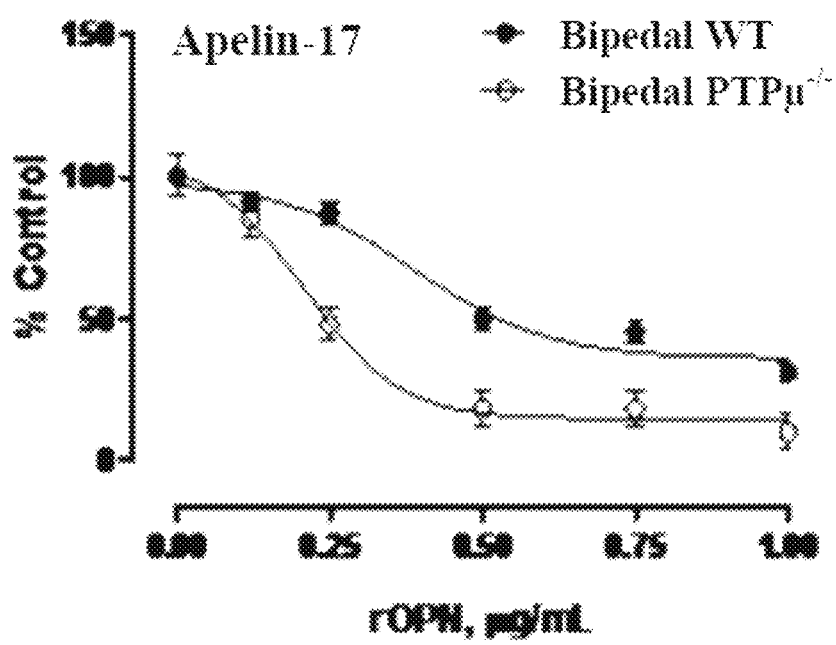
FIGS. 4A-C shows that the lack of PTPµ exacerbates the defective GiPCR signaling caused by OPN.
Figure 4B:
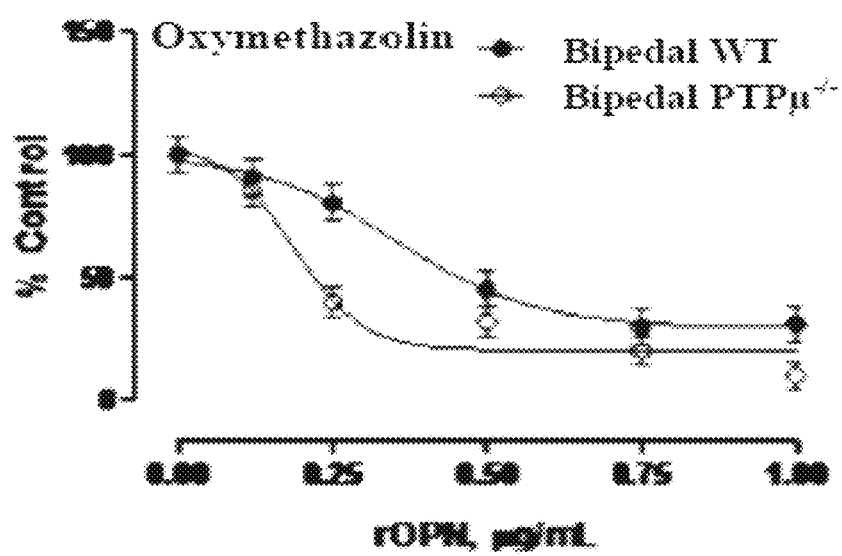
Figure 4C:
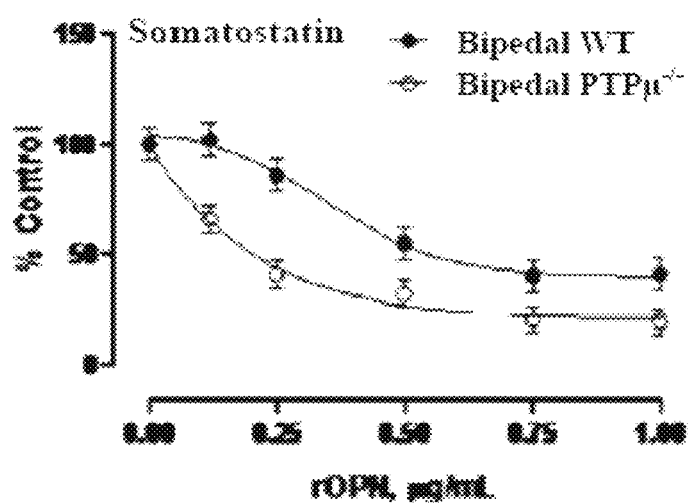

Lack of PTPμ Amplifies Inhibitory Effect of OPN on GiPCR Signaling—Exogenous OPN WT and PTPμ$^{-/-}$ osteoblasts were treated with varying concentrations of exogenous recombinant OPN (rOPN) prior to GiPCR stimulation with agonists identified in FIGS. 4 A-C. In each case, rOPN caused decrease in the integrated response in a concentration-dependent manner, as well in WT as in PTPμ$^{-/-}$ osteoblasts. However, IC50 values were lower in PTPμ$^{-/-}$ compared to WT osteoblasts, suggesting that osteoblasts from PTPμ$^{-/-}$ mice are more sensitive to the inhibitory effect of OPN on GiPCR signaling.

EXAMPLE 6

Lack of PTPμ does not Influence Integrin Expression in Osteoblasts

Figure 5A:
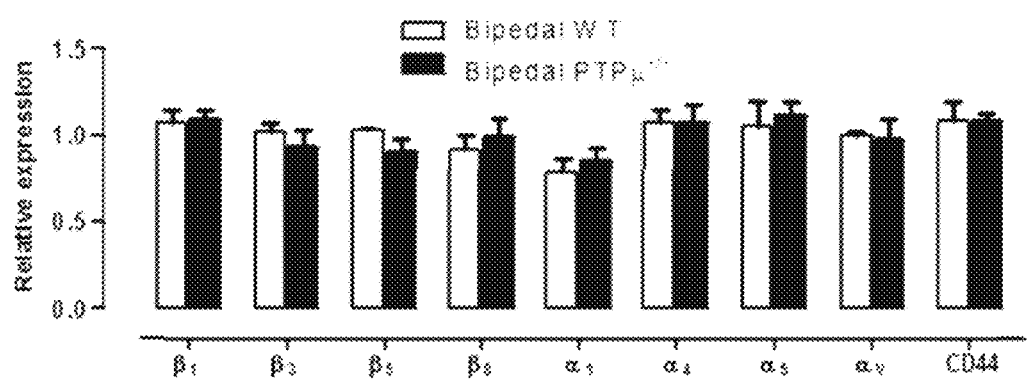
FIGS. 5A-C shows that lack of PTPµ influences the interaction of OPN with integrin in osteoblasts.
Figure 5B:
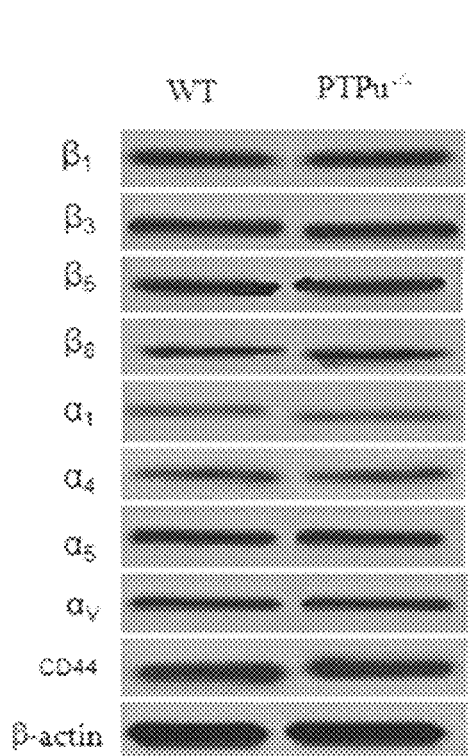

OPN interacts with various receptors including receptors expressed by osteoblasts: $\alpha_v\beta_1$, $\alpha_v\beta_3$, $\alpha_v\beta_5$, $\alpha_4\beta_1$, $\alpha_5\beta_1$ and $\alpha_8\beta_1$ integrins and CD44[17, 18, 19, 20, 21, 22]. It was of interest to examine which receptors are responsible for the effects associated with PTPμ deficiency. For this purpose, the expression levels of these receptors were examined, using a qPCR analysis. As illustrated in FIG. 5A, no significant difference in expression of integrin at the mRNA levels was found between WT and PTPμ$^{-/-}$ osteoblasts. Similar profiles were obtained when protein levels of these receptors were determined by Western blot (FIG. 5B). These results exclude the possibility that the effects associated with PTPμ deficiency implicate changes in receptor expression.

EXAMPLE 7

Lack of PTPμ Influences the Interaction of OPN with Integrin in Osteoblasts

Figure 5C:
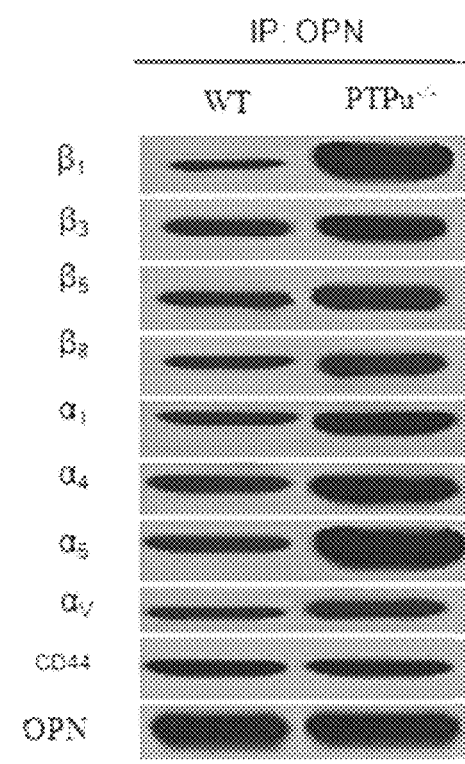

Then, was examined whether the interaction of OPN with the receptor is influenced by PTPμ deficiency. For this purpose, cell lysates from WT and PTPμ osteoblasts were immunoprecipitated with antibodies against various OPN receptors and the interaction with OPN was revealed by Western blot using antibody specific for OPN (FIG. 5C). Results showed that OPN was co-immunoprecipitated with all receptors in WT and PTPμ$^{-/-}$ osteoblasts. However, levels of $\beta_1$ and $\alpha_5$ integrins in the OPN immunoprecipitates were increased by more than 30-fold in PTPμ$^{-/-}$ osteoblasts compared to WT osteoblasts, while there was only a moderate difference (0.8- to 2.3-fold) in the levels of other integrins between both cell groups. In contrast, levels of CD44 in OPN immunoprecipitates were similar in WT and PTPμ$^{-/-}$ osteoblasts. These results suggest that loss of PTPμ favours the interaction of OPN with integrins in osteoblasts and indicate that $\alpha_5\beta_1$ integrin is possibly the most promising receptor responsible for the effects associated with PTPμ deficiency.

EXAMPLE 8

Silencing of PIPK1γ Selectively Enhances GiPCR Signaling in PTPμ$^{-/-}$ Osteoblasts To understand the molecular basis of the interaction of OPN with integrin in the absence of PTPμ, PIPK1 was examined because the catalytic activity of PIPK1γ by tyrosine phosphorylation is essential for enhancing the affinity of integrin for ligands, and this enzyme has been shown to be dephosphorylated by PTPμ$^{-/-}$. Therefore, it was examined whether loss of PTPμ amplifies the reduction in GiPCR signaling through the sustained activation of PIPK1γ. The phosphorylation status of PIPK1γ in WT and PTPμ$^{-/-}$ osteoblasts was first examined.

Figure 6A:
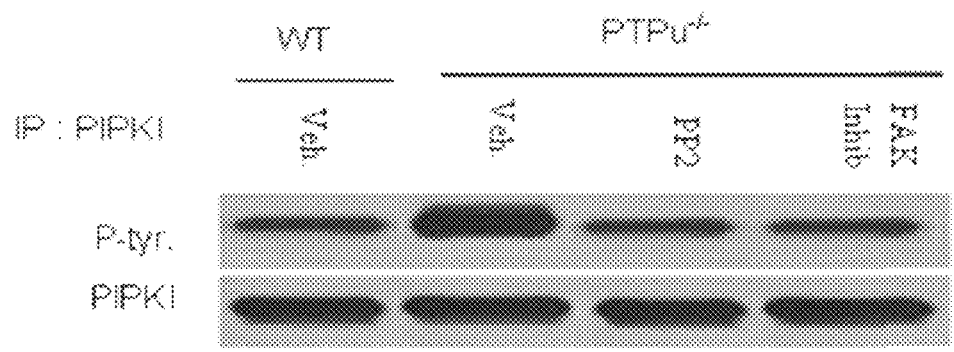
FIGS. 6A-H shows that silencing of PIPK1γ selectively enhances GiPCR signaling in PTPµ$^{-/-}$ osteoblasts.
Figure 6B:
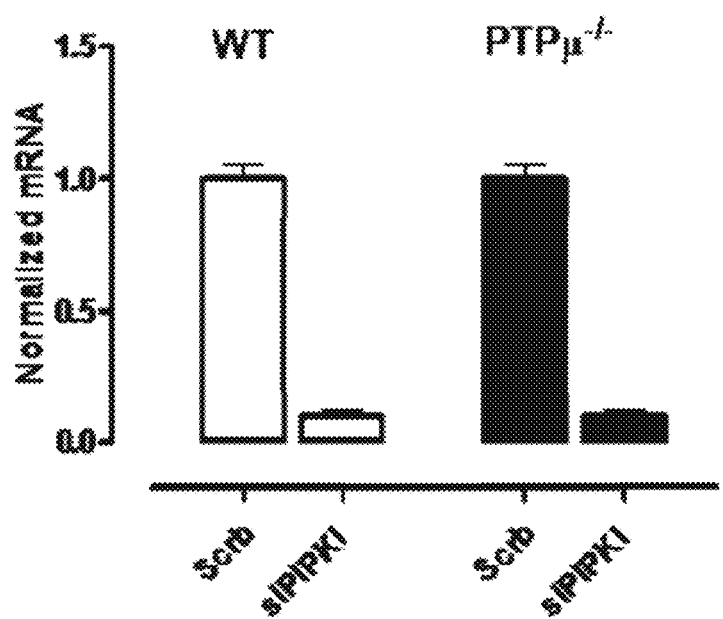
Figure 6C:
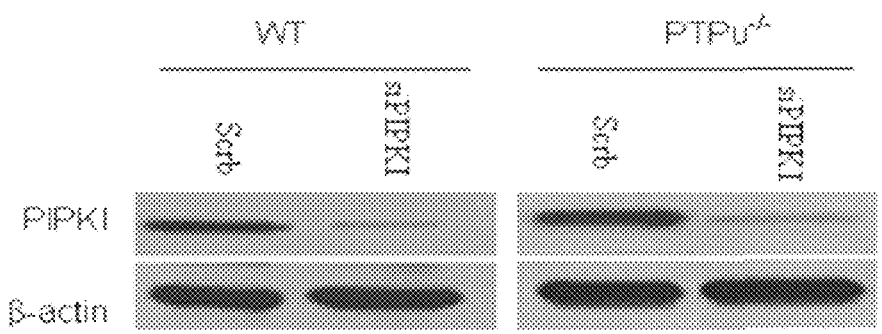
Figure 6D:
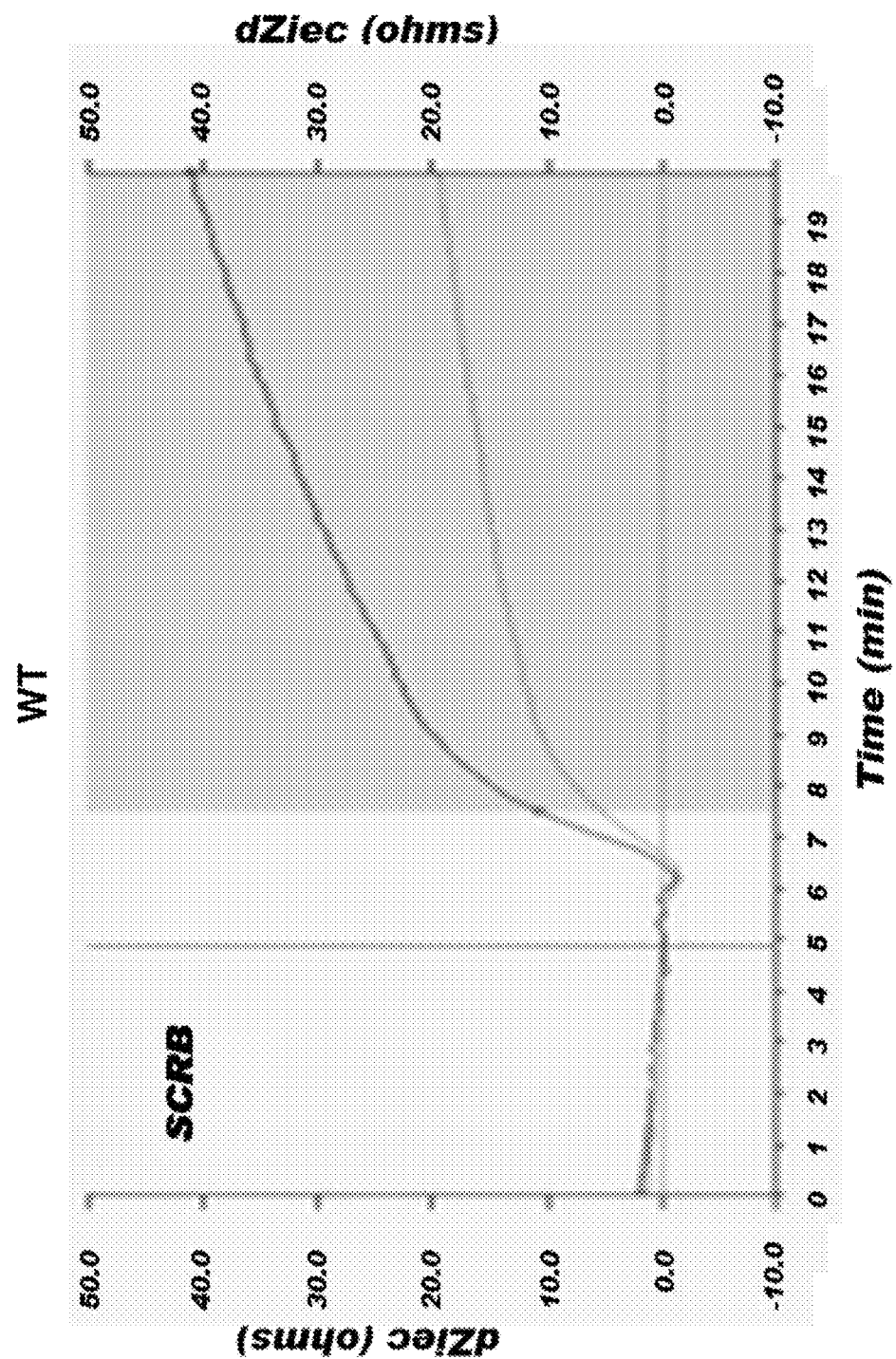
Figure 6E:
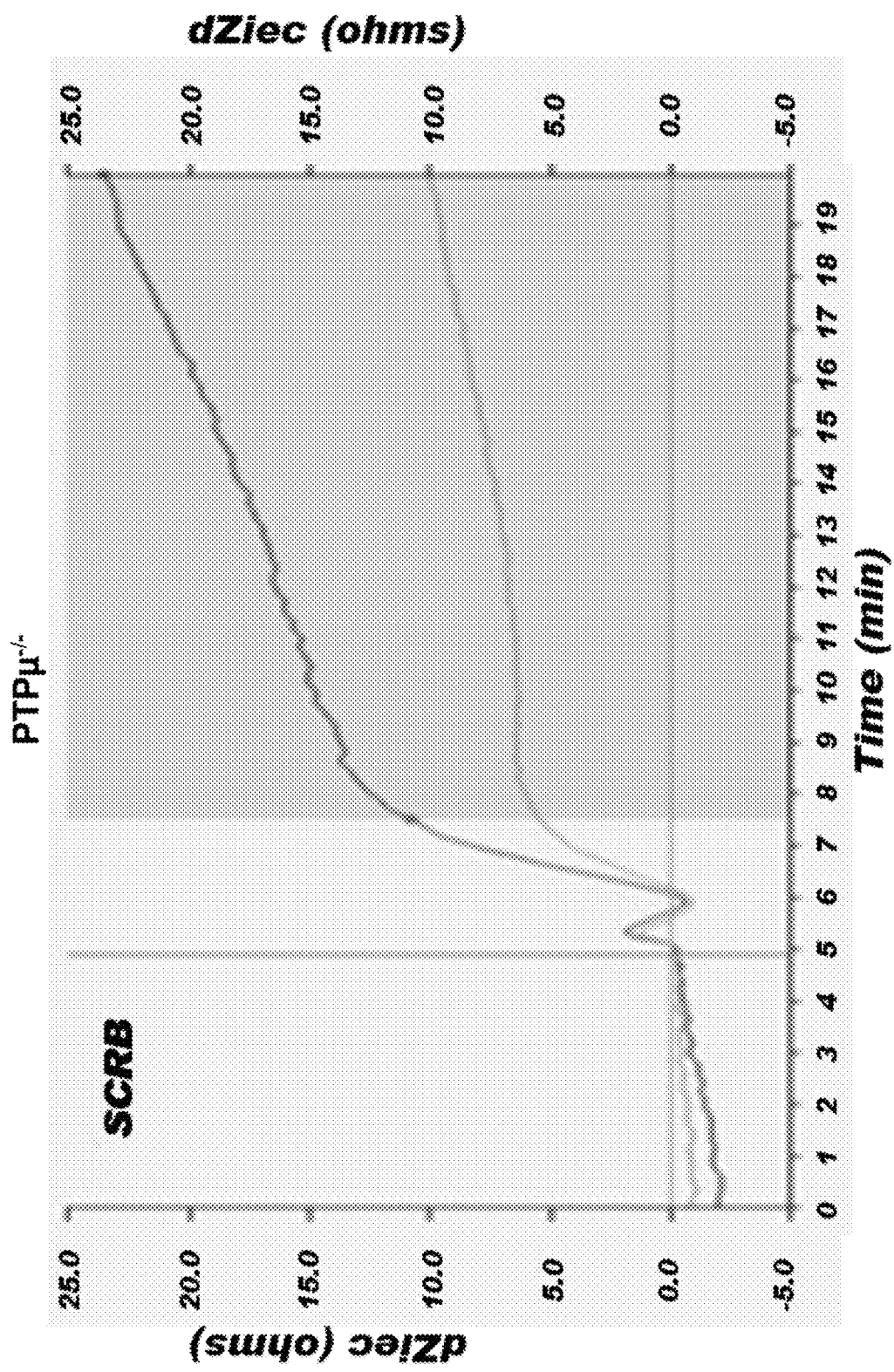
Figure 6F:
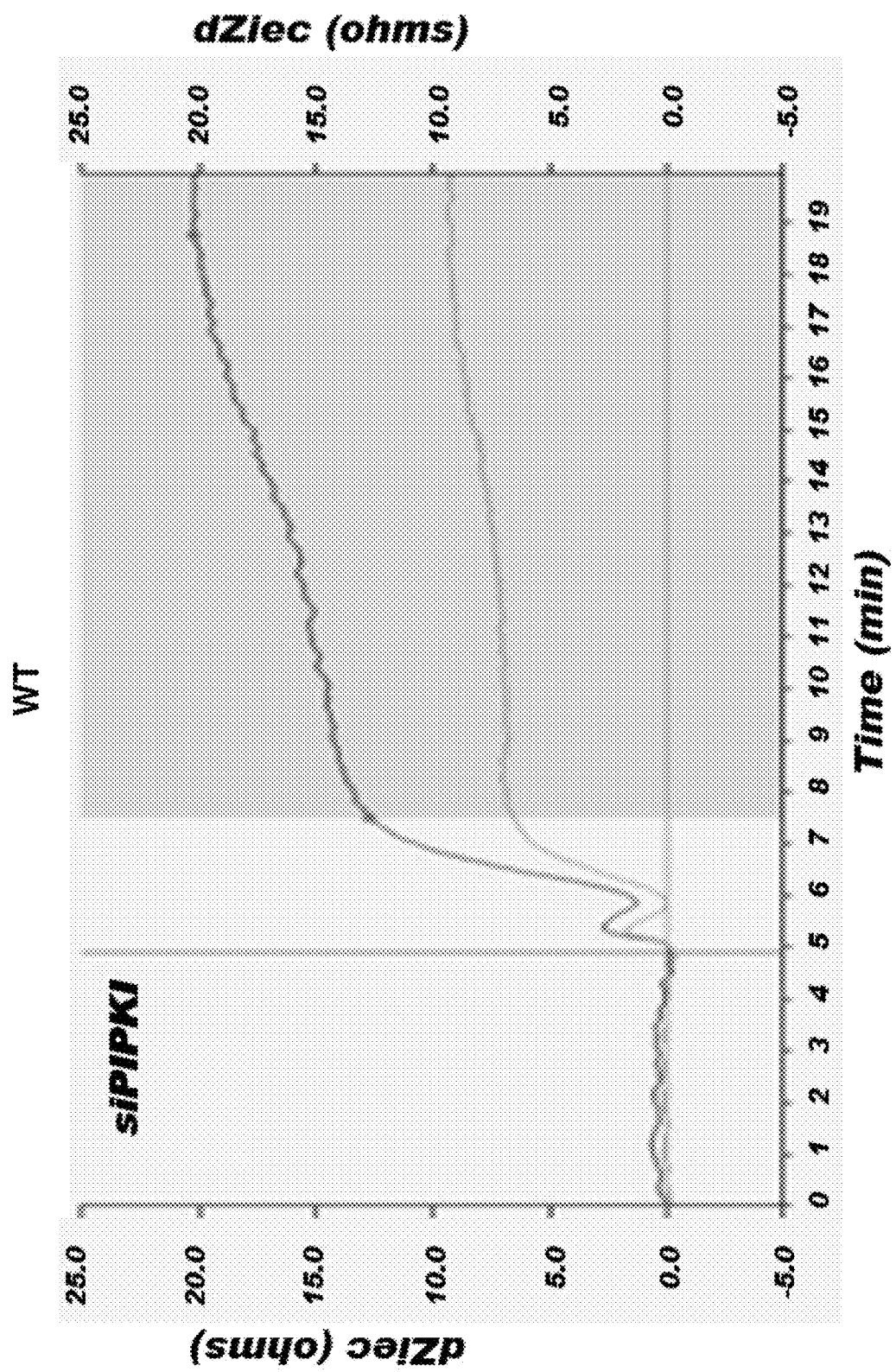
Figure 6G:
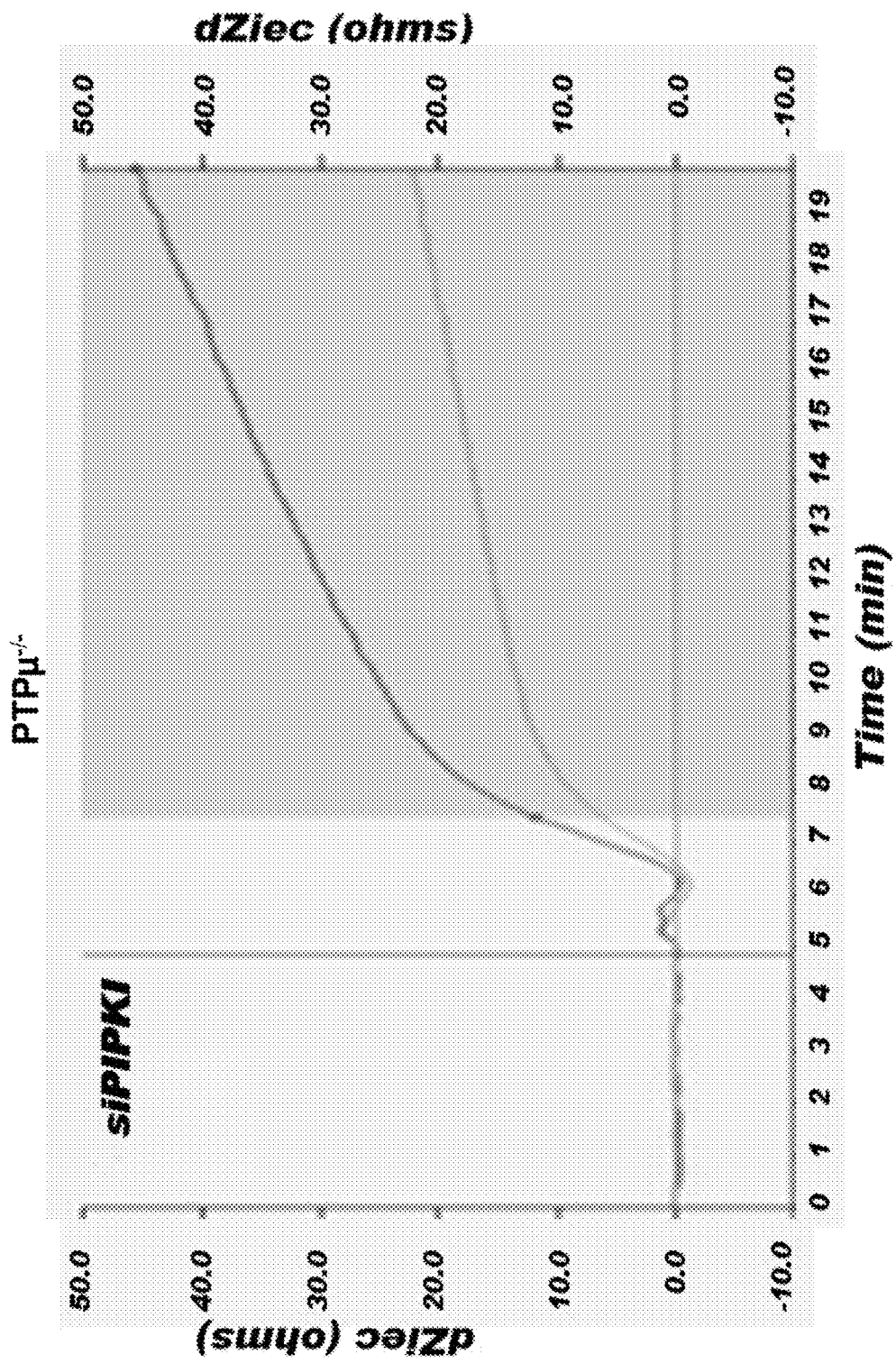

Cell lysates were immunoprecipitated with PIPK1γ antibody and probed with phospho-tyrosine antibody. Phosphorylation levels of PIPK1γ were higher in osteoblasts from PTPμ$^{-/-}$ than in those from WT mice (compare P-tyr row in columns Wt vehicle vs. PTPμ$^{-/-}$ vehicle), while levels of PIPK1γ total form (i.e. phosphorylated and unphosphorylated) were comparable between both phenotypes (compare PIPK1 row in columns Wt vehicle vs. PTPμ$^{-/-}$ PP2 or Fak inhibitor) (FIG. 6A).

EXAMPLE 9

Inhibiting FAK and Src Decreases PIPK1γ Phosphorylation

It was then examined whether Focal Adhesion Kinase (FAK) and C sarcoma tyrosine kinase (Src) are responsible for the increased phosphorylation of PIPK1γ observed in osteoblasts from PTPμ$^{-/-}$ mice. Cells were treated with inhibitors of Src (PP2) and FAK (inhibitor-14) prior to immunoprecipitation assay. As expected, levels of PIPK1γ phosphorylation were attenuated by both treatments (FIG. 6A). This suggests that the activity of PIPK1γ is abnormally elevated in osteoblasts from PTPμ$^{-/-}$ mice upon FAK and Src action.

EXAMPLE 10

Silencing PIPK1γ Increases GiPCR Signaling in PTPμ$^{-/-}$ Osteoblasts

To further assess the implication of PIPK1γ in the mechanism of action behind PTPμ deficiency, a SiRNA approach was used to knockdown the expression of PIPK1γ in WT and PTPμ$^{-/-}$ osteoblasts prior to initiating GiPCR signaling with somatostatin stimulation. Efficiency of siRNA in WT and PTPμ$^{-/-}$ osteoblasts was confirmed by qPCR and Western blot analysis (FIGS. 6 B and C).

Representative CellKey™ raw data curves illustrated in FIGS. 6 D-G show that impedance signatures were not affected in WT and PTPμ$^{-/-}$ osteoblasts depleted of PIPK1γ.

Figure 6H:
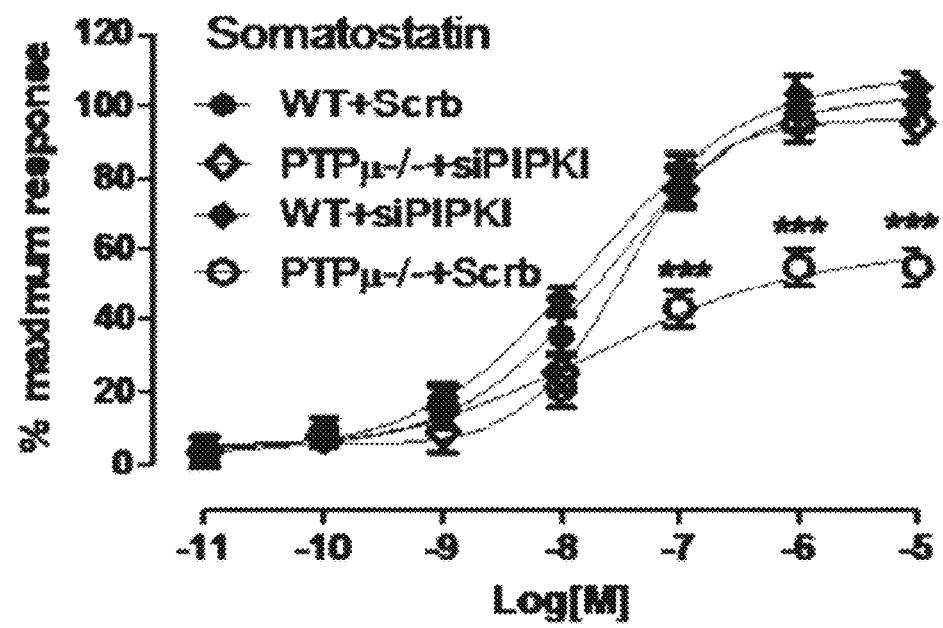

Both cells exhibited typical CDS response of GiPCR following somatostatin stimulation. In contrast, the screening at varying concentrations of somatostatin revealed that depletion of PIPK1γ enhanced response to somatostatin stimulation in osteoblasts from PTPμ deficiency mice, but not in those from WT mice. (FIG. 6 H, compare PTPμ$^{-/-}$+siPIPK1 (higher response) vs. PTPμ$^{-/-}$+scrb (lower response) and WT+siPIPK1 vs. WT+scrb (same response)). In addition, PTPμ$^{-/-}$ osteoblasts depleted of PIPK1γ exhibited similar degree of response to somatostatin stimulation than WT osteoblasts, indicating that depletion of PIPK1γ abrogates the difference in their ability to respond to GiPCR stimulation. (FIG. 6H).

Collectively, these results suggest that the amplified reduction in GiPCR signaling observed in osteoblasts from PTPμ$^{-/-}$ deficient mice is due to the dysregulation of PIPK1γ activity resulting from loss of PTPμ.

EXAMPLE 11

Figure 7A:
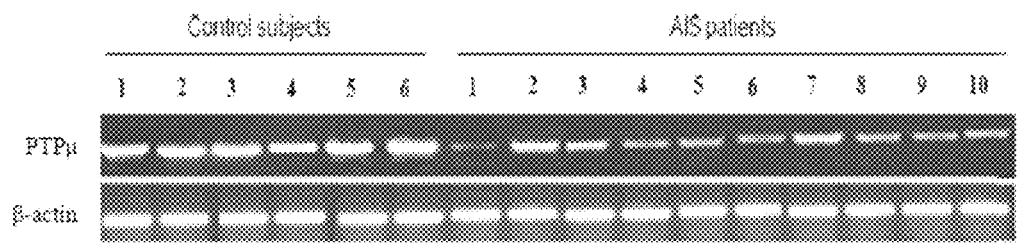
FIGS. 7A-C shows that PTPµ is downregulated in osteoblasts from patients with idiopathic scoliosis. In Panels A to C, the expression of PTPµ was determined in osteoblasts from scoliotic patients relative to those from control subjects using RT-PCT, qPCR and Western blot, respectively.
Figure 7B:
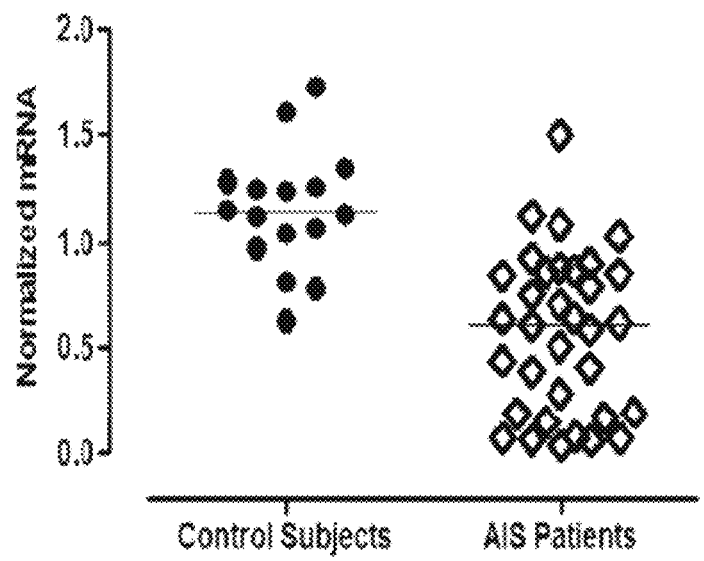
Figure 7C:
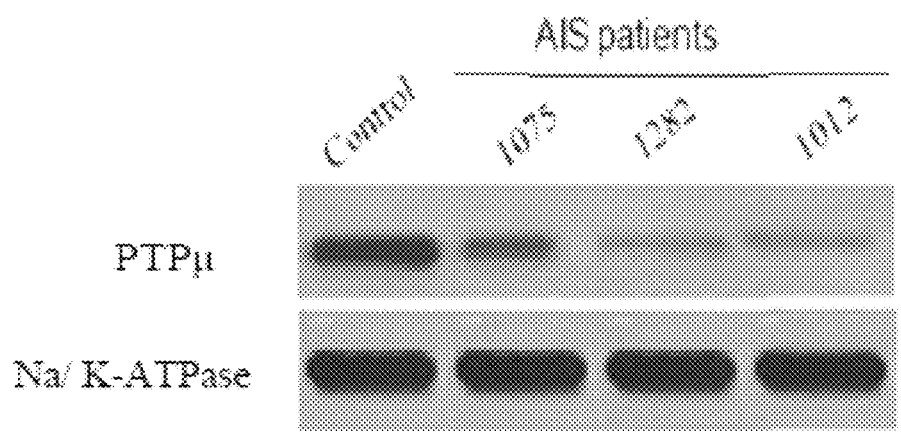

PTPμ is Downregulated and PIPK1γ is Upregulated in Osteoblasts from Patients with Idiopathic Scoliosis To explore the clinical relevance of the loss of PTPμ in the development of idiopathic scoliosis, PTPμ expression level in patients with idiopathic scoliosis (34) and healthy control subjects (17) was first investigated. It was found that PTPμ expression was clearly detected in osteoblasts from control subjects but was decreased in those from patients with idiopathic scoliosis, whereas expression levels of β-actin were similar between both groups (FIGS. 7 A and B). A decrease of at least a 50% was found in PTPμ mRNA in osteoblasts from scoliotic patients relative to that in control subjects. Similar results were obtained when cell lysates were analysed by Western blot to examine protein levels of PTPμ (FIG. 7C). These data clearly indicate that PTPμ is downregulated in patients with idiopathic scoliosis. These results also show that a variation in PTPμ protein levels can be observed among scoliotic patients.

Figure 8:
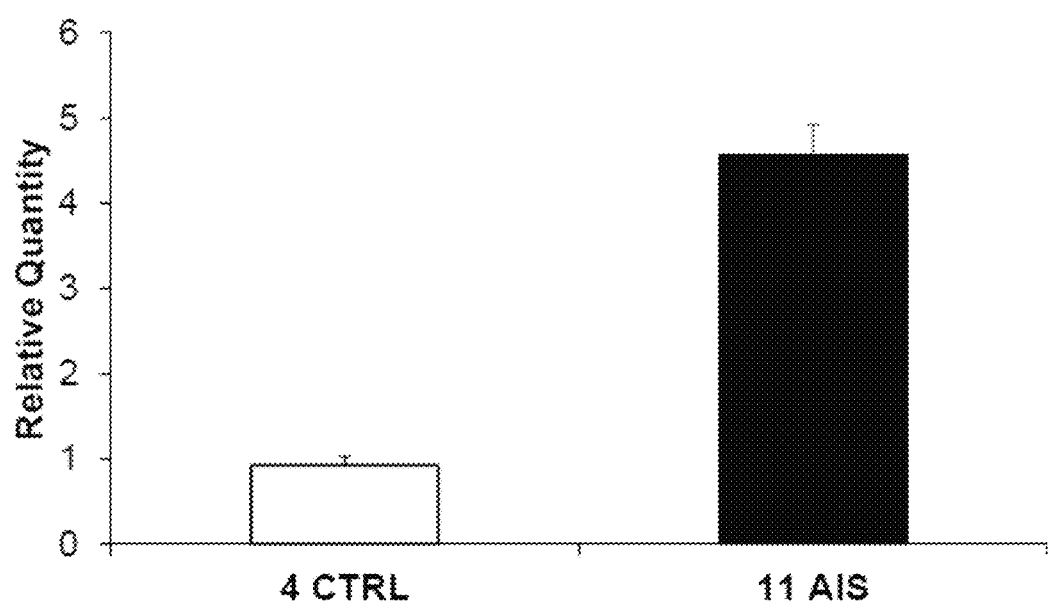
FIG. 8 shows that PIPK1γ expression is upregulated in AIS patients comparing to control subjects. The expression of PIPK1γ isoform 90 was determined in osteoblasts from scoliotic patients relative to those from control subjects using qPCR.

Also, the expression (RNA) of PIPK1γ was measured by qPCR in human AIS and control osteoblasts. It was shown to be up regulated in AIS patients (n=11) as compared to control subjects (n=4) (FIG. 8).

The scope of the claims should not be limited by the preferred embodiments set forth in the examples, but should be given the broadest interpretation consistent with the description as a whole.

REFERENCES

1. Kane, W. J. (1977) Scoliosis prevalence: a call for a statement of terms. *Clinical orthopedics and related research*, 43-46
2. Dickson, R. A. (1992) The etiology and pathogenesis of idiopathic scoliosis. *Acta orthopaedica Belgica* 58 Suppl 1, 21-25
3. Machida, M. (1999) Cause of idiopathic scoliosis. *Spine* 24, 2576-2583
4. Burwell, R. G. (2003) Aetiology of idiopathic scoliosis: current concepts. *Pediatric rehabilitation* 6, 137-170
5. Moreau, A., Wang, D. S., Forget, S., Azeddine, B., Angeloni, D., Fraschini, F., Labelle, H., Poitras, B., Rivard, C. H., and Grimard, G. (2004) Melatonin signaling dysfunction in adolescent idiopathic scoliosis. *Spine* 29, 1772-1781
6. Azeddine, B., Letelier, K., Wang da, S., Moldovan, F., and Moreau, A. (2007) Molecular determinants of melatonin signaling dysfunction in adolescent idiopathic scoliosis. *Clinical orthopedics and related research* 462, 45-52
7. Akoume, M. Y., Azeddine, B., Turgeon, I., Franco, A., Labele, H., Poitras, B., Rivard, C. H., Grimard, G., Ouellet, J., Parent, S., and Moreau, A. (2010) Cell-based screening test for idiopathic scoliosis using cellular dielectric spectroscopy. *Spine* 35, E601-608
8. Tozer, E. C., Hughes, P. E., and Loftus, J. C. (1996) Ligand binding and affinity modulation of integrins. *Biochemistry and cell biology* 74, 785-798
9. Hynes, R. O. (2002) Integrins: bidirectional, allosteric signaling machines. *Cell* 110, 673-687
10. Calderwood, D. A. (2004) Integrin activation. *Journal of cell science* 117, 657-666
11. Martel, V., Racaud-Sultan, C., Dupe, S., Mare, C., Paulhe, F., Galmiche, A., Block, M. R., and Abiges-Rizo, C. (2001) Conformation, locaization, and integrin binding of tain depend on its interaction with phosphoinositides. *The Journal of biological chemistry* 276, 21217-21227
12. Di Paolo, G., Pelegrini, L., Letinic, K., Cestra, G., Zoncu, R., Voronov, S., Chang, S., Guo, J., Wenk, M. R., and De Camli, P. (2002) Recruitment and regulation of phosphatidylinositol phosphate kinase type 1γ by the FERM domain of talin. *Nature* 420, 85-89
13. Ling, K., Doughman, R. L., Iyer, V. V., Firestone, A. J., Bairstow, S. F., Mosher, D. F., Schaller, M. D., and Anderson, R. A. (2003) Tyrosine phosphorylation of type 1γ phosphatidylnositol phosphate kinase by Src regulates an integrin-talin switch. *The Journal of cell biology* 163, 1339-1349
14. Sakamoto, Y., Ogita, H., Komura, H., and Takai, Y. (2008) Involvement of nectin in inactivation of integrin αvβ3 after the establishment of cell-cell adhesion. *Journal of Biological Chemistry* 283, 496-505
15. Oyama, J., Mural, I., Kanazawa, K., and Machida, M. (2006) Bipedal ambulation induces experimental scoliosis in C57BL6J mice with reduced plasma and pineal melatonin levels. *Journal of pineal research* 40, 219-224
16. Machida, M., Dubousset, J., Yamada, T., Kimura, J., Saito, M., Shiraishi, T., and Yamagishi, M. (2006) Experimental scoliosis in melatonin-deficient C57BL6J mice without pinealectomy. *Journal of pineal research* 41, 1-7
17. Hughes, P. E., Renshaw, M. W., Pfaff, M., Forsyth, J., Keivens, V. M., Schwartz, M. A., and Ginsberg, M. H. (1997) Suppression of integrin activation: a novel function of a Ras/Raf-initiated MAP kinase pathway. *Cell* 88, 521-530
18. Gronthos, S., Stewart, K., Graves, S. E., Hay, S., and Simmons, P. J. (1997) Integrin Expression and Function on Human Osteoblast-ike Cells. *Journal of Bone and Mineral Research* 12, 1189-1197
19. Grzesik, W. J., and Robey, P. G. (1994) Bone matrix RGD glycoproteins: immunolocalization and interaction with human primary osteoblastic bone cells in vitro. *Journal of bone and mineral research: the official journal of the American Society for Bone and Mineral Research* 9, 487-496
20. Clover, J., Dodds, R. A., and Gowen, M. (1992) Integrin subunit expression by human osteoblasts and osteoclasts in situ and in culture. *Journal of cell science* 103 (Pt 1), 267-271
21. Moursi, A. M., Globus, R. K., and Damsky, C. H. (1997) Interactions between integrin receptors and fibronectin are required for calvarial osteoblast differentiation in vitro. *Journal of cell science* 110 (Pt 18), 2187-2196

22. Pistone, M., Sanguineti, C., Federici, A., Sanguineti, F., Defilippi, P., Santolini, F., Querze, G., Marchisio, P. C., and Manduca, P. (1996) Integrin synthesis and utilization in cultured human osteoblasts. *Cell biology international* 20, 471-479.
23. Letelier K, Azeddine B, Parent S, Labele H, Rompré P H, Moreau A, Moldovan F. Estrogen cross-talk with the melatonin signaling pathway in human osteoblasts derived from adolescent idiopathic scoliosis patients. J Pineal Res. 2008 November; 45(4):383-93
24. Verdonk E, Johnson K, McGuinness R, Leung G, Chen Y W, Tang H R, Michelotti J M, Liu V F. Celular dielectric spectroscopy—a label-free comprehensive platform for functional evaluation of endogenous receptors. Assay Drug Dev Technol. 2006 October; 4(5):609-19.

The invention claimed is:

1. A composition comprising:
   (A) a cell sample from a subject having scoliosis or a subject which is a likely candidate for developing a scoliosis; and
   (i) at least one reagent for detecting Protein Tyrosine Phosphatase μ PTPμ expression and/or activity in the cell sample, wherein the at least one reagent for detecting PTPμ comprises (a) a non-natural oligonucleotide which hybridizes to PTPμ mRNA and which comprises a label and/or a modified base; or (b) a PTPμ antibody; and/or (ii) at least one reagent for detecting type I Phosphatidylinositol Phosphate Kinase isoform gamma PIPK1γ expression and/or activity in the cell sample, wherein at least one reagent for detecting PIPK1γ comprises a non-natural oligonucleotide which hybridizes to PIPK1γ mRNA and which comprises a label and/or a modified base; or (b) a PIPK1γ antibody.

2. The composition of claim 1, wherein the at least one reagent for detecting PIPK1γ expression comprises a tyrosine phosphorylated PIPK1γ antibody.

3. The composition of claim 1, wherein said scoliosis is an idiopathic scoliosis.

4. The composition of claim 3, wherein said idiopathic scoliosis is adolescent idiopathic scoliosis (AIS).

5. The composition of claim 1, wherein the subject is a likely candidate for developing adolescent idiopathic scoliosis (AIS).

6. The composition of claim 1, wherein the subject is pre-diagnosed as having adolescent idiopathic scoliosis (AIS), and the subject is at risk of developing a more severe AIS.

7. The composition of claim 1, wherein the cell sample comprises osteoblasts, myoblasts or peripheral blood mononuclear cells (PBMCs).

8. The composition of claim 1, wherein the cell sample comprises PBMCs.

9. The composition of claim 8, wherein said PBMCs comprise lymphocytes.

10. A method of stratifying a subject having a scoliosis or a subject which is a likely candidate for developing scoliosis, or of predicting the risk of developing a scoliosis in said subject said method comprising:
    (i) providing a cell sample isolated from the subject;
    (ii) (a) detecting Protein Tyrosine Phosphatase μ PTPμ expression and/or activity in the cell sample by contacting the cell sample with (a1) a non-natural oligonucleotide which hybridizes to PTPμ mRNA and which comprises a label and/or a modified base; or (a2) a PTPμ antibody;
    (b) detecting type I Phosphatidylinositol Phosphate Kinase isoform gamma (PIPK1γ) expression and/or activity in the cell sample by contacting the cell sample with (b1) a non-natural oligonucleotide which hybridizes to PIPK1γ mRNA and which comprises a label and/or a modified base; or (b2) a PIPK1γ antibody; or
    (c) a combination of (a) and (b); and
    (iii) (a) stratifying said subject into a AIS subclass based on the level of expression or activity of PTPμ and/or PIPK1γ in the cell sample of the subject; or
    (b) determining that the subject is at risk of developing a scoliosis when:
    (1) PTPμ expression and/or activity is decreased; and/or
    (2) PIPK1γ expression and/or activity is increased;
    in the subject's sample as compared to a level in a control sample.

11. The method of claim 10, wherein step (iii)(a) further comprises stratifying said subject as belonging to:
    (1) a first subclass characterized by:
    (a) a decreased level of PTPμ protein or mRNA as compared to a level in a control;
    (b) a decreased phosphatase activity of PTPμ protein as compared to a level in a control;
    (c) an increased level of PIPK1γ protein or mRNA as compared to a level in a control;
    (d) an increased PIPK1γ protein kinase activity as compared to a level in a control; or
    (e) any combination of at least two of (a) to (d); or (2) a second subclass characterized by:
 (a) an equal or increased level of PTPµ protein or mRNA as compared to a level in a control;
 (b) an equal or increased phosphatase activity of PTPµ protein as compared to a level in a control;
 (c) an equal or decreased level of PIPK1γ protein or mRNA as compared to a level in a control;
 (d) an equal or decreased PIPK1γ protein kinase activity as compared to a level in a control; or
 (e) any combination of at least two of (a) to (d).

12. The method of claim 11, wherein the PIPK1γ protein level in step (iii) is tyrosine phosphorylated PIPK1γ protein.

13. The method of claim 10, wherein step (iii)(b) of determining that the subject is at risk of developing a scoliosis is when:
 (a) PTPµ protein or mRNA level is decreased;
 (b) PTPµ protein phosphatase activity is decreased;
 (c) PIPK1γ protein or mRNA level is increased;
 (d) PIPK1γ protein kinase activity is increased; or
 (e) any combination of at least two of (a) to (d),
 in the subject's sample as compared to a level in a control sample.

14. The method of claim 10, wherein detecting PIPK1γ expression and/or activity in step (ii) (b) comprises detecting the level of tyrosine phosphorylated PIPK1γ protein in the sample.

15. The method of claim 10, wherein said scoliosis is an idiopathic scoliosis.

16. The method of claim 15, wherein said idiopathic scoliosis is adolescent idiopathic scoliosis (AIS).

17. The method of claim 10, wherein the subject is a likely candidate for developing adolescent idiopathic scoliosis.

18. The method of claim 10, wherein the subject is pre-diagnosed as having an idiopathic scoliosis, and the subject is at risk for developing the idiopathic scoliosis is a risk for developing a more severe idiopathic scoliosis.

19. The method of claim 18, wherein the subject is pre-diagnosed as having adolescent idiopathic scoliosis (AIS), and the subject is at risk of developing more severe AIS.

20. The method of claim 10, wherein said cell sample comprises osteoblasts, myoblasts or peripheral blood mononuclear cells (PBMC).

21. The method of claim 20, wherein said cell sample comprises PBMCs.

22. The method of claim 21, wherein said PBMCs comprises lymphocytes.

* * * * *

SEQUENCE LISTING

```
<160> NUMBER OF SEQ ID NOS: 39

<210> SEQ ID NO 1
<211> LENGTH: 18
<212> TYPE: DNA
<213> ORGANISM: Artificial sequence
<220> FEATURE:
<223> OTHER INFORMATION: Synthetic Construct

<400> SEQUENCE: 1
ggaaatcgtg cgtgacat                                                       18

<210> SEQ ID NO 2
<211> LENGTH: 23
<212> TYPE: DNA
<213> ORGANISM: Artificial sequence
<220> FEATURE:
<223> OTHER INFORMATION: Synthetic Construct

<400> SEQUENCE: 2
tcatgatgga gttgaaggta gtt                                                 23

<210> SEQ ID NO 3
<211> LENGTH: 19
<212> TYPE: DNA
<213> ORGANISM: Artificial sequence
<220> FEATURE:
<223> OTHER INFORMATION: Synthetic Construct

<400> SEQUENCE: 3
ggccggactt ttgctaact                                                      19

<210> SEQ ID NO 4
<211> LENGTH: 21
<212> TYPE: DNA
<213> ORGANISM: Artificial sequence
<220> FEATURE:
<223> OTHER INFORMATION: Synthetic Construct

<400> SEQUENCE: 4
tgtgctatac ggctcatcaa a                                                   21

<210> SEQ ID NO 5
<211> LENGTH: 20
<212> TYPE: DNA
<213> ORGANISM: Artificial sequence
<220> FEATURE:
<223> OTHER INFORMATION: Synthetic Construct

<400> SEQUENCE: 5
agcatcggat ttgagacctg                                                     20

<210> SEQ ID NO 6
<211> LENGTH: 20
<212> TYPE: DNA
<213> ORGANISM: Artificial sequence
<220> FEATURE:
```

<223> OTHER INFORMATION: Synthetic Construct

<400> SEQUENCE: 6
tgagtccact tggctttctg                                                    20

<210> SEQ ID NO 7
<211> LENGTH: 19
<212> TYPE: DNA
<213> ORGANISM: Artificial sequence
<220> FEATURE:
<223> OTHER INFORMATION: Synthetic Construct

<400> SEQUENCE: 7
atgtgtcaga cctgccttg                                                     19

<210> SEQ ID NO 8
<211> LENGTH: 21
<212> TYPE: DNA
<213> ORGANISM: Artificial sequence
<220> FEATURE:
<223> OTHER INFORMATION: Synthetic Construct

<400> SEQUENCE: 8
ttgtcccgac tttctacctt g                                                  21

<210> SEQ ID NO 9
<211> LENGTH: 22
<212> TYPE: DNA
<213> ORGANISM: Artificial sequence
<220> FEATURE:
<223> OTHER INFORMATION: Synthetic Construct

<400> SEQUENCE: 9
ggaaagtcca tcctgtatgt gg                                                 22

<210> SEQ ID NO 10
<211> LENGTH: 20
<212> TYPE: DNA
<213> ORGANISM: Artificial sequence
<220> FEATURE:
<223> OTHER INFORMATION: Synthetic Construct

<400> SEQUENCE: 10
gagtttccag atgagcaggg                                                    20

<210> SEQ ID NO 11
<211> LENGTH: 22
<212> TYPE: DNA
<213> ORGANISM: Artificial sequence
<220> FEATURE:
<223> OTHER INFORMATION: Synthetic Construct

<400> SEQUENCE: 11
gtccccacag tagacacata tg                                                 22

<210> SEQ ID NO 12
<211> LENGTH: 20
<212> TYPE: DNA
<213> ORGANISM: Artificial sequence
<220> FEATURE:
<223> OTHER INFORMATION: Synthetic Construct

<400> SEQUENCE: 12
tcaactcctc gctttccatg                                                    20

<210> SEQ ID NO 13
<211> LENGTH: 25
<212> TYPE: DNA
<213> ORGANISM: Artificial sequence
<220> FEATURE:
<223> OTHER INFORMATION: Synthetic Construct

<400> SEQUENCE: 13
gacatttgga tgaactttag tcacc                                    25

<210> SEQ ID NO 14
<211> LENGTH: 21
<212> TYPE: DNA
<213> ORGANISM: Artificial sequence
<220> FEATURE:
<223> OTHER INFORMATION: Synthetic Construct

<400> SEQUENCE: 14
ggcaatggaa ttcacgactt g                                        21

<210> SEQ ID NO 15
<211> LENGTH: 22
<212> TYPE: DNA
<213> ORGANISM: Artificial sequence
<220> FEATURE:
<223> OTHER INFORMATION: Synthetic Construct

<400> SEQUENCE: 15
ggatgagact tcagcactca ag                                       22

<210> SEQ ID NO 16
<211> LENGTH: 24
<212> TYPE: DNA
<213> ORGANISM: Artificial sequence
<220> FEATURE:
<223> OTHER INFORMATION: Synthetic Construct

<400> SEQUENCE: 16
ggtgaaataa cgtttgggtc tttg                                     24

<210> SEQ ID NO 17
<211> LENGTH: 22
<212> TYPE: DNA
<213> ORGANISM: Artificial sequence
<220> FEATURE:
<223> OTHER INFORMATION: Synthetic Construct

<400> SEQUENCE: 17
ggaaagtcca tcctgtatgt gg                                       22

<210> SEQ ID NO 18
<211> LENGTH: 20
<212> TYPE: DNA
<213> ORGANISM: Artificial sequence
<220> FEATURE:
<223> OTHER INFORMATION: Synthetic Construct

<400> SEQUENCE: 18
gagtttccag atgagcaggg                                          20

<210> SEQ ID NO 19
<211> LENGTH: 20
<212> TYPE: DNA
<213> ORGANISM: Artificial sequence
<220> FEATURE:
<223> OTHER INFORMATION: Synthetic Construct

<400> SEQUENCE: 19
cttgcactcc tggctatctg                                                    20

<210> SEQ ID NO 20
<211> LENGTH: 19
<212> TYPE: DNA
<213> ORGANISM: Artificial sequence
<220> FEATURE:
<223> OTHER INFORMATION: Synthetic Construct

<400> SEQUENCE: 20
tgcgtggaga taggctttc                                                     19

<210> SEQ ID NO 21
<211> LENGTH: 22
<212> TYPE: DNA
<213> ORGANISM: Artificial sequence
<220> FEATURE:
<223> OTHER INFORMATION: Synthetic Construct

<400> SEQUENCE: 21
gattgggttg cttaaagtcc tg                                                 22

<210> SEQ ID NO 22
<211> LENGTH: 20
<212> TYPE: DNA
<213> ORGANISM: Artificial sequence
<220> FEATURE:
<223> OTHER INFORMATION: Synthetic Construct

<400> SEQUENCE: 22
ggtaggtgac tgctcttgtg                                                    20

<210> SEQ ID NO 23
<211> LENGTH: 21
<212> TYPE: DNA
<213> ORGANISM: Artificial sequence
<220> FEATURE:
<223> OTHER INFORMATION: Synthetic Construct

<400> SEQUENCE: 23
cagattacag tgcaggtgga g                                                  21

<210> SEQ ID NO 24
<211> LENGTH: 21
<212> TYPE: DNA
<213> ORGANISM: Artificial sequence
<220> FEATURE:
<223> OTHER INFORMATION: Synthetic Construct

<400> SEQUENCE: 24
gctggcagtt tctacttcaa c                                                  21

<210> SEQ ID NO 25
<211> LENGTH: 25
<212> TYPE: RNA
<213> ORGANISM: Artificial sequence
<220> FEATURE:
<223> OTHER INFORMATION: Synthetic Construct

<400> SEQUENCE: 25
ccacagccac aagcagucca gauua                                              25

<210> SEQ ID NO 26
<211> LENGTH: 22

```
<212> TYPE: RNA
<213> ORGANISM: Artificial sequence
<220> FEATURE:
<223> OTHER INFORMATION: Synthetic Construct

<400> SEQUENCE: 26
ccuccacauc gggauugaua uu                                             22

<210> SEQ ID NO 27
<211> LENGTH: 4998
<212> TYPE: DNA
<213> ORGANISM: Homosapiens

<400> SEQUENCE: 27
ctcccttggc cggcggcgct tgttgttcgg cggcggcggt cgcagctcgg gtcccctcg      60 ggcgccccg ccgccgtccg cgcgcggcca tggagctgga ggtaccggac gaggcggaga    120
gcgctgaggc gggggccgtg ccctcggagg cggcgtgggc ggcagagagc ggggcggcgg    180
caggtttggc tcagaagaag gcggcccccaa cagaggttct gtccatgacg gcacagccgg    240
gccctggcca tgggaagaag ttgggccatc gaggtgtgga cgcatccggc gaaaccacct    300
acaagaagac cacctcctcc accctgaagg gtgccatcca gctgggcatc ggctacaccg    360
tgggccacct gagctccaag cccgaacgcg acgtgctcat gcaggacttc tacgtggtgg    420
agagcatctt cttccccagc gaaggcagca acctcacccc cgcccaccac ttccaggact    480
tccgcttcaa gacctatgca cctgtcgcct tccgctactt ccgggagctc tttgggatcc    540
ggccagatga ttacttgtac tccctgtgca atgagccgct gatcgagctg tccaacccgg    600
gcgccagtgg ctccctcttc tacgtcacca gcgacgacga gttcatcatc aagaccgtca    660
tgcacaagga ggccgagttc ctgcagaagc tgctccctgg ctactacatg aacctcaacc    720
agaacccgcg gacgctgctg cccaagttct atgggctgta ctgcgtgcag tcggggggca    780
agaacatccg cgtcgtggtc atgaacaaca tcctgccccg cgtggtcaag atgcacctca    840
agttcgacct caagggctcc acctacaagc ggcgcgccag caagaaggag aaggagaaga    900
gcttccccac ctacaaggac ctggacttca tgcaggacat gcccgagggg ctcctgctgg    960
acgccgacac cttcagcgcc ctggtcaaga cgctgcagcg ggactgcctg gtcctggaaa   1020
gtttcaagat catggactac agcctgctgc tgggcgtgca caacatcgac cagcacgagc   1080
gcgagcggca ggcgcagggc gcccagagca cctcagatga aagcggcct gtgggccaga   1140 aggcgctcta ctccacggcc atggagtcca tccagggtgg cgccgcgcgc gggaggcca   1200 tcgaatcgga tgacacgatg ggcgggatcc ccgctgtgaa cggccgcggg gagcggctgc   1260
tgctgcacat tggcatcatc gacatcctgc agtcctacag gttcatcaag aaactggagc   1320
acacctggaa ggccctcgtc cacgatgggg acacggtgtc cgtccaccgc ccagcttct   1380 atgccgagcg cttttttcaag ttcatgagca acacggtctt tcggaagaac tcctccctga   1440
agtcctcgcc ctccaagaag gggcgcgcg gagccttgct agctgtgaaa ccgctggggc   1500
ccaccgctgc cttctcggcc agccagatcc ctagcgagcg ggaggaggcc cagtacgacc   1560 tgcgggggc ccgcagctac cccacgctgg aggacgaagg ccggcccgac ctcctgccct   1620
gcacgccacc ttcttctcgaa gaagccacta cagcctccat tgccacgact ctgtcatcca   1680
catccctctc cattcctgag cggtccccct cggagacgtc ggagcagccg cggtacaggc   1740
ggcgcacaca gtcgtctgga caggatggca ggccgcagga ggagcaccc gcggaagagg   1800 atctgcagca gattacagtg caggtggagc ctgcgtgcag cgtggagatt gtggtcccca   1860
```

```
aagaggagga cgcaggggtg gaggcttccc cggccggtgc ctctgctgct gttgaagtag    1920
aaactgccag ccaggcctca gacgaggagg gcgcacctgc cagccaggcc tcggacgagg    1980
aggacgcgcc cgccaccgac atctactttt aatttctatg cagcccccga cccagagccg    2040
agctccactt ctgctccggc tgccccgaa ggcgctgccc accccgctga ggcccagagc    2100
tcgggagatg cccgcctcgc cgccccaccg gacctcgtcc tcccctgca cggatgccga    2160 cggccgggcc cctccccgac aagcctccca gggcccggc accccggtcg gcagcctgcc    2220
cctgtgagac ccaccctccc gagcggccaa tcgcatttga gtccttattt ggcacagaga    2280
cggaagcacg tgtgtgccgt tttaggaaaa gaacaaaaaa gacacaaaca aaccaaccag    2340
agggagaaga gccctgccc actgcactct ttggttctct gctgtgcctg cctgtgtcct    2400
gaggaagaag ccaggctgtt cgcggtggcc tctggggacc tgagcccgg ggcccatc    2460 ggcctgcaga ggggacggct ggggtcccga gcaactctgc ctccatccac gtgggaagcg    2520
gaccctcctg ccctcagctt gggtttgggg gcctcagtgc aggacatctg gcctgaacat    2580
cgactgtggg gacagccctc gccctgccaa gcactgcggc cactcagcag ctatgttccc    2640
gccgcagtgg ggccctgacg cccacctccc aggtgcccct cgagcaaaaa cctctggcgc    2700
ctccaatcca gacccaccac agctggaggg ccaggcctcc tcttcccag gctgccaccc    2760 acgctggcgg agctcagggc tggggacttg tccttctctt ccaacgtagg ccactcagca    2820
actggcatgg agggcccagg caacggagac gttttctcca tggcaggaca gagcgggagg    2880
ccgggccttg ggccacagga gaccagctca gggcggaagg tcaggctccc cgccccctcc    2940
acgtggagac atggcctagg gggccaggcc cggctccaca ggagtctcct tcaggactgg    3000
tgtggatgtc cgccgcctct ttcttgttta agtgatgtga tgtctccgag gaggggagag    3060
aagactttgt ttccgactca tcaccctcca agagggcagc gctcccagtg gtgggactca    3120
gcccagactg ccctggggca gcttcctggg cccgctgcgc tcagagggtg ctggttggag    3180
gccagagctc ggcagagtca cccacccgtc ccttccccag gacccctgag aggggcttat    3240
tggtgatggc tgtgggaatc ccccacttcc aagatgtgcc caggatgtga ggagctggag    3300
tggaagctgc acctttggga agaattcctc tccagacctg gcagagcctg gtgtggggtc    3360
tgagacggcc ggagaacctc ccaggcaggg ctctgtgttt tgtctgttac aacctccgta    3420
tgacgccacg ccaccgctg ttcacgtccc gtcggcctcc tgcacagccc acacgctgcg    3480
cccggaaggc ccctgctgtg gagaagccgg acccatcccc gaggtcccca gcgaggacac    3540
acactccacg agagcagccc ctccactctg cccaggagag gggccgaccc tcctcgggaa    3600
ccggccagcc gcgtggctcc cagcatccat caggacaagc ccacgtgggg tcctccctgc    3660
gtgctcagag ggtctgtcca gccctgggaa gcgaccttgg cctcagttca cagcctggtg    3720
ctcatctgct ggcaccgggc atccacccat cagcccccgc cctgtccctc cgaaggacac    3780
ccagcaggca cccccggg aggcagggc agaggtcaga aggggtgtct gggacctgga    3840
tggccagcag ggacaggggc attgtcatct caaaggccca accccagag gccacaccag    3900 tcctcccagg gagtcctcga gtcgccctgc ccagagccct ggcaccagag acgccaagag    3960 cctgtgggt gactcggagc agcaggtgtg gccccgggcg gcggcaccg cgtccagggc    4020 agcctccctc cgctgagtga cacgggacac cagtgcccgg ccgacgcgcc tttgcaggag    4080
aaatgtgcaa acctctgtgg ataccatttc atttccattc ttgtgttgtc tccaaggccc    4140
ttttggagat atacttggtg ttggttgtgt tttttggttc cttttcagag aactgtaaac    4200
cgaggctgac gtgctccact gactgtgccg aggggcgggg gcaggaggac ggcaagacct    4260
```

```
atttataata tttagcgaac tcggtctccc tcagatcccc cgcgagggag gctgctggac    4320
ccaccccgct gtccccatg atagaagtct gtaaatacct tggtgaccaa tgcccacttc     4380
ccctcctggg tcacctctga tggctgctgt ccactgagaa cgtgggcagt gtccaaattc    4440
ctgtactgta aagactaaaa ggcgtttgct ctgagactga caaggcggaa acttccatgt    4500
gtctcctgcc aggctctgtc ccctacgcc atcccgacac gtccccgttc ccccgaaacc     4560
tggctcagtg caatactccc attgccatgg ggtccttcac catggtactg tctccacagc   4620
cctcagtccc caccccagga gaggcgcctg ccacctcctc ctcatctccg gtggttcaat   4680
cgctccgcct gtccccaacc cagtcccatt tttatggcca aactgattct gaaacaaaat   4740
gaaactgcaa acctcgtgtg tcttaactcc ccccagggat gccactccat tcctccgccc   4800
cgtggtctgg tgcgtgacaa tccaaagcgc cgagacgagg gtgctgtgtc cctcaaaccc   4860
agagtggtgg gcgcctctga accatacag ccactcctgg ccccaaacac tggtttgcat    4920
cccaggttcc tcgcccacct accccgcca caccccgtct ttttagagat ctctctaata    4980
aatcgggtaa taagcatc                                                  4998

<210> SEQ ID NO 28
<211> LENGTH: 668
<212> TYPE: PRT
<213> ORGANISM: homo sapiens

<400> SEQUENCE: 28

Met Glu Leu Glu Val Pro Asp Glu Ala Glu Ser Ala Glu Ala Gly Ala
1               5                  10                  15

Val Pro Ser Glu Ala Ala Trp Ala Ala Glu Ser Gly Ala Ala Ala Gly
            20                  25                  30

Leu Ala Gln Lys Lys Ala Ala Pro Thr Glu Val Leu Ser Met Thr Ala
        35                  40                  45

Gln Pro Gly Pro Gly His Gly Lys Lys Leu Gly His Arg Gly Val Asp
    50                  55                  60

Ala Ser Gly Glu Thr Thr Tyr Lys Lys Thr Thr Ser Ser Thr Leu Lys
65                  70                  75                  80

Gly Ala Ile Gln Leu Gly Ile Gly Tyr Thr Val Gly His Leu Ser Ser
                85                  90                  95

Lys Pro Glu Arg Asp Val Leu Met Gln Asp Phe Tyr Val Val Glu Ser
            100                 105                 110

Ile Phe Phe Pro Ser Glu Gly Ser Asn Leu Thr Pro Ala His His Phe
        115                 120                 125

Gln Asp Phe Arg Phe Lys Thr Tyr Ala Pro Val Ala Phe Arg Tyr Phe
    130                 135                 140

Arg Glu Leu Phe Gly Ile Arg Pro Asp Asp Tyr Leu Tyr Ser Leu Cys
145                 150                 155                 160

Asn Glu Pro Leu Ile Glu Leu Ser Asn Pro Gly Ala Ser Gly Ser Leu
                165                 170                 175

Phe Tyr Val Thr Ser Asp Asp Glu Phe Ile Ile Lys Thr Val Met His
            180                 185                 190

Lys Glu Ala Glu Phe Leu Gln Lys Leu Leu Pro Gly Tyr Tyr Met Asn
        195                 200                 205

Leu Asn Gln Asn Pro Arg Thr Leu Leu Pro Lys Phe Tyr Gly Leu Tyr
    210                 215                 220

Cys Val Gln Ser Gly Gly Lys Asn Ile Arg Val Val Val Met Asn Asn
225                 230                 235                 240
```

```
Ile Leu Pro Arg Val Val Lys Met His Leu Lys Phe Asp Leu Lys Gly
            245                 250                 255

Ser Thr Tyr Lys Arg Arg Ala Ser Lys Glu Lys Glu Lys Ser Phe
        260                 265                 270

Pro Thr Tyr Lys Asp Leu Asp Phe Met Gln Asp Met Pro Glu Gly Leu
        275                 280                 285

Leu Leu Asp Ala Asp Thr Phe Ser Ala Leu Val Lys Thr Leu Gln Arg
    290                 295                 300

Asp Cys Leu Val Leu Glu Ser Phe Lys Ile Met Asp Tyr Ser Leu Leu
305                 310                 315                 320

Leu Gly Val His Asn Ile Asp Gln His Glu Arg Glu Arg Gln Ala Gln
                325                 330                 335

Gly Ala Gln Ser Thr Ser Asp Glu Lys Arg Pro Val Gly Gln Lys Ala
                340                 345                 350

Leu Tyr Ser Thr Ala Met Glu Ser Ile Gln Gly Gly Ala Ala Arg Gly
            355                 360                 365

Glu Ala Ile Glu Ser Asp Asp Thr Met Gly Gly Ile Pro Ala Val Asn
        370                 375                 380

Gly Arg Gly Glu Arg Leu Leu Leu His Ile Gly Ile Ile Asp Ile Leu
385                 390                 395                 400

Gln Ser Tyr Arg Phe Ile Lys Lys Leu Glu His Thr Trp Lys Ala Leu
                405                 410                 415

Val His Asp Gly Asp Thr Val Ser Val His Arg Pro Ser Phe Tyr Ala
            420                 425                 430

Glu Arg Phe Phe Lys Phe Met Ser Asn Thr Val Phe Arg Lys Asn Ser
        435                 440                 445

Ser Leu Lys Ser Ser Pro Ser Lys Lys Gly Arg Gly Gly Ala Leu Leu
    450                 455                 460

Ala Val Lys Pro Leu Gly Pro Thr Ala Ala Phe Ser Ala Ser Gln Ile
465                 470                 475                 480

Pro Ser Glu Arg Glu Glu Ala Gln Tyr Asp Leu Arg Gly Ala Arg Ser
                485                 490                 495

Tyr Pro Thr Leu Glu Asp Glu Gly Arg Pro Asp Leu Leu Pro Cys Thr
            500                 505                 510

Pro Pro Ser Phe Glu Glu Ala Thr Thr Ala Ser Ile Ala Thr Thr Leu
        515                 520                 525

Ser Ser Thr Ser Leu Ser Ile Pro Glu Arg Ser Pro Ser Glu Thr Ser
    530                 535                 540

Glu Gln Pro Arg Tyr Arg Arg Thr Gln Ser Ser Gly Gln Asp Gly
545                 550                 555                 560

Arg Pro Gln Glu Glu Pro Pro Ala Glu Glu Asp Leu Gln Gln Ile Thr
                565                 570                 575

Val Gln Val Glu Pro Ala Cys Ser Val Glu Ile Val Val Pro Lys Glu
            580                 585                 590

Glu Asp Ala Gly Val Glu Ala Ser Pro Ala Gly Ala Ser Ala Ala Val
        595                 600                 605

Glu Val Glu Thr Ala Ser Gln Ala Ser Asp Glu Glu Gly Ala Pro Ala
    610                 615                 620

Ser Gln Ala Ser Asp Glu Glu Asp Ala Pro Ala Thr Asp Ile Tyr Phe
625                 630                 635                 640

Pro Thr Asp Glu Arg Ser Trp Val Tyr Ser Pro Leu His Tyr Ser Ala
                645                 650                 655
```

Gln Ala Pro Pro Ala Ser Asp Gly Glu Ser Asp Thr
        660                 665

<210> SEQ ID NO 29
<211> LENGTH: 5082
<212> TYPE: DNA
<213> ORGANISM: homo sapiens

<400> SEQUENCE: 29

| | | | | |
|---|---|---|---|---|
| ctcccttggc | cggcggcgct | tgttgttcgg | cggcggcggt | cgcagctcgg | gtcccctcg | 60 |
| ggcgccccg | ccgccgtccg | cgcgcggcca | tggagctgga | ggtaccggac | gaggcggaga | 120 |
| gcgctgaggc | gggggccgtg | ccctcggagg | cggcgtgggc | ggcagagagc | ggggcggcgg | 180 |
| caggtttggc | tcagaagaag | gcggccccaa | cagaggttct | gtccatgacg | gcacagccgg | 240 |
| gccctggcca | tgggaagaag | ttgggccatc | gaggtgtgga | cgcatccggc | gaaaccacct | 300 |
| acaagaagac | cacctcctcc | accctgaagg | gtgccatcca | gctgggcatc | ggctacaccg | 360 |
| tgggccacct | gagctccaag | cccgaacgcg | acgtgctcat | gcaggacttc | tacgtggtgg | 420 |
| agagcatctt | cttccccagc | gaaggcagca | acctcacccc | cgcccaccac | ttccaggact | 480 |
| tccgcttcaa | gacctatgca | cctgtcgcct | tccgctactt | ccgggagctc | tttgggatcc | 540 |
| ggccagatga | ttacttgtac | tccctgtgca | atgagccgct | gatcgagctg | tccaacccgg | 600 |
| gcgccagtgg | ctccctcttc | tacgtcacca | gcgacgacga | gttcatcatc | aagaccgtca | 660 |
| tgcacaagga | ggccgagttc | ctgcagaagc | tgctccctgg | ctactacatg | aacctcaacc | 720 |
| agaacccgcg | gacgctgctg | cccaagttct | atgggctgta | ctgcgtgcag | tcgggggggca | 780 |
| agaacatccg | cgtcgtggtc | atgaacaaca | tcctgccccg | cgtggtcaag | atgcacctca | 840 |
| agttcgacct | caagggctcc | acctacaagc | ggcgcgccag | caagaaggag | aaggagaaga | 900 |
| gcttccccac | ctacaaggac | ctggacttca | tgcaggacat | gcccgagggg | ctcctgctgg | 960 |
| acgccgacac | cttcagcgcc | ctggtcaaga | cgctgcagcg | ggactgcctg | gtcctggaaa | 1020 |
| gtttcaagat | catggactac | agcctgctgc | tgggcgtgca | caacatcgac | cagcacgagc | 1080 |
| gcgagcggca | ggcgcagggc | gcccagagca | cctcagatga | aagcggcct | gtgggccaga | 1140 |
| aggcgctcta | ctccacggcc | atggagtcca | tccagggtgg | cgccgcgcgc | ggggaggcca | 1200 |
| tcgaatcgga | tgacacgatg | ggcgggatcc | ccgctgtgaa | cggccgcggg | gagcggctgc | 1260 |
| tgctgcacat | tggcatcatc | gacatcctgc | agtcctacag | gttcatcaag | aaactggagc | 1320 |
| acacctggaa | ggcccctcgtc | cacgatgggg | acacggtgtc | cgtccaccgc | cccagcttct | 1380 |
| atgccgagcg | cttttcaag | ttcatgagca | acacggtctt | tcggaagaac | tcctccctga | 1440 |
| agtcctcgcc | ctccaagaag | gggcgcggcg | gagccttgct | agctgtgaaa | ccgctggggc | 1500 |
| ccaccgctgc | cttctcggcc | agccagatcc | ctagcgagcg | ggaggaggcc | cagtacgacc | 1560 |
| tgcgggggggc | ccgcagctac | cccacgctgg | aggacgaagg | ccggcccgac | tcctgccct | 1620 |
| gcacgccacc | ttctttcgaa | gaagccacta | cagcctccat | tgccacgact | ctgtcatcca | 1680 |
| catccctctc | cattcctgag | cggtcccccct | cggagacgtc | ggagcagccg | cggtacaggc | 1740 |
| ggcgcacaca | gtcgtctgga | caggatggcc | ggccgcagga | ggagccaccc | gcggaagagg | 1800 |
| atctgcagca | gattacagtg | caggtggagc | ctgcgtgcag | cgtggagatt | gtggtccca | 1860 |
| aagaggagga | cgcaggggtg | gaggcttccc | cggccggtgc | ctctgctgct | gttgaagtag | 1920 |
| aaactgccag | ccaggcctca | gacgaggagg | gcgcacctgc | cagccaggcc | tcggacgagg | 1980 |
| aggacgcgcc | cgccaccgac | atctactttc | ccaccgatga | gaggagctgg | gtgtactccc | 2040 |

| | |
|---|---|
| cgctccacta tagcgcccag gcccccccgg cctccgacgg cgagagcgac acataatttc | 2100 |
| tatgcagccc ccgacccaga gccgagctcc acttctgctc cggctgcccc cgaaggcgct | 2160 |
| gcccaccccg ctgaggccca gagctcggga gatgcccgcc tcgccgcccc accggacctc | 2220 |
| gtcctccccc tgcacggatg ccgacggccg ggccctccc cgacaagcct cccagggccc | 2280 |
| cggcaccccg gtcggcagcc tgcccctgtg agacccaccc tcccgagcgg ccaatcgcat | 2340 |
| ttgagtcctt atttggcaca gagacggaag cacgtgtgtg ccgttttagg aaaagaacaa | 2400 |
| aaaagacaca aacaaaccaa ccagagggag aagagcccct gcccactgca ctctttggtt | 2460 |
| ctctgctgtg cctgcctgtg tcctgaggaa gaagccaggc tgttcgcggt ggcctctggg | 2520 |
| gacctgagcc ccgggggccc catcggcctg cagaggggac ggctggggtc ccgagcaact | 2580 |
| ctgcctccat ccacgtggga agcggaccct cctgccctca gcttgggttt ggggggcctca | 2640 |
| gtgcaggaca tctggcctga acatcgactg tggggacagc cctcgccctg ccaagcactg | 2700 |
| cggccactca gcagctatgt tcccgccgca gtggggccct gacgcccacc tcccaggtgc | 2760 |
| ccctcgagca aaaacctctg cgcctccaa tccagcccca ccacagctgg agggccaggc | 2820 |
| ctcctcttcc ccaggctgcc acccacgctg gcggagctca gggctgggga cttgtccttc | 2880 |
| tcttccaacg taggccactc agcaactggc atggaggggcc caggcaacgg agacgttttc | 2940 |
| tccatggcag gacagagcgg gaggccgggc cttgggccac aggagaccag ctcagggcgg | 3000 |
| aaggtcaggc tccccgcccc ctccacgtgg agacatggcc taggggggcca ggcccggctc | 3060 |
| cacaggagtc tccttcagga ctggtgtgga tgtccgccgc ctctttcttg tttaagtgat | 3120 |
| gtgatgtctc cgaggagggg agagaagact ttgtttccga ctcatcaccc tccaagaggg | 3180 |
| cagcgctccc agtggtggga ctcagcccag actgccctgg ggcagcttcc tgggcccgct | 3240 |
| gcgctcagag ggtgctggtt ggaggccaga gctcggcaga gtcacccacc ctgcccttcc | 3300 |
| ccaggacccc tgagaggggc ttattggtga tggctgtggg aatcccccac ttccaagatg | 3360 |
| tgcccaggat gtgaggagct ggagtggaag ctgcacctt gggaagaatt cctctccaga | 3420 |
| cctggcagag cctggtgtgg ggtctgagac ggccggagaa cctcccaggc agggctctgt | 3480 |
| gttttgtctg ttacaacctc cgtatgacgc cacgccaccc gctgttcacg tcccgtcggc | 3540 |
| ctcctgcaca gcccacacgc tgcgcccgga aggcccctgc tgtggagaag ccggacccat | 3600 |
| ccccgaggtc cccagcgagg acacacactc cacgagagca gcccctccac tctgcccagg | 3660 |
| agaggggccg accctcctcg ggaaccggcc agccgcgtgg ctcccagcat ccatcaggac | 3720 |
| aagcccacgt ggggtcctcc ctgcgtgctc agagggtctg tccagccctg ggaagcgacc | 3780 |
| ttggcctcag ttcacagcct ggtgctcatc tgctggcacc gggcatccac ccatcagccc | 3840 |
| ccgcctgtc cctccgaagg acacccagca ggcaccccc ggggaggcag ggcagaggt | 3900 |
| cagaagggt gtctgggacc tggatggcca gcagggacag gggcattgtc atctcaaagg | 3960 |
| cccaaccccc agaggccaca ccagtcctcc caggagtcc tcgagtcgcc ctgcccagag | 4020 |
| ccctggcacc agagacgcca agagcctgtg gggtgactcg gagcagcagg tgtggccccg | 4080 |
| ggcgggcggc accgcgtcca gggcagcctc cctccgctga gtgacacggg acaccagtgc | 4140 |
| ccggccgacg cgcctttgca ggagaaatgt gcaaacctct gtggatacca tttcatttcc | 4200 |
| attcttgtgt tgtctccaag gccctttttgg agatatactt ggtgttggtt gtgttttttg | 4260 |
| gttccttttc agagaactgt aaaccgaggc tgacgtgctc cactgactgt gccgaggggc | 4320 |
| gggggcagga ggacggcaag acctatttat aatatttagc gaactcggtc tccctcagat | 4380 |
| ccccccgcgag ggaggctgct ggacccaccc cgctgtcccc catgatagaa gtctgtaaat | 4440 |

```
acct tggtga ccaatgccca cttccctcc tgggtcacct ctgatggctg ctgtccactg    4500
agaacgtggg cagtgtccaa attcctgtac tgtaaagact aaaaggcgtt tgctctgaga    4560
ctgacaaggc ggaaacttcc atgtgtctcc tgccaggctc tgtcccccta cgccatcccg    4620
acacgtcccc gttcccccga aacctggctc agtgcaatac tcccattgcc atggggtcct    4680
tcaccatggt actgtctcca cagccctcag tccccacccc aggagaggcg cctgccacct    4740
cctcctcatc tccggtggtt caatcgctcc gcctgtcccc aacccagtcc cattttatg     4800 gccaaactga ttctgaaaca aaatgaaact gcaaacctcg tgtgtcttaa ctcccccag     4860 ggatgccact ccattcctcc gccccgtggt ctggtgcgtg caatccaaa gcgccgagac     4920 gagggtgctg tgtccctcaa acccagagtg gtgggcgcct ctgaaaccat acagccactc   4980
ctggccccaa acactggttt gcatcccagg ttcctcgccc acctacccc gccacacccc    5040 gtcttttag agatctctct aataaatcgg gtaataagca tc                      5082
```

<210> SEQ ID NO 30
<211> LENGTH: 700
<212> TYPE: PRT
<213> ORGANISM: homo sapiens

<400> SEQUENCE: 30

```
Met Glu Leu Glu Val Pro Asp Glu Ala Glu Ser Ala Glu Ala Gly Ala
1               5                   10                  15

Val Pro Ser Glu Ala Ala Trp Ala Ala Glu Ser Gly Ala Ala Ala Gly
            20                  25                  30

Leu Ala Gln Lys Lys Ala Ala Pro Thr Glu Val Leu Ser Met Thr Ala
        35                  40                  45

Gln Pro Gly Pro Gly His Gly Lys Lys Leu Gly His Arg Gly Val Asp
    50                  55                  60

Ala Ser Gly Glu Thr Thr Tyr Lys Lys Thr Thr Ser Ser Thr Leu Lys
65                  70                  75                  80

Gly Ala Ile Gln Leu Gly Ile Gly Tyr Thr Val Gly His Leu Ser Ser
                85                  90                  95

Lys Pro Glu Arg Asp Val Leu Met Gln Asp Phe Tyr Val Val Glu Ser
            100                 105                 110

Ile Phe Phe Pro Ser Glu Gly Ser Asn Leu Thr Pro Ala His His Phe
        115                 120                 125

Gln Asp Phe Arg Phe Lys Thr Tyr Ala Pro Val Ala Phe Arg Tyr Phe
    130                 135                 140

Arg Glu Leu Phe Gly Ile Arg Pro Asp Asp Tyr Leu Tyr Ser Leu Cys
145                 150                 155                 160

Asn Glu Pro Leu Ile Glu Leu Ser Asn Pro Gly Ala Ser Gly Ser Leu
                165                 170                 175

Phe Tyr Val Thr Ser Asp Asp Glu Phe Ile Ile Lys Thr Val Met His
            180                 185                 190

Lys Glu Ala Glu Phe Leu Gln Lys Leu Leu Pro Gly Tyr Tyr Met Asn
        195                 200                 205

Leu Asn Gln Asn Pro Arg Thr Leu Leu Pro Lys Phe Tyr Gly Leu Tyr
    210                 215                 220

Cys Val Gln Ser Gly Gly Lys Asn Ile Arg Val Val Met Asn Asn
225                 230                 235                 240

Ile Leu Pro Arg Val Val Lys Met His Leu Lys Phe Asp Leu Lys Gly
                245                 250                 255
```

-continued

```
Ser Thr Tyr Lys Arg Arg Ala Ser Lys Lys Glu Lys Glu Lys Ser Phe
            260                 265                 270

Pro Thr Tyr Lys Asp Leu Asp Phe Met Gln Asp Met Pro Glu Gly Leu
            275                 280                 285

Leu Leu Asp Ala Asp Thr Phe Ser Ala Leu Val Lys Thr Leu Gln Arg
        290                 295                 300

Asp Cys Leu Val Leu Glu Ser Phe Lys Ile Met Asp Tyr Ser Leu Leu
305                 310                 315                 320

Leu Gly Val His Asn Ile Asp Gln His Glu Arg Glu Arg Gln Ala Gln
                325                 330                 335

Gly Ala Gln Ser Thr Ser Asp Glu Lys Arg Pro Val Gly Gln Lys Ala
            340                 345                 350

Leu Tyr Ser Thr Ala Met Glu Ser Ile Gln Gly Gly Ala Ala Arg Gly
            355                 360                 365

Glu Ala Ile Glu Ser Asp Asp Thr Met Gly Gly Ile Pro Ala Val Asn
        370                 375                 380

Gly Arg Gly Glu Arg Leu Leu His Ile Gly Ile Asp Ile Leu
385                 390                 395                 400

Gln Ser Tyr Arg Phe Ile Lys Lys Leu Glu His Thr Trp Lys Ala Leu
                405                 410                 415

Val His Asp Gly Asp Thr Val Ser Val His Arg Pro Ser Phe Tyr Ala
            420                 425                 430

Glu Arg Phe Phe Lys Phe Met Ser Asn Thr Val Phe Arg Lys Asn Ser
        435                 440                 445

Ser Leu Lys Ser Ser Pro Ser Lys Lys Gly Arg Gly Gly Ala Leu Leu
    450                 455                 460

Ala Val Lys Pro Leu Gly Pro Thr Ala Ala Phe Ser Ala Ser Gln Ile
465                 470                 475                 480

Pro Ser Glu Arg Glu Glu Ala Gln Tyr Asp Leu Arg Gly Ala Arg Ser
                485                 490                 495

Tyr Pro Thr Leu Glu Asp Glu Gly Arg Pro Asp Leu Leu Pro Cys Thr
            500                 505                 510

Pro Pro Ser Phe Glu Glu Ala Thr Thr Ala Ser Ile Ala Thr Thr Leu
        515                 520                 525

Ser Ser Thr Ser Leu Ser Ile Pro Glu Arg Ser Pro Ser Glu Thr Ser
    530                 535                 540

Glu Gln Pro Arg Tyr Arg Arg Thr Gln Ser Ser Gly Gln Asp Gly
545                 550                 555                 560

Arg Pro Gln Glu Glu Pro Pro Ala Glu Glu Asp Leu Gln Gln Ile Thr
                565                 570                 575

Val Gln Val Glu Pro Ala Cys Ser Val Glu Ile Val Val Pro Lys Glu
            580                 585                 590

Glu Asp Ala Gly Val Glu Ala Ser Pro Ala Gly Ala Ser Ala Ala Val
        595                 600                 605

Glu Val Glu Thr Ala Ser Gln Ala Ser Asp Glu Glu Gly Ala Pro Ala
    610                 615                 620

Ser Gln Ala Ser Asp Glu Glu Asp Ala Pro Thr Asp Ile Tyr Phe
625                 630                 635                 640

Trp Arg Leu Trp Gly Pro His Ala Pro Thr Trp Pro Trp Arg Arg Glu
                645                 650                 655

Gly Arg Ala Ala Cys Leu Cys Pro Tyr Pro Pro His Val Val Thr Pro
            660                 665                 670

Phe Pro Gly Thr Gly Leu Cys Ala Ser Trp Ser Pro Asp Gly Thr Gly
```

```
            675                 680                 685
Gly Leu Gly Ala Met Ser Cys Cys Val Ser Val Ser
    690                 695                 700

<210> SEQ ID NO 31
<211> LENGTH: 3471
<212> TYPE: DNA
<213> ORGANISM: homo sapiens

<400> SEQUENCE: 31
gcgcgccctc ccttggccgg cggcgcttgt tgttcggcgg cggcggtcgc agctcgggtc      60
cccctcgggc gccccgccg ccgtccgcgc gcggccatgg agctggaggt accggacgag     120
gcggagagcg ctgaggcggg ggccgtgccc tcggaggcgg cgtgggcggc agagagcggg     180
gcggcggcag gtttggctca gaagaaggcg gccccaacag aggttctgtc catgacggca     240
cagccgggcc ctggccatgg gaagaagttg ggccatcgag gtgtggacgc atccggcgaa     300
accacctaca agaagaccac ctcctccacc ctgaagggtg ccatccagct ggcatcggc     360 tacaccgtgg gccacctgag ctccaagccc gaacgcgacg tgctcatgca ggacttctac     420
gtggtggaga gcatcttctt ccccagcgaa ggcagcaacc tcaccccgc ccaccacttc     480 caggacttcc gcttcaagac ctatgcacct gtcgccttcc gctacttccg ggagctcttt     540
gggatccggc cagatgatta cttgtactcc ctgtgcaatg agccgctgat cgagctgtcc     600
aacccgggcg ccagtggctc cctcttctac gtcaccagcg acgacgagtt catcatcaag     660
accgtcatgc acaaggaggc cgagttcctg cagaagctgc tccctggcta ctacatgaac     720
ctcaaccaga acccgcggac gctgctgccc aagttctatg ggctgtactg cgtgcagtcg     780
gggggcaaga acatccgcgt cgtggtcatg aacaacatcc tgccccgcgt ggtcaagatg     840
cacctcaagt tcgacctcaa gggctccacc tacaagcggc gcgccagcaa gaaggagaag     900
gagaagagct tccccaccta caaggacctg gacttcatgc aggacatgcc cgaggggctc     960
ctgctggacg ccgacacctt cagcgccctg gtcaagacgc tgcagcggga ctgcctggtc    1020
ctggaaagtt tcaagatcat ggactacagc ctgctgctgg gcgtgcacaa catcgaccag    1080
cacgagcgcg agcggcaggc gcagggcgcc cagagcacct cagatgagaa gcggcctgtg    1140
ggccagaagg cgctctactc cacggccatg agtccatcc agggtggcgc gcgcgcgggg    1200
gaggccatcg aatcggatga cacgatgggc gggatccccg ctgtgaacgg ccgcggggag    1260
cggctgctgc tgcacattgg catcatcgac atcctgcagt cctacaggtt catcaagaaa    1320
ctggagcaca cctggaaggc cctcgtccac gatgggggaca cggtgtccgt ccaccgcccc    1380
agcttctatg ccgagcgctt tttcaagttc atgagcaaca cggtctttcg gaagaactcc    1440
tccctgaagt cctcgccctc caagaagggg cgcggcggag ccttgctagc tgtgaaaccg    1500
ctggggccca ccgctgcctt ctcggccagc cagatccta gcgagcggga ggaggcccag    1560
tacgacctgc gggggccccg cagctacccc acgctggagg acgaaggccg gcccgacctc    1620
ctgccctgca cgccaccttc tttcgaagaa gccactacag cctccattgc cacgactctg    1680
tcatccacat ccctctccat tcctgagcgg tccccctcgg agacgtcgga gcagccgcgg    1740
tacaggcggc gcacacagtc gtctggacag gatggcaggc gcaggagga ccacccgcg    1800 gaagaggatc tgcagcagat tacagtgcag gtggagcctg cgtgcagcgt ggagattgtg    1860
gtccccaaag aggaggacgc aggggtggag cttcccccgg ccggtgcctc tgctgctgtt    1920
gaagtagaaa ctgccagcca ggcctcagac gaggagggcg cacctgccag ccaggcctcg    1980
```

```
gacgaggagg acgcgcccgc caccgacatc tactttttca cggatgggag gtactggatt    2040
tactctcccc gccatcgccg actgcgggcc gtgacgctga gcgcctcggg gactgtaagt    2100
gaccgcagcc ggccacccctg gggagaaggg gcagtgcccc tcgggcagca gggagccgca    2160
ggtccccggc cggaagctca gtgtctgacg tcagttgttt tccagaaggg ctttgggtaa    2220
atcacggctg caattgaggt cagccacgct ggccccggac caggcgctgg gctgcatgcg    2280
tcactgggaa tgtcattcgg tcccacgtcg aaccggcgc tccataggc agcaccatca    2340 ccaggtgcac agctgaggcc cagggtctgc ttcggacccc ggccagaccc cagcgagccc    2400
ctctctgccc ctggacccag ccctctcgtg tcagggtgtc ttgggtggac gcttctcact    2460
cgtgcagacc tggctgcccg tggccccgct ggctgcacag gggaggttgc acaggtcagc    2520
agagtggctg cagggccggg ctctgaaccg cagggccatg gagacgggga ggagatggtc    2580
tctccacacc cacctcacag atggaggcgc tgaggcctcg gctcccctgg gagcctggga    2640
gaccacacgg tttagtcaaa atccagatcc ccaagctctc aaggaggtcc ccctgggacg    2700
ccacatgggc cccacgtagc tgtgagatcc tcagggcctg ctgttgtcat tatgaccaat    2760
aagcaagggg cccagagagc ctaagagacc tgcccagcac cgcacagcca aacggggcg    2820 cagacccaaa gcaggagtgt cccctcgaga caaagcctcc gccgaggccg ccgtgactcc    2880
ccgcccatca gcaaacctct ccgagcacct ctgtgtgcca ggcactgtgg agtgaccccca    2940 agaggtggag accacttccc cggctgctct aggcagctcc gtcccacgga ccagcggga    3000 agccagccac cgcgaagccg tgccccggag atcgtccagg agctgcccag aggggcctgc    3060 tgggaggag agcactggag agacccagcg gccctgctgg ccaccccacc ataggcaggg    3120
agcagttcgc agaggccgcc tacggagggg ggtgcttgga ctttgaaaaa cacctgactt    3180
gaaggggcag acgtggggag ggtggtctcg gcagcaggca cagcagaagc ggaagtgtgg    3240
gggccagaag ggaggcaggg cagccattga aagcacccca aggcctgagt gctgaagagg    3300 ctgtgcccctt ggttctggtc ttcctggggt cacccggttc tgggtcccag ctgctactgc    3360
cccccacttc ccctgtctgc ccagctgctg gctgagggtg tccctctctg tcccccccaac    3420 tcctgcagga caaggaagcc acctgtcctg ccctttcttt tttttcattt t             3471
```

<210> SEQ ID NO 32
<211> LENGTH: 707
<212> TYPE: PRT
<213> ORGANISM: homo sapiens

<400> SEQUENCE: 32

```
Met Glu Leu Glu Val Pro Asp Glu Ala Glu Ser Ala Glu Ala Gly Ala
1               5                   10                  15

Val Pro Ser Glu Ala Ala Trp Ala Ala Glu Ser Gly Ala Ala Ala Gly
            20                  25                  30

Leu Ala Gln Lys Lys Ala Ala Pro Thr Glu Val Leu Ser Met Thr Ala
        35                  40                  45

Gln Pro Gly Pro Gly His Gly Lys Lys Leu Gly His Arg Gly Val Asp
    50                  55                  60

Ala Ser Gly Glu Thr Thr Tyr Lys Lys Thr Thr Ser Ser Thr Leu Lys
65                  70                  75                  80

Gly Ala Ile Gln Leu Gly Ile Gly Tyr Thr Val Gly His Leu Ser Ser
                85                  90                  95

Lys Pro Glu Arg Asp Val Leu Met Gln Asp Phe Tyr Val Val Glu Ser
                100                 105                 110
```

-continued

```
Ile Phe Phe Pro Ser Glu Gly Ser Asn Leu Thr Pro Ala His His Phe
            115                 120                 125

Gln Asp Phe Arg Phe Lys Thr Tyr Ala Pro Val Ala Phe Arg Tyr Phe
            130                 135                 140

Arg Glu Leu Phe Gly Ile Arg Pro Asp Asp Tyr Leu Tyr Ser Leu Cys
145                 150                 155                 160

Asn Glu Pro Leu Ile Glu Leu Ser Asn Pro Gly Ala Ser Gly Ser Leu
                165                 170                 175

Phe Tyr Val Thr Ser Asp Asp Glu Phe Ile Ile Lys Thr Val Met His
                180                 185                 190

Lys Glu Ala Glu Phe Leu Gln Lys Leu Leu Pro Gly Tyr Tyr Met Asn
                195                 200                 205

Leu Asn Gln Asn Pro Arg Thr Leu Leu Pro Lys Phe Tyr Gly Leu Tyr
            210                 215                 220

Cys Val Gln Ser Gly Gly Lys Asn Ile Arg Val Val Met Asn Asn
225                 230                 235                 240

Ile Leu Pro Arg Val Val Lys Met His Leu Lys Phe Asp Leu Lys Gly
                245                 250                 255

Ser Thr Tyr Lys Arg Arg Ala Ser Lys Lys Glu Lys Glu Lys Ser Phe
                260                 265                 270

Pro Thr Tyr Lys Asp Leu Asp Phe Met Gln Asp Met Pro Glu Gly Leu
            275                 280                 285

Leu Leu Asp Ala Asp Thr Phe Ser Ala Leu Val Lys Thr Leu Gln Arg
            290                 295                 300

Asp Cys Leu Val Leu Glu Ser Phe Lys Ile Met Asp Tyr Ser Leu Leu
305                 310                 315                 320

Leu Gly Val His Asn Ile Asp Gln His Glu Arg Glu Arg Gln Ala Gln
                325                 330                 335

Gly Ala Gln Ser Thr Ser Asp Glu Lys Arg Pro Val Gly Gln Lys Ala
            340                 345                 350

Leu Tyr Ser Thr Ala Met Glu Ser Ile Gln Gly Gly Ala Ala Arg Gly
            355                 360                 365

Glu Ala Ile Glu Ser Asp Asp Thr Met Gly Gly Ile Pro Ala Val Asn
370                 375                 380

Gly Arg Gly Glu Arg Leu Leu Leu His Ile Gly Ile Asp Ile Leu
385                 390                 395                 400

Gln Ser Tyr Arg Phe Ile Lys Lys Leu Glu His Thr Trp Lys Ala Leu
                405                 410                 415

Val His Asp Gly Asp Thr Val Ser Val His Arg Pro Ser Phe Tyr Ala
            420                 425                 430

Glu Arg Phe Phe Lys Phe Met Ser Asn Thr Val Phe Arg Lys Asn Ser
            435                 440                 445

Ser Leu Lys Ser Ser Pro Ser Lys Lys Gly Arg Gly Gly Ala Leu Leu
            450                 455                 460

Ala Val Lys Pro Leu Gly Pro Thr Ala Ala Phe Ser Ala Ser Gln Ile
465                 470                 475                 480

Pro Ser Glu Arg Glu Glu Ala Gln Tyr Asp Leu Arg Gly Ala Arg Ser
                485                 490                 495

Tyr Pro Thr Leu Glu Asp Glu Gly Arg Pro Asp Leu Leu Pro Cys Thr
            500                 505                 510

Pro Pro Ser Phe Glu Glu Ala Thr Thr Ala Ser Ile Ala Thr Thr Leu
            515                 520                 525

Ser Ser Thr Ser Leu Ser Ile Pro Glu Arg Ser Pro Ser Glu Thr Ser
```

-continued

```
            530                 535                 540
Glu Gln Pro Arg Tyr Arg Arg Thr Gln Ser Ser Gly Gln Asp Gly
545                 550                 555                 560

Arg Pro Gln Glu Glu Pro Ala Glu Asp Leu Gln Gln Ile Thr
                565                 570                 575

Val Gln Val Glu Pro Ala Cys Ser Val Glu Ile Val Val Pro Lys Glu
                580                 585                 590

Glu Asp Ala Gly Val Glu Ala Ser Pro Ala Gly Ala Ser Ala Ala Val
            595                 600                 605

Glu Val Glu Thr Ala Ser Gln Ala Ser Asp Glu Glu Gly Ala Pro Ala
            610                 615                 620

Ser Gln Ala Ser Asp Glu Glu Asp Ala Pro Ala Thr Asp Ile Tyr Phe
625                 630                 635                 640

Phe Thr Asp Gly Arg Tyr Trp Ile Tyr Ser Pro Arg His Arg Arg Leu
                645                 650                 655

Arg Ala Val Thr Leu Ser Ala Ser Gly Thr Val Ser Asp Arg Ser Arg
                660                 665                 670

Pro Pro Trp Gly Glu Gly Ala Val Pro Leu Gly Gln Gln Gly Ala Ala
                675                 680                 685

Gly Pro Arg Pro Glu Ala Gln Cys Leu Thr Ser Val Val Phe Gln Lys
                690                 695                 700

Gly Phe Gly
705

<210> SEQ ID NO 33
<211> LENGTH: 640
<212> TYPE: PRT
<213> ORGANISM: homo sapiens

<400> SEQUENCE: 33

Met Glu Leu Glu Val Pro Asp Glu Ala Glu Ser Ala Glu Ala Gly Ala
1               5                   10                  15

Val Pro Ser Glu Ala Ala Trp Ala Ala Glu Ser Gly Ala Ala Ala Gly
                20                  25                  30

Leu Ala Gln Lys Lys Ala Ala Pro Thr Glu Val Leu Ser Met Thr Ala
            35                  40                  45

Gln Pro Gly Pro Gly His Gly Lys Lys Leu Gly His Arg Gly Val Asp
        50                  55                  60

Ala Ser Gly Glu Thr Thr Tyr Lys Lys Thr Thr Ser Ser Thr Leu Lys
65                  70                  75                  80

Gly Ala Ile Gln Leu Gly Ile Gly Tyr Thr Val Gly His Leu Ser Ser
                85                  90                  95

Lys Pro Glu Arg Asp Val Leu Met Gln Asp Phe Tyr Val Val Glu Ser
                100                 105                 110

Ile Phe Phe Pro Ser Glu Gly Ser Asn Leu Thr Pro Ala His His Phe
            115                 120                 125

Gln Asp Phe Arg Phe Lys Thr Tyr Ala Pro Val Ala Phe Arg Tyr Phe
        130                 135                 140

Arg Glu Leu Phe Gly Ile Arg Pro Asp Asp Tyr Leu Tyr Ser Leu Cys
145                 150                 155                 160

Asn Glu Pro Leu Ile Glu Leu Ser Asn Pro Gly Ala Ser Gly Ser Leu
                165                 170                 175

Phe Tyr Val Thr Ser Asp Asp Glu Phe Ile Ile Lys Thr Val Met His
                180                 185                 190
```

-continued

Lys Glu Ala Glu Phe Leu Gln Lys Leu Leu Pro Gly Tyr Tyr Met Asn
        195                 200                 205
Leu Asn Gln Asn Pro Arg Thr Leu Leu Pro Lys Phe Tyr Gly Leu Tyr
    210                 215                 220
Cys Val Gln Ser Gly Gly Lys Asn Ile Arg Val Val Met Asn Asn
225                 230                 235                 240
Ile Leu Pro Arg Val Val Lys Met His Leu Lys Phe Asp Leu Lys Gly
                245                 250                 255
Ser Thr Tyr Lys Arg Arg Ala Ser Lys Glu Lys Glu Lys Ser Phe
            260                 265                 270
Pro Thr Tyr Lys Asp Leu Asp Phe Met Gln Asp Met Pro Glu Gly Leu
        275                 280                 285
Leu Leu Asp Ala Asp Thr Phe Ser Ala Leu Val Lys Thr Leu Gln Arg
    290                 295                 300
Asp Cys Leu Val Leu Glu Ser Phe Lys Ile Met Asp Tyr Ser Leu Leu
305                 310                 315                 320
Leu Gly Val His Asn Ile Asp Gln His Glu Arg Glu Arg Gln Ala Gln
                325                 330                 335
Gly Ala Gln Ser Thr Ser Asp Glu Lys Arg Pro Val Gly Gln Lys Ala
            340                 345                 350
Leu Tyr Ser Thr Ala Met Glu Ser Ile Gln Gly Gly Ala Ala Arg Gly
        355                 360                 365
Glu Ala Ile Glu Ser Asp Asp Thr Met Gly Gly Ile Pro Ala Val Asn
    370                 375                 380
Gly Arg Gly Glu Arg Leu Leu His Ile Gly Ile Asp Ile Leu
385                 390                 395                 400
Gln Ser Tyr Arg Phe Ile Lys Lys Leu Glu His Thr Trp Lys Ala Leu
                405                 410                 415
Val His Asp Gly Asp Thr Val Ser Val His Arg Pro Ser Phe Tyr Ala
            420                 425                 430
Glu Arg Phe Phe Lys Phe Met Ser Asn Thr Val Phe Arg Lys Asn Ser
        435                 440                 445
Ser Leu Lys Ser Ser Pro Ser Lys Lys Gly Arg Gly Gly Ala Leu Leu
    450                 455                 460
Ala Val Lys Pro Leu Gly Pro Thr Ala Ala Phe Ser Ala Ser Gln Ile
465                 470                 475                 480
Pro Ser Glu Arg Glu Glu Ala Gln Tyr Asp Leu Arg Gly Ala Arg Ser
                485                 490                 495
Tyr Pro Thr Leu Glu Asp Glu Gly Arg Pro Asp Leu Leu Pro Cys Thr
            500                 505                 510
Pro Pro Ser Phe Glu Glu Ala Thr Thr Ala Ser Ile Ala Thr Thr Leu
        515                 520                 525
Ser Ser Thr Ser Leu Ser Ile Pro Glu Arg Ser Pro Ser Glu Thr Ser
    530                 535                 540
Glu Gln Pro Arg Tyr Arg Arg Thr Gln Ser Ser Gly Gln Asp Gly
545                 550                 555                 560
Arg Pro Gln Glu Glu Pro Pro Ala Glu Asp Leu Gln Gln Ile Thr
                565                 570                 575
Val Gln Val Glu Pro Ala Cys Ser Glu Ile Val Val Pro Lys Glu
            580                 585                 590
Glu Asp Ala Gly Val Glu Ala Ser Pro Ala Gly Ala Ser Ala Ala Val
        595                 600                 605
Glu Val Glu Thr Ala Ser Gln Ala Ser Asp Glu Glu Gly Ala Pro Ala

```
                    610                 615                 620
Ser Gln Ala Ser Asp Glu Glu Asp Ala Pro Ala Thr Asp Ile Tyr Phe
625                 630                 635                 640
```

<210> SEQ ID NO 34
<211> LENGTH: 2724
<212> TYPE: DNA
<213> ORGANISM: homo sapiens

<400> SEQUENCE: 34

| | | | | | |
|---|---|---|---|---|---|
| gcgcgccctc | ccttggccgg | cggcgcttgt | tgttcggcgg | cggcggtcgc | agctcgggtc | 60 |
| cccctcgggc | gccccccgccg | ccgtccgcgc | gcggccatgg | agctggaggt | accggacgag | 120 |
| gcggagagcg | ctgaggcggg | ggccgtgccc | tcggaggcgg | cgtgggcggc | agagagcggg | 180 |
| gcggcggcag | gtttggctca | gaagaaggcg | gccccaacag | aggttctgtc | catgacggca | 240 |
| cagccgggcc | ctggccatgg | gaagaagttg | ggccatcgag | gtgtggacgc | atccggcgaa | 300 |
| accacctaca | agaagaccac | ctcctccacc | ctgaagggtg | ccatccagct | gggcatcggc | 360 |
| tacaccgtgg | gccacctgag | ctccaagccc | gaacgcgacg | tgctcatgca | ggacttctac | 420 |
| gtggtgagag | gcatcttctt | ccccagcgaa | ggcagcaacc | tcacccccgc | ccaccacttc | 480 |
| caggacttcc | gcttcaagac | ctatgcacct | gtcgccttcc | gctacttccg | ggagctcttt | 540 |
| gggatccggc | cagatgatta | cttgtactcc | ctgtgcaatg | agccgctgat | cgagctgtcc | 600 |
| aacccgggcg | ccagtggctc | cctcttctac | gtcaccagcg | acgacgagtt | catcatcaag | 660 |
| accgtcatgc | acaaggaggc | cgagttcctg | cagaagctgc | tccctggcta | ctacatgaac | 720 |
| ctcaaccaga | acccgcggac | gctgctgccc | aagttctatg | ggctgtactg | cgtgcagtcg | 780 |
| ggggcaaga | acatccgcgt | cgtggtcatg | aacaacatcc | tgccccgcgt | ggtcaagatg | 840 |
| cacctcaagt | tcgacctcaa | gggctccacc | tacaagcggc | gcgccagcaa | gaaggagaag | 900 |
| gagaagagct | tccccaccta | caaggacctg | acttcatgc | aggacatgcc | cgaggggctc | 960 |
| ctgctggacg | ccgacacctt | cagcgccctg | gtcaagacgc | tgcagcggga | ctgcctggtc | 1020 |
| ctggaaagtt | tcaagatcat | ggactacagc | ctgctgctgg | gcgtgcacaa | catcgaccag | 1080 |
| cacgagcgcg | agcggcaggc | gcagggcgcc | cagagcacct | cagatgagaa | gcggcctgtg | 1140 |
| ggccagaagg | cgctctactc | cacggccatg | gagtccatcc | agggtggcgc | cgcgcgcggg | 1200 |
| gaggccatcg | aatcggatga | cacgatgggc | gggatccccg | ctgtgaacgg | ccgcggggag | 1260 |
| cggctgctgc | tgcacattgg | catcatcgac | atcctgcagt | cctacaggtt | catcaagaaa | 1320 |
| ctggagcaca | cctggaaggc | cctcgtccac | gatgggggaca | cggtgtccgt | ccaccgcccc | 1380 |
| agcttctatg | ccgagcgctt | tttcaagttc | atgagcaaca | cggtctttcg | gaagaactcc | 1440 |
| tccctgaagt | cctcgccctc | caagaagggg | gcggcggag | ccttgctagc | tgtgaaaccg | 1500 |
| ctggggccca | ccgctgcctt | ctcggccagc | cagatcccta | gcgagcggga | ggaggcccag | 1560 |
| tacgacctgc | gggggggccg | cagctacccc | acgctggagg | acgaaggccg | gcccgacctc | 1620 |
| ctgccctgca | cgccaccttc | tttcgaagaa | gccactacag | cctccattgc | cacgactctg | 1680 |
| tcatccacat | ccctctccat | tcctgagcgg | tccccctcgg | agacgtcgga | gcagccgcgg | 1740 |
| tacaggccgc | aggaggagcc | acccgcgaa | gaggatctgc | agcagattac | agtgcaggtg | 1800 |
| gagcctgcgt | gcagcgtgga | gattgtggtc | cccaaagagg | aggacgcagg | ggtggaggct | 1860 |
| tccccggccg | gtgcctctgc | tgctgttgaa | gtagaaactg | ccagccaggc | ctcagacgag | 1920 |
| gagggcgcac | ctgccagcca | ggcctcggac | gaggaggacg | cgcccgccac | cgacatctac | 1980 |

-continued

```
tttttcacgg atggaggta ctggatttac tctccccgcc atcgccgact gcgggccgtg    2040
acgctgagcg cctcggggac tgtaagtgac cgcagccggc caccctgggg agaagggca    2100
gtgcccctcg ggcagcaggg agccgcaggt ccccggccgg aagctcagtg tctgacgtca    2160
gttgttttcc agaagggctt tgggtaaatc acggctgcaa ttgaggtcag ccacgctggc    2220
cccggaccag gcgctgggct gcatgcgtca ctgggaatgt cattcggtcc cacgtcgaac    2280
cgggcgctcc ataggcagc accatcacca ggtgcacagc tgaggcccag ggtctgcttc    2340
ggacccggc cagacccag cgagccctc tctgccctg acccagccc tctcgtgtca         2400
gggtgtcttg ggtggacgct tctcactcgt gcagacctgg ctgccgtgg ccccgctggc    2460
tgcacaggg aggttgcaca ggtcagcaga gtggctgcag gccgggctc tgaaccgcag      2520
ggccatggag acgggagga gatggtctct ccacacccac ctcacagatg gaggcgctga    2580
ggcctcggct ccctgggag cctgggagac cacacggttt agtcaaaatc cagatcccca    2640
agctctcaag gaggtccccc tgggacgcca catgggcccc acgtagctgt gagatcctca    2700
gggcctgctg ttgtcattat gacc                                          2724
```

```
<210> SEQ ID NO 35
<211> LENGTH: 696
<212> TYPE: PRT
<213> ORGANISM: homo sapiens

<400> SEQUENCE: 35

Met Glu Leu Glu Val Pro Asp Glu Ala Glu Ser Ala Glu Ala Gly Ala
1               5                   10                  15

Val Pro Ser Glu Ala Ala Trp Ala Glu Ser Gly Ala Ala Gly
            20                  25                  30

Leu Ala Gln Lys Lys Ala Ala Pro Thr Glu Val Leu Ser Met Thr Ala
            35                  40                  45

Gln Pro Gly Pro Gly His Gly Lys Lys Leu Gly His Arg Gly Val Asp
        50                  55                  60

Ala Ser Gly Glu Thr Thr Tyr Lys Lys Thr Thr Ser Ser Thr Leu Lys
65                  70                  75                  80

Gly Ala Ile Gln Leu Gly Ile Gly Tyr Thr Val Gly His Leu Ser Ser
                85                  90                  95

Lys Pro Glu Arg Asp Val Leu Met Gln Asp Phe Tyr Val Val Glu Ser
            100                 105                 110

Ile Phe Phe Pro Ser Glu Gly Ser Asn Leu Thr Pro Ala His His Phe
        115                 120                 125

Gln Asp Phe Arg Phe Lys Thr Tyr Ala Pro Val Ala Phe Arg Tyr Phe
    130                 135                 140

Arg Glu Leu Phe Gly Ile Arg Pro Asp Asp Tyr Leu Tyr Ser Leu Cys
145                 150                 155                 160

Asn Glu Pro Leu Ile Glu Leu Ser Asn Pro Gly Ala Ser Gly Ser Leu
                165                 170                 175

Phe Tyr Val Thr Ser Asp Asp Glu Phe Ile Ile Lys Thr Val Met His
            180                 185                 190

Lys Glu Ala Glu Phe Leu Gln Lys Leu Leu Pro Gly Tyr Tyr Met Asn
        195                 200                 205

Leu Asn Gln Asn Pro Arg Thr Leu Leu Pro Lys Phe Tyr Gly Leu Tyr
    210                 215                 220

Cys Val Gln Ser Gly Gly Lys Asn Ile Arg Val Val Val Met Asn Asn
225                 230                 235                 240
```

```
Ile Leu Pro Arg Val Lys Met His Leu Lys Phe Asp Leu Lys Gly
            245                 250                 255

Ser Thr Tyr Lys Arg Arg Ala Ser Lys Lys Glu Lys Glu Lys Ser Phe
        260                 265                 270

Pro Thr Tyr Lys Asp Leu Asp Phe Met Gln Asp Met Pro Glu Gly Leu
        275                 280                 285

Leu Leu Asp Ala Asp Thr Phe Ser Ala Leu Val Lys Thr Leu Gln Arg
290                 295                 300

Asp Cys Leu Val Leu Glu Ser Phe Lys Ile Met Asp Tyr Ser Leu Leu
305                 310                 315                 320

Leu Gly Val His Asn Ile Asp Gln His Glu Arg Glu Arg Gln Ala Gln
                325                 330                 335

Gly Ala Gln Ser Thr Ser Asp Glu Lys Arg Pro Val Gly Gln Lys Ala
                340                 345                 350

Leu Tyr Ser Thr Ala Met Glu Ser Ile Gln Gly Gly Ala Ala Arg Gly
                355                 360                 365

Glu Ala Ile Glu Ser Asp Asp Thr Met Gly Gly Ile Pro Ala Val Asn
            370                 375                 380

Gly Arg Gly Glu Arg Leu Leu Leu His Ile Gly Ile Ile Asp Ile Leu
385                 390                 395                 400

Gln Ser Tyr Arg Phe Ile Lys Lys Leu Glu His Thr Trp Lys Ala Leu
                405                 410                 415

Val His Asp Gly Asp Thr Val Ser Val His Arg Pro Ser Phe Tyr Ala
                420                 425                 430

Glu Arg Phe Phe Lys Phe Met Ser Asn Thr Val Phe Arg Lys Asn Ser
            435                 440                 445

Ser Leu Lys Ser Ser Pro Ser Lys Lys Gly Arg Gly Gly Ala Leu Leu
        450                 455                 460

Ala Val Lys Pro Leu Gly Pro Thr Ala Ala Phe Ser Ala Ser Gln Ile
465                 470                 475                 480

Pro Ser Glu Arg Glu Glu Ala Gln Tyr Asp Leu Arg Gly Ala Arg Ser
                485                 490                 495

Tyr Pro Thr Leu Glu Asp Glu Gly Arg Pro Asp Leu Leu Pro Cys Thr
        500                 505                 510

Pro Pro Ser Phe Glu Glu Ala Thr Thr Ala Ser Ile Ala Thr Thr Leu
        515                 520                 525

Ser Ser Thr Ser Leu Ser Ile Pro Glu Arg Ser Pro Ser Glu Thr Ser
530                 535                 540

Glu Gln Pro Arg Tyr Arg Pro Gln Glu Glu Pro Pro Ala Glu Glu Asp
545                 550                 555                 560

Leu Gln Gln Ile Thr Val Gln Val Glu Pro Ala Cys Ser Val Glu Ile
                565                 570                 575

Val Val Pro Lys Glu Glu Asp Ala Gly Val Glu Ala Ser Pro Ala Gly
            580                 585                 590

Ala Ser Ala Ala Val Glu Val Ser Thr Ala Ser Gln Ala Ser Asp Glu
                595                 600                 605

Glu Gly Ala Pro Ala Ser Gln Ala Ser Asp Glu Glu Asp Ala Pro Ala
        610                 615                 620

Thr Asp Ile Tyr Phe Phe Thr Asp Gly Arg Tyr Trp Ile Tyr Ser Pro
625                 630                 635                 640

Arg His Arg Arg Leu Arg Ala Val Thr Leu Ser Ala Ser Gly Thr Val
                645                 650                 655

Ser Asp Arg Ser Arg Pro Pro Trp Gly Glu Gly Ala Val Pro Leu Gly
```

|     |     |     |     |     |     |     |     |     |     |
| --- | --- | --- | --- | --- | --- | --- | --- | --- | --- |
|     |     | 660 |     |     | 665 |     |     | 670 |     |
| Gln | Gln | Gly | Ala | Ala | Gly | Pro | Arg | Pro | Glu | Ala | Gln | Cys | Leu | Thr | Ser |
|     |     | 675 |     |     |     |     | 680 |     |     |     |     | 685 |     |     |     |
| Val | Val | Phe | Gln | Lys | Gly | Phe | Gly |
|     |     | 690 |     |     |     |     | 695 |

<210> SEQ ID NO 36
<211> LENGTH: 5624
<212> TYPE: DNA
<213> ORGANISM: homo sapiens

<400> SEQUENCE: 36

```
agtcagtcgg ggagcaagag ccccgcgcgc agccggcgcg ggctcggtca tcggcgcgcc    60
gccgcccggg gctgggcttg gggctgcctg tggagaggcg gcgggcggaa cgcgcgcggc   120
cacggccacg gccaccgcca cggccacggc cggcagctcg ggtcccgggt cccgggcagg   180
ggaaggggag aggcggcgag ctcagcaacc ggaaccgagg gaagattttg gctccgcggg   240
ctcgccctcc gctccctctg ccagcggcgc cagacgccga gtggggccag ggacagggga   300
ggaggaccca ggaccctgtg cccgcgcccc tggagccgct ggagttcgga cttctgcaac   360
tgttggcact ttgggggctt ggcttagcgc tctgctgttt acccgtctct cctcgctgcc   420
tcggaaccaa agctcccggc ccctccgcc ctcgcgcgcc cacccaccgc cgccggggag   480
cggcccggcc cgcactcagc accatgaggg gacttggac ttgcctggcg actttggccg   540
gactttgct aactgcggcg ggcgagacgt tctcaggtgg ctgcctcttt gatgagccgt   600
atagcacatg tggatatagt caatctgaag gtgatgactt caattgggag caagtgaaca   660
ccttgactaa accgacttct gatccatgga tgccatcagg ttctttcatg ctggtgaatg   720
cctctgggag acctgagggg cagagagccc acctgctctt accccaactt aaagaaaatg   780
acacccactg catcgatttt cactattttg tgtccagcaa gagtaattct cctccggggt   840
tactcaatgt ctacgtgaag gtcaataacg gccactgggg gaatcctatc tggaatatat   900
ctggagaccc aacacgtaca tggaacaggg cagaactggc cattagtact ttctggccta   960
acttttatca ggtgattttt gaagtgataa cttctggaca tcaaggctat ctcgctatcg  1020
atgaggtgaa ggtgttagga catccatgta ccaggactcc tcacttcctg cggattcaga  1080
atgtggaagt taatgctggc cagttttgcta ccttccagtg cagtgccatc ggcaggaccg  1140
tggcaggaga caggctctgg ttacagggca ttgatgtgcg agatgctcct ctgaaggaaa  1200
tcaaggtgac cagctcccga cgcttcattg cttcatttaa tgttgtgaat accaccaaac  1260
gagatgctgg aaagtaccgc tgcatgattc gcactgaagg aggtgttgga atatcaaact  1320
atgcagagtt ggtagttaaa gaaccacccg ttcctattgc cccacctcag ctcgcctctg  1380
taggagccac ctacctgtgg atacagctca acgccaactc catcaatggg gatgggccca  1440
ttgtggcccg agaggtggag tactgcacgg ccagtgggag ctggaatgac ggcagccag  1500
tcgattccac gagctataaa attggacacc ttgacccaga tacagaatat gagattagtg  1560
tgctcctgac caggccaggg gagggtggca ctggctctcc tggtccagct ctcaggacaa  1620
gaacaaagtg tgctgatccc atgcgaggcc caagaaaact agaagtagtg gaggtcaaat  1680
ctcggcaaat cactatccgc tgggagccat ttggatataa tgtaactcgt tgccacagtt  1740
ataatctcac tgtccactac tgttaccaag ttggaggaca agaacaagtg cgagaagaag  1800
taagctggga tacagaaaac tcacaccctc aacacacgat cactaacctg tcaccataca  1860
ccaatgtcag tgtgaaactg atcctcatga acccagaggg ccggaaggaa agccaagaac  1920
```

| | |
|---|---|
| tcatagtgca gacagatgaa gacctcccag gtgctgttcc cactgaatcc atacaaggaa | 1980 |
| gtacctttga agagaagata tttcttcagt ggagagaacc aactcaaaca tatggtgtaa | 2040 |
| tcactttata tgagatcacc tacaaagcag tcagttcctt tgacccagaa atagatttat | 2100 |
| ccaatcagag tggaagagtt tcaaagctgg gaaatgaaac ccattttctg ttttttggac | 2160 |
| tgtatccggg gaccacatac tcctttacca tccgagctag cacagctaag ggttttgggc | 2220 |
| ctccagcaac aaaccagttc accaccaaaa tatcagcacc ctctatgcca gcttatgaac | 2280 |
| ttgagacacc tttgaatcaa actgacaata ccgtgacagt catgctgaaa cctgcccaca | 2340 |
| gcagaggagc acctgtcagt gtctatcaaa tagttgttga ggaagaacgt cctcgaagaa | 2400 |
| ctaaaaagac gacagaaatc ttaaagtgct acccagtgcc aattcacttc cagaatgctt | 2460 |
| ctctgctgaa ctcacagtac tactttgctg cagaatttcc tgcagacagc ctccaagctg | 2520 |
| cgcagccttt tacaattggt gataataaga catataatgg atactggaac actcccttc | 2580 |
| tccctataa aagctacaga atttatttcc aagctgctag tagagccaat ggggaaacca | 2640 |
| aaatagactg tgtccaagtg gccacaaaag gagctgccac tccgaaacca gtcccagaac | 2700 |
| ccgagaaaca gacagaccat acagttaaaa ttgctggagt catcgcgggc atcttgctgt | 2760 |
| tcgtgattat atttcttgga gttgtgttgg taatgaagaa aaggaaactg ccaagaagc | 2820 |
| ggaaagagac catgagcagc acccgacagg agatgactgt gatggtgaac tcaatggaca | 2880 |
| agagctatgc tgagcagggc acaaactgcg acgaggcttt ctcattcatg gacacgcaca | 2940 |
| atctgaatgg gagatctgtg tcttcaccat cgtccttcac aatgaaaaca aatacactga | 3000 |
| gcacatcggt gcctaattcc tattacccag acccatttgt gccaactgca attttagtgc | 3060 |
| caataaatga tgaaacccac acaatggcca gcgataccag cagcctggtg cagtcccata | 3120 |
| cttacaagaa gcgagagccg gccgacgtgc cctatcagac tgggcagctc caccccgcca | 3180 |
| tccgggtggc agacctcctt cagcacatca cacagatgaa gtgtgcggag ggctacggct | 3240 |
| tcaaggagga atacgagagc ttcttgaag gcagtctgc accatgggac tcggctaaga | 3300 |
| aagatgagaa cagaatgaag aacagatacg ggaatatcat tgcatacgat cattcccgag | 3360 |
| tgaggctgca gacaatagaa ggagacacaa actcagacta tatcaatggc aatttatcg | 3420 |
| atggttatca tcgacccaat cattacattg ctacccaagg gccaatgcag gaaaccatct | 3480 |
| atgacttctg gaggatggtg tggcacgaaa acactgcaag tatcatcatg gtgaccaatc | 3540 |
| ttgtggaagt gggaagggtc aaatgctgca atactggcc agatgacaca gagatatata | 3600 |
| aagcattaa agttacccta atagaaacag aactactggc agaatatgtg ataagaacat | 3660 |
| tgctgttga aaagagaggt gtgcatgaaa tccgagagat cagacagttt cacttcactg | 3720 |
| gctggccgga tcatggggtc cctaccatg ccaccgcct gctgggattc gtgcggcaag | 3780 |
| tcaagtccaa gagcccgccc agtgcaggcc cactggtggt gcactgcagt gctggtgcag | 3840 |
| ggaggactgg ctgtttcatc gtcattgata tcatgttgga catggccgaa agggaaggg | 3900 |
| tcgtagacat ctacaactgc gtcagggagc tgcggtcacg gagggtgaac atggtgcaaa | 3960 |
| cagaggagca gtatgtgttt atccacgatg cgatcctgga agcctgtctt tgtggggaca | 4020 |
| cctctgtgcc tgcttcccaa gttaggtctc tgtattatga catgaacaaa ctggatccac | 4080 |
| agacaaactc aagccagatt aaagaggaat tccggacgct aaacatggtg acaccaacgc | 4140 |
| tgcgagtaga ggactgcagc atcgcactgt gccccggaa ccatgagaaa accggtgca | 4200 |
| tggacatcct gccccagac cgctgcctgc ccttcctcat caccatcgat ggggagagca | 4260 |

|  |  |  |  |  |
|---|---|---|---|---|
| gcaactacat | caatgctgcc | ctcatggaca | gctataaaca | gccttcagct | tttatagtca | 4320 |
| cccagcatcc | tttgccaaac | acagtgaaag | acttttggag | actggtcctg | gattatcact | 4380 |
| gcacatccgt | agttatgcta | aatgatgtgg | atcctgccca | gttgtgtcca | cagtactggc | 4440 |
| cagaaaacgg | agtacacaga | cacggcccca | tccaggtgga | atttgtctct | gctgacctgg | 4500 |
| aagaggacat | catcagcagg | atattccgca | tttacaatgc | cgccagaccc | caagatggat | 4560 |
| atcggatggt | gcagcaattc | cagttcctgg | gctggccgat | gtacagggac | acaccagtgt | 4620 |
| ctaagcgctc | cttcttgaag | ctcattcgcc | aggtggacaa | gtggcaagag | gagtacaatg | 4680 |
| gcggggaagg | ccgcacggtt | gtgcactgct | gaacggggg | aggccgcagt | gggacgttct | 4740 |
| gcgccatcag | catcgtatgt | gagatgctcc | ggcaccagag | aaccgtggat | gtctttcacg | 4800 |
| ctgtgaagac | actgaggaac | aacaagccca | acatggtcga | cctcctggat | cagtacaagt | 4860 |
| tctgctacga | ggtggccctg | aatacttga | attctggctg | atggtgtaaa | cagctctgca | 4920 |
| aacaatccct | ttcataccac | aaagccaaga | cgttccatgg | tatttgtgca | aaagagatga | 4980 |
| agacttctca | atatgcttat | tttgcttgc | ataattggct | cttttaaga | gcccaagaaa | 5040 |
| gtgtttctaa | aattgcttgc | actgcccaat | cccagtaatg | ctgctgcctg | acagaaacac | 5100 |
| acacacagcc | acagttgcca | aatcccgtac | tccttgccac | cggcttccta | gagcagcgta | 5160 |
| gacagctggt | aaactgaaga | gcacaactat | attcttatga | aggaatttgt | acctttgggg | 5220 |
| tattattttg | tggcccgtga | ccctcgttat | tgttacagct | gagtgtatgt | ttttgttctg | 5280 |
| tggagaatgc | tatctggcat | tatggtaata | tattatttta | ggtaatatt | gtactttaac | 5340 |
| atgttgcata | atatatgctt | atgtagcttt | ccaggactaa | cagataaatg | tgtaatgaac | 5400 |
| aaagatatgt | tgtatgagtc | gtcgtttctg | tcagatttgt | attgtttcca | agggaaaagc | 5460 |
| ttggggagg | actcagttca | caaaatgcaa | aactcaacga | tcagattcac | ggacccagag | 5520 |
| cttttccatg | tgtttatatt | gtaaatattt | ttgatttcat | caaattattt | attcattaaa | 5580 |
| agaaattttt | gtgaagcaca | aaaaaaaaaa | aaaaaaaaa | aaaa |  | 5624 |

<210> SEQ ID NO 37
<211> LENGTH: 1465
<212> TYPE: PRT
<213> ORGANISM: homo sapiens

<400> SEQUENCE: 37

Met Arg Gly Leu Gly Thr Cys Leu Ala Thr Leu Ala Gly Leu Leu Leu
1               5                   10                  15

Thr Ala Ala Gly Glu Thr Phe Ser Gly Gly Cys Leu Phe Asp Glu Pro
                20                  25                  30

Tyr Ser Thr Cys Gly Tyr Ser Gln Ser Glu Gly Asp Asp Phe Asn Trp
            35                  40                  45

Glu Gln Val Asn Thr Leu Thr Lys Pro Thr Ser Asp Pro Trp Met Pro
        50                  55                  60

Ser Gly Ser Phe Met Leu Val Asn Ala Ser Gly Arg Pro Glu Gly Gln
65                  70                  75                  80

Arg Ala His Leu Leu Leu Pro Gln Leu Lys Glu Asn Asp Thr His Cys
                85                  90                  95

Ile Asp Phe His Tyr Phe Val Ser Ser Lys Ser Asn Ser Pro Pro Gly
                100                 105                 110

Leu Leu Asn Val Tyr Val Lys Val Asn Asn Gly Pro Leu Gly Asn Pro
            115                 120                 125

Ile Trp Asn Ile Ser Gly Asp Pro Thr Arg Thr Trp Asn Arg Ala Glu

```
              130              135              140
Leu Ala Ile Ser Thr Phe Trp Pro Asn Phe Tyr Gln Val Ile Phe Glu
145                 150                 155                 160

Val Ile Thr Ser Gly His Gln Gly Tyr Leu Ala Ile Asp Glu Val Lys
                165                 170                 175

Val Leu Gly His Pro Cys Thr Arg Thr Pro His Phe Leu Arg Ile Gln
                180                 185                 190

Asn Val Glu Val Asn Ala Gly Gln Phe Ala Thr Phe Gln Cys Ser Ala
                195                 200                 205

Ile Gly Arg Thr Val Ala Gly Asp Arg Leu Trp Leu Gln Gly Ile Asp
                210                 215                 220

Val Arg Asp Ala Pro Leu Lys Glu Ile Lys Val Thr Ser Ser Arg Arg
225                 230                 235                 240

Phe Ile Ala Ser Phe Asn Val Val Asn Thr Thr Lys Arg Asp Ala Gly
                245                 250                 255

Lys Tyr Arg Cys Met Ile Arg Thr Glu Gly Val Gly Ile Ser Asn
                260                 265                 270        Asn

Tyr Ala Glu Leu Val Val Lys Glu Pro Pro Val Pro Ile Ala Pro Pro
                275                 280                 285

Gln Leu Ala Ser Val Gly Ala Thr Tyr Leu Trp Ile Gln Leu Asn Ala
                290                 295                 300

Asn Ser Ile Asn Gly Asp Gly Pro Ile Val Ala Arg Glu Val Glu Tyr
305                 310                 315                 320

Cys Thr Ala Ser Gly Ser Trp Asn Asp Arg Gln Pro Val Asp Ser Thr
                325                 330                 335

Ser Tyr Lys Ile Gly His Leu Asp Pro Asp Thr Glu Tyr Glu Ile Ser
                340                 345                 350

Val Leu Leu Thr Arg Pro Gly Glu Gly Gly Thr Gly Ser Pro Gly Pro
                355                 360                 365

Ala Leu Arg Thr Arg Thr Lys Cys Ala Asp Pro Met Arg Gly Pro Arg
                370                 375                 380

Lys Leu Glu Val Val Glu Val Lys Ser Arg Gln Ile Thr Ile Arg Trp
385                 390                 395                 400

Glu Pro Phe Gly Tyr Asn Val Thr Arg Cys His Ser Tyr Asn Leu Thr
                405                 410                 415

Val His Tyr Cys Tyr Gln Val Gly Gly Gln Glu Gln Val Arg Glu Glu
                420                 425                 430

Val Ser Trp Asp Thr Glu Asn Ser His Pro Gln His Thr Ile Thr Asn
                435                 440                 445

Leu Ser Pro Tyr Thr Asn Val Ser Val Lys Leu Ile Leu Met Asn Pro
450                 455                 460

Glu Gly Arg Lys Glu Ser Gln Glu Leu Ile Val Gln Thr Asp Glu Asp
465                 470                 475                 480

Leu Pro Gly Ala Val Pro Thr Glu Ser Ile Gln Gly Ser Thr Phe Glu
                485                 490                 495

Glu Lys Ile Phe Leu Gln Trp Arg Glu Pro Thr Gln Thr Tyr Gly Val
                500                 505                 510

Ile Thr Leu Tyr Glu Ile Thr Tyr Lys Ala Val Ser Ser Phe Asp Pro
                515                 520                 525

Glu Ile Asp Leu Ser Asn Gln Ser Gly Arg Val Ser Lys Leu Gly Asn
                530                 535                 540

Glu Thr His Phe Leu Phe Phe Gly Leu Tyr Pro Gly Thr Thr Tyr Ser
545                 550                 555                 560
```

```
Phe Thr Ile Arg Ala Ser Thr Ala Lys Gly Phe Gly Pro Pro Ala Thr
                565                 570                 575

Asn Gln Phe Thr Thr Lys Ile Ser Ala Pro Ser Met Pro Ala Tyr Glu
            580                 585                 590

Leu Glu Thr Pro Leu Asn Gln Thr Asp Asn Thr Val Thr Val Met Leu
        595                 600                 605

Lys Pro Ala His Ser Arg Gly Ala Pro Val Ser Val Tyr Gln Ile Val
    610                 615                 620

Val Glu Glu Glu Arg Pro Arg Arg Thr Lys Lys Thr Thr Glu Ile Leu
625                 630                 635                 640

Lys Cys Tyr Pro Val Pro Ile His Phe Gln Asn Ala Ser Leu Leu Asn
                645                 650                 655

Ser Gln Tyr Tyr Phe Ala Ala Glu Phe Pro Ala Asp Ser Leu Gln Ala
            660                 665                 670

Ala Gln Pro Phe Thr Ile Gly Asp Asn Lys Thr Tyr Asn Gly Tyr Trp
        675                 680                 685

Asn Thr Pro Leu Leu Pro Tyr Lys Ser Tyr Arg Ile Tyr Phe Gln Ala
    690                 695                 700

Ala Ser Arg Ala Asn Gly Glu Thr Lys Ile Asp Cys Val Gln Val Ala
705                 710                 715                 720

Thr Lys Gly Ala Ala Thr Pro Lys Pro Val Pro Glu Pro Glu Lys Gln
                725                 730                 735

Thr Asp His Thr Val Lys Ile Ala Gly Val Ile Ala Gly Ile Leu Leu
            740                 745                 750

Phe Val Ile Ile Phe Leu Gly Val Leu Val Met Lys Lys Arg Lys
        755                 760                 765

Leu Ala Lys Lys Arg Lys Glu Thr Met Ser Ser Thr Arg Gln Glu Met
    770                 775                 780

Thr Val Met Val Asn Ser Met Asp Lys Ser Tyr Ala Glu Gln Gly Thr
785                 790                 795                 800

Asn Cys Asp Glu Ala Phe Ser Phe Met Asp Thr His Asn Leu Asn Gly
                805                 810                 815

Arg Ser Val Ser Ser Pro Ser Ser Phe Thr Met Lys Thr Asn Thr Leu
            820                 825                 830

Ser Thr Ser Val Pro Asn Ser Tyr Tyr Pro Asp Pro Phe Val Pro Thr
        835                 840                 845

Ala Ile Leu Val Pro Ile Asn Asp Glu Thr His Thr Met Ala Ser Asp
    850                 855                 860

Thr Ser Ser Leu Val Gln Ser His Thr Tyr Lys Lys Arg Glu Pro Ala
865                 870                 875                 880

Asp Val Pro Tyr Gln Thr Gly Gln Leu His Pro Ala Ile Arg Val Ala
                885                 890                 895

Asp Leu Leu Gln His Ile Thr Gln Met Lys Cys Ala Glu Gly Tyr Gly
            900                 905                 910

Phe Lys Glu Glu Tyr Glu Ser Phe Phe Glu Gly Gln Ser Ala Pro Trp
        915                 920                 925

Asp Ser Ala Lys Lys Asp Glu Asn Arg Met Lys Asn Arg Tyr Gly Asn
    930                 935                 940

Ile Ile Ala Tyr Asp His Ser Arg Val Arg Leu Gln Thr Ile Glu Gly
945                 950                 955                 960

Asp Thr Asn Ser Asp Tyr Ile Asn Gly Asn Tyr Ile Asp Gly Tyr His
                965                 970                 975
```

```
Arg Pro Asn His Tyr Ile Ala Thr Gln Gly Pro Met Gln Glu Thr Ile
            980                 985                 990

Tyr Asp Phe Trp Arg Met Val Trp His Glu Asn Thr Ala Ser Ile Ile
        995                1000                1005

Met Val Thr Asn Leu Val Glu Val Gly Arg Val Lys Cys Cys Lys
    1010                1015                1020

Tyr Trp Pro Asp Asp Thr Glu Ile Tyr Lys Asp Ile Lys Val Thr
    1025                1030                1035

Leu Ile Glu Thr Glu Leu Leu Ala Glu Tyr Val Ile Arg Thr Phe
    1040                1045                1050

Ala Val Glu Lys Arg Gly Val His Glu Ile Arg Glu Ile Arg Gln
    1055                1060                1065

Phe His Phe Thr Gly Trp Pro Asp His Gly Val Pro Tyr His Ala
    1070                1075                1080

Thr Gly Leu Leu Gly Phe Val Arg Gln Val Lys Ser Lys Ser Pro
    1085                1090                1095

Pro Ser Ala Gly Pro Leu Val Val His Cys Ser Ala Gly Ala Gly
    1100                1105                1110

Arg Thr Gly Cys Phe Ile Val Ile Asp Ile Met Leu Asp Met Ala
    1115                1120                1125

Glu Arg Glu Gly Val Val Asp Ile Tyr Asn Cys Val Arg Glu Leu
    1130                1135                1140

Arg Ser Arg Arg Val Asn Met Val Gln Thr Glu Glu Gln Tyr Val
    1145                1150                1155

Phe Ile His Asp Ala Ile Leu Glu Ala Cys Leu Cys Gly Asp Thr
    1160                1165                1170

Ser Val Pro Ala Ser Gln Val Arg Ser Leu Tyr Tyr Asp Met Asn
    1175                1180                1185

Lys Leu Asp Pro Gln Thr Asn Ser Ser Gln Ile Lys Glu Glu Phe
    1190                1195                1200

Arg Thr Leu Asn Met Val Thr Pro Thr Leu Arg Val Glu Asp Cys
    1205                1210                1215

Ser Ile Ala Leu Leu Pro Arg Asn His Glu Lys Asn Arg Cys Met
    1220                1225                1230

Asp Ile Leu Pro Pro Asp Arg Cys Leu Pro Phe Leu Ile Thr Ile
    1235                1240                1245

Asp Gly Glu Ser Ser Asn Tyr Ile Asn Ala Ala Leu Met Asp Ser
    1250                1255                1260

Tyr Lys Gln Pro Ser Ala Phe Ile Val Thr Gln His Pro Leu Pro
    1265                1270                1275

Asn Thr Val Lys Asp Phe Trp Arg Leu Val Leu Asp Tyr His Cys
    1280                1285                1290

Thr Ser Val Val Met Leu Asn Asp Val Asp Pro Ala Gln Leu Cys
    1295                1300                1305

Pro Gln Tyr Trp Pro Glu Asn Gly Val His Arg His Gly Pro Ile
    1310                1315                1320

Gln Val Glu Phe Val Ser Ala Asp Leu Glu Glu Asp Ile Ile Ser
    1325                1330                1335

Arg Ile Phe Arg Ile Tyr Asn Ala Ala Arg Pro Gln Asp Gly Tyr
    1340                1345                1350

Arg Met Val Gln Gln Phe Gln Phe Leu Gly Trp Pro Met Tyr Arg
    1355                1360                1365

Asp Thr Pro Val Ser Lys Arg Ser Phe Leu Lys Leu Ile Arg Gln
```

| | | | | | | | | | |
|---|---|---|---|---|---|---|---|---|---|
| | | 1370 | | | | 1375 | | | 1380 |
| Val | Asp | Lys | Trp | Gln | Glu | Glu | Tyr | Asn | Gly | Gly | Glu | Gly | Arg | Thr |
| 1385 | | | | | 1390 | | | | | 1395 | | | | |

Val Val His Cys Leu Asn Gly Gly Gly Arg Ser Gly Thr Phe Cys
1400 1405 1410

Ala Ile Ser Ile Val Cys Glu Met Leu Arg His Gln Arg Thr Val
1415 1420 1425

Asp Val Phe His Ala Val Lys Thr Leu Arg Asn Asn Lys Pro Asn
1430 1435 1440

Met Val Asp Leu Leu Asp Gln Tyr Lys Phe Cys Tyr Glu Val Ala
1445 1450 1455

Leu Glu Tyr Leu Asn Ser Gly
1460 1465

<210> SEQ ID NO 38
<211> LENGTH: 5585
<212> TYPE: DNA
<213> ORGANISM: homo sapiens

<400> SEQUENCE: 38

```
agtcagtcgg ggagcaagag ccccgcgcgc agccggcgcg ggctcggtca tcggcgcgcc      60
gccgcccggg gctgggcttg gggctgcctg tggagaggcg gcgggcggaa cgcgcgcggc     120
cacggccacg gccaccgcca cggccacggc cggcagctcg gtcccgggt cccgggcagg      180
ggaaggggag aggcggcgag ctcagcaacc ggaaccgagg gaagattttg gctccgcggg     240
ctcgccctcc gctccctctg ccagcggcgc cagacgccga gtggggccag ggacagggga     300
ggaggaccca ggaccctgtg cccgcgcccc tggagccgct ggagttcgga cttctgcaac     360
tgttggcact ttgggggctt ggcttagcgc tctgctgttt acccgtctct cctcgctgcc     420
tcggaaccaa agctcccggc ccctccgcc ctcgcgcgcc acccaccgc cgccggggag       480
cggcccggcc cgcactcagc accatgaggg acttgggac ttgcctggcg actttggccg      540
gactttgct aactgcggcg ggcgagacgt tctcaggtgg ctgcctcttt gatgagccgt      600
atagcacatg tggatatagt caatctgaag gtgatgactt caattgggag caagtgaaca     660
ccttgactaa accgacttct gatccatgga tgccatcagg ttctttcatg ctggtgaatg     720
cctctgggag acctgagggg cagagagccc acctgctctt accccaactt aaagaaaatg     780
acacccactg catcgatttt cactattttg tgtccagcaa gagtaattct cctccggggt     840
tactcaatgt ctacgtgaag gtcaataacg ggccactggg gaatcctatc tggaatatat     900
ctggagaccc aacacgtaca tggaacaggg cagaactggc cattagtact ttctggccta     960
acttttatca ggtgattttt gaagtgataa cttctggaca tcaaggctat ctcgctatcg    1020
atgaggtgaa ggtgttagga catccatgta ccaggactcc tcacttcctg cggattcaga    1080
atgtggaagt taatgctggc cagtttgcta ccttccagtg cagtgccatc ggcaggaccg    1140
tggcaggaga caggctctgg ttacagggca ttgatgtgcg agatgctcct ctgaaggaaa    1200
tcaaggtgac cagctcccga cgcttcattg cttcatttaa tgttgtgaat accaccaaac    1260
gagatgctgg aaaagtaccg ctgcatgatt cgcactgaagg aggtgttgga atatcaaact    1320
atgcagagtt ggtagttaaa gaaccacccg ttcctattgc cccacctcag ctcgcctctg    1380
taggagccac ctacctgtgg atacagctca acgccaactc catcaatggg gatgggccca    1440
ttgtggcccg agaggtggag tactgcacgg ccagtgggag ctggaatgac cggcagccag    1500
tcgattccac gagctataaa attggacacc ttgacccaga tacagaatat gagattagtg    1560
```

```
tgctcctgac caggccaggg gagggtggca ctggctctcc tggtccagct ctcaggacaa   1620
gaacaaagtg tgctgatccc atgcgaggcc caagaaaact agaagtagtg gaggtcaaat   1680
ctcggcaaat cactatccgc tgggagccat ttggatataa tgtaactcgt tgccacagtt   1740
ataatctcac tgtccactac tgttaccaag ttggaggaca agaacaagtg cgagaagaag   1800
taagctggga tacagaaaac tcacaccctc aacacacgat cactaacctg tcaccataca   1860
ccaatgtcag tgtgaaactg atcctcatga acccagaggg ccggaaggaa agccaagaac   1920
tcatagtgca gacagatgaa gacctcccag gtgctgttcc cactgaatcc atacaaggaa   1980
gtacctttga agagaagata tttcttcagt ggagagaacc aactcaaaca tatggtgtaa   2040
tcactttata tgagatcacc tacaaagcag tcagttcctt tgacccagaa atagatttat   2100
ccaatcagag tggaagagtt tcaaagctgg gaaatgaaac ccattttctg ttttttggac   2160
tgtatccggg gaccacatac tcctttacca tccgagctag cacagctaag ggttttgggc   2220
ctccagcaac aaaccagttc accaccaaaa tatcagcacc ctctatgcca gcttatgaac   2280
ttgagacacc tttgaatcaa actgacaata ccgtgacagt catgctgaaa cctgcccaca   2340
gcagaggagc acctgtcagt gtctatcaaa tagttgttga ggaagaacgt cctcgaagaa   2400
ctaaaaagac gacagaaatc ttaaagtgct acccagtgcc aattcacttc cagaatgctt   2460
ctctgctgaa ctcacagtac tactttgctg cagaatttcc tgcagacagc ctccaagctg   2520
cgcagccttt tacaattggt gataataaga catataatgg atactggaac actcccctcc   2580 tccctataa aagctacaga atttatttcc aagctgctag tagagccaat ggggaaacca   2640
aaatagactg tgtccaagtg gccacaaaag gagctgccac tccgaaacca gtcccagaac   2700
ccgagaaaca gacagaccat acagttaaaa ttgctggagt catcgcgggc atcttgctgt   2760
tcgtgattat atttcttgga gttgtgttgg taatgaagaa aaggaaactg gccaagaagc   2820
ggaaagagac catgagcagc acccgacagg agatgactgt gatggtgaac tcaatggaca   2880
agagctatgc tgagcagggc acaaactgcg acgaggcttt tcattcatg gacacgcaca   2940 atctgaatgg gagatctgtg tcttcaccat cgtccttcac aatgaaaaca aatacactga   3000
gcacatcggt gcctaattcc tattacccag atgaaaccca caatggcc agcgatacca   3060 gcagcctggt gcagtcccat acttacaaga gcgagagcc ggccgacgtg ccctatcaga   3120
ctgggcagct ccaccccgcc atccgggtgg cagacctcct tcagcacatc acacagatga   3180
agtgtgcgga gggctacggc ttcaaggagg aatacgagag cttctttgaa gggcagtctg   3240
caccatggga ctcggctaag aaagatgaga acagaatgaa gaacagatac gggaatatca   3300
ttgcatacga tcattcccga gtgaggctgc agacaataga aggagacaca aactcagact   3360
atatcaatgg caattatatc gatggttatc atcgacccaa tcattacatt gctacccaag   3420
ggccaatgca ggaaaccatc tatgacttct ggaggatggt gtggcacgaa aacactgcaa   3480
gtatcatcat ggtgaccaat cttgtggaag tgggaaggggt caaatgctgc aaatactggc   3540
cagatgacac agagatatat aaagacatta agttaccct aatagaaaca gaactactgg   3600
cagaatatgt gataagaaca tttgctgttg aaaagagagg tgtgcatgaa atccgagaga   3660
tcagacagtt tcacttcact ggctggccgg atcatgggt cccctaccat gccaccggcc   3720
tgctgggatt cgtgcggcaa gtcaagtcca agagcccgcc cagtgcaggc ccactggtgg   3780
tgcactgcag tgctggtgca gggaggactg gctgtttcat cgtcattgat atcatgttgg   3840
acatggccga aagggaaggg gtcgtagaca tctacaactg cgtcagggag ctgcggtcac   3900
```

-continued

```
ggagggtgaa catggtgcaa acagaggagc agtatgtgtt tatccacgat gcgatcctgg    3960
aagcctgtct ttgtggggac acctctgtgc ctgcttccca agttaggtct ctgtattatg    4020
acatgaacaa actggatcca cagacaaact caagccagat aaagaggaa ttccggacgc     4080
taaacatggt gacaccaacg ctgcgagtag aggactgcag catcgcactg ttgcccggga    4140
accatgagaa aaaccggtgc atggacatcc tgccccaga ccgctgcctg cccttcctca     4200
tcaccatcga tggggagagc agcaactaca tcaatgctgc cctcatggac agctataaac    4260
agccttcagc ttttatagtc acccagcatc ctttgccaaa cacagtgaaa gacttttgga    4320
gactggtcct ggattatcac tgcacatccg tagttatgct aaatgatgtg atcctgccc     4380
agttgtgtcc acagtactgg ccagaaaacg gagtacacag acacggcccc atccaggtgg    4440
aatttgtctc tgctgacctg aagaggaca tcatcagcag gatattccgc atttacaatg     4500
ccgccagacc ccaagatgga tatcggatgg tgcagcaatt ccagttcctg ggctggccga    4560
tgtacaggga cacaccagtg tctaagcgct ccttcttgaa gctcattcgc caggtggaca    4620
agtggcaaga ggagtacaat ggcggggaag gccgcacggt tgtgcactgc ttgaacgggg    4680
gaggccgcag tgggacgttc tgcgccatca gcatcgtatg tgagatgctc cggcaccaga    4740
gaaccgtgga tgtcttttcac gctgtgaaga cactgaggaa caacaagccc aacatggtcg    4800
acctcctgga tcagtacaag ttctgctacg aggtggccct ggaatacttg aattctggct    4860
gatggtgtaa acagctctgc aaacaatccc tttcatacca caaagccaag acgttccatg    4920
gtatttgtgc aaaagagatg aagacttctc aatatgctta ttttgctttg cataattggc    4980
tcttttaag agcccaagaa agtgtttcta aaattgcttg cactgcccaa tcccagtaat    5040
gctgctgcct gacagaaaca cacacacagc cacagttgcc aaatcccgta ctccttgcca    5100
ccggcttcct agagcagcgt agacagctgg taaactgaag agcacaacta tattcttatg    5160
aaggaatttg tacctttggg gtattatttt gtggcccgtg accctcgtta ttgttacagc    5220
tgagtgtatg tttttgttct gtggagaatg ctatctggca ttatggtaat atattatttt    5280
aggtaatatt tgtactttaa catgttgcat aatatatgct tatgtagctt tccaggacta    5340
acagataaat gtgtaatgaa caaagatatg ttgtatgagt cgtcgtttct gtcagatttg    5400
tattgtttcc aagggaaaag cttggggggag gactcagttc acaaaatgca aaactcaacg    5460
atcagattca cggacccaga gcttttccat gtgtttatat tgtaaatatt tttgatttca    5520
tcaaattatt tattcattaa aagaaatttt tgtgaagcac aaaaaaaaaa aaaaaaaaa    5580
aaaaa                                                                 5585
```

<210> SEQ ID NO 39
<211> LENGTH: 1452
<212> TYPE: PRT
<213> ORGANISM: homo sapiens

<400> SEQUENCE: 39

Met Arg Gly Leu Gly Thr Cys Leu Ala Thr Leu Ala Gly Leu Leu Leu
1               5                   10                  15

Thr Ala Ala Gly Glu Thr Phe Ser Gly Gly Cys Leu Phe Asp Glu Pro
            20                  25                  30

Tyr Ser Thr Cys Gly Tyr Ser Gln Ser Glu Gly Asp Asp Phe Asn Trp
        35                  40                  45

Glu Gln Val Asn Thr Leu Thr Lys Pro Thr Ser Asp Pro Trp Met Pro
    50                  55                  60

Ser Gly Ser Phe Met Leu Val Asn Ala Ser Gly Arg Pro Glu Gly Gln

-continued

```
             65                  70                  75                  80
Arg Ala His Leu Leu Pro Gln Leu Lys Glu Asn Asp Thr His Cys
                 85                  90                  95

Ile Asp Phe His Tyr Phe Val Ser Ser Lys Ser Asn Ser Pro Pro Gly
                100                 105                 110

Leu Leu Asn Val Tyr Val Lys Val Asn Asn Gly Pro Leu Gly Asn Pro
                115                 120                 125

Ile Trp Asn Ile Ser Gly Asp Pro Thr Arg Thr Trp Asn Arg Ala Glu
    130                 135                 140

Leu Ala Ile Ser Thr Phe Trp Pro Asn Phe Tyr Gln Val Ile Phe Glu
145                 150                 155                 160

Val Ile Thr Ser Gly His Gln Gly Tyr Leu Ala Ile Asp Glu Val Lys
                165                 170                 175

Val Leu Gly His Pro Cys Thr Arg Thr Pro His Phe Leu Arg Ile Gln
                180                 185                 190

Asn Val Glu Val Asn Ala Gly Gln Phe Ala Thr Phe Gln Cys Ser Ala
                195                 200                 205

Ile Gly Arg Thr Val Ala Gly Asp Arg Leu Trp Leu Gln Gly Ile Asp
    210                 215                 220

Val Arg Asp Ala Pro Leu Lys Glu Ile Lys Val Thr Ser Ser Arg Arg
225                 230                 235                 240

Phe Ile Ala Ser Phe Asn Val Val Asn Thr Thr Lys Arg Asp Ala Gly
                245                 250                 255

Lys Tyr Arg Cys Met Ile Arg Thr Glu Gly Gly Val Gly Ile Ser Asn
                260                 265                 270

Tyr Ala Glu Leu Val Val Lys Glu Pro Pro Val Pro Ile Ala Pro Pro
                275                 280                 285

Gln Leu Ala Ser Val Gly Ala Thr Tyr Leu Trp Ile Gln Leu Asn Ala
    290                 295                 300

Asn Ser Ile Asn Gly Asp Gly Pro Ile Val Ala Arg Glu Val Glu Tyr
305                 310                 315                 320

Cys Thr Ala Ser Gly Ser Trp Asn Asp Arg Gln Pro Val Asp Ser Thr
                325                 330                 335

Ser Tyr Lys Ile Gly His Leu Asp Pro Asp Thr Glu Tyr Glu Ile Ser
                340                 345                 350

Val Leu Leu Thr Arg Pro Gly Glu Gly Gly Thr Gly Ser Pro Gly Pro
                355                 360                 365

Ala Leu Arg Thr Arg Thr Lys Cys Ala Asp Pro Met Arg Gly Pro Arg
    370                 375                 380

Lys Leu Glu Val Val Glu Val Lys Ser Arg Gln Ile Thr Ile Arg Trp
385                 390                 395                 400

Glu Pro Phe Gly Tyr Asn Val Thr Arg Cys His Ser Tyr Asn Leu Thr
                405                 410                 415

Val His Tyr Cys Tyr Gln Val Gly Gly Gln Glu Gln Val Arg Glu Glu
                420                 425                 430

Val Ser Trp Asp Thr Glu Asn Ser His Pro Gln His Thr Ile Thr Asn
    435                 440                 445

Leu Ser Pro Tyr Thr Asn Val Ser Val Lys Leu Ile Leu Met Asn Pro
    450                 455                 460

Glu Gly Arg Lys Glu Ser Gln Glu Leu Ile Val Gln Thr Asp Glu Asp
465                 470                 475                 480

Leu Pro Gly Ala Val Pro Thr Glu Ser Ile Gln Gly Ser Thr Phe Glu
                485                 490                 495
```

-continued

Glu Lys Ile Phe Leu Gln Trp Arg Glu Pro Thr Gln Thr Tyr Gly Val
              500                 505                 510

Ile Thr Leu Tyr Glu Ile Thr Tyr Lys Ala Val Ser Ser Phe Asp Pro
              515                 520                 525

Glu Ile Asp Leu Ser Asn Gln Ser Gly Arg Val Ser Lys Leu Gly Asn
              530                 535                 540

Glu Thr His Phe Leu Phe Phe Gly Leu Tyr Pro Gly Thr Thr Tyr Ser
545                 550                 555                 560

Phe Thr Ile Arg Ala Ser Thr Ala Lys Gly Phe Gly Pro Pro Ala Thr
              565                 570                 575

Asn Gln Phe Thr Thr Lys Ile Ser Ala Pro Ser Met Pro Ala Tyr Glu
              580                 585                 590

Leu Glu Thr Pro Leu Asn Gln Thr Asp Asn Thr Val Thr Val Met Leu
              595                 600                 605

Lys Pro Ala His Ser Arg Gly Ala Pro Val Ser Val Tyr Gln Ile Val
              610                 615                 620

Val Glu Glu Glu Arg Pro Arg Arg Thr Lys Lys Thr Thr Glu Ile Leu
625                 630                 635                 640

Lys Cys Tyr Pro Val Pro Ile His Phe Gln Asn Ala Ser Leu Leu Asn
              645                 650                 655

Ser Gln Tyr Tyr Phe Ala Ala Glu Phe Pro Ala Asp Ser Leu Gln Ala
              660                 665                 670

Ala Gln Pro Phe Thr Ile Gly Asp Asn Lys Thr Tyr Asn Gly Tyr Trp
              675                 680                 685

Asn Thr Pro Leu Leu Pro Tyr Lys Ser Tyr Arg Ile Tyr Phe Gln Ala
              690                 695                 700

Ala Ser Arg Ala Asn Gly Glu Thr Lys Ile Asp Cys Val Gln Val Ala
705                 710                 715                 720

Thr Lys Gly Ala Ala Thr Pro Lys Pro Val Pro Glu Pro Glu Lys Gln
              725                 730                 735

Thr Asp His Thr Val Lys Ile Ala Gly Val Ile Ala Gly Ile Leu Leu
              740                 745                 750

Phe Val Ile Ile Phe Leu Gly Val Val Leu Val Met Lys Lys Arg Lys
              755                 760                 765

Leu Ala Lys Lys Arg Lys Glu Thr Met Ser Ser Thr Arg Gln Glu Met
              770                 775                 780

Thr Val Met Val Asn Ser Met Asp Lys Ser Tyr Ala Glu Gln Gly Thr
785                 790                 795                 800

Asn Cys Asp Glu Ala Phe Ser Phe Met Asp Thr His Asn Leu Asn Gly
              805                 810                 815

Arg Ser Val Ser Ser Pro Ser Ser Phe Thr Met Lys Thr Asn Thr Leu
              820                 825                 830

Ser Thr Ser Val Pro Asn Ser Tyr Tyr Pro Asp Glu Thr His Thr Met
              835                 840                 845

Ala Ser Asp Thr Ser Ser Leu Val Gln Ser His Thr Tyr Lys Lys Arg
              850                 855                 860

Glu Pro Ala Asp Val Pro Tyr Gln Thr Gly Gln Leu His Pro Ala Ile
865                 870                 875                 880

Arg Val Ala Asp Leu Leu Gln His Ile Thr Gln Met Lys Cys Ala Glu
              885                 890                 895

Gly Tyr Gly Phe Lys Glu Glu Tyr Glu Ser Phe Phe Glu Gly Gln Ser
              900                 905                 910

Ala Pro Trp Asp Ser Ala Lys Lys Asp Glu Asn Arg Met Lys Asn Arg
            915                 920                 925

Tyr Gly Asn Ile Ile Ala Tyr Asp His Ser Arg Val Arg Leu Gln Thr
        930                 935                 940

Ile Glu Gly Asp Thr Asn Ser Asp Tyr Ile Asn Gly Asn Tyr Ile Asp
945                 950                 955                 960

Gly Tyr His Arg Pro Asn His Tyr Ile Ala Thr Gln Gly Pro Met Gln
                965                 970                 975

Glu Thr Ile Tyr Asp Phe Trp Arg Met Val Trp His Glu Asn Thr Ala
            980                 985                 990

Ser Ile Ile Met Val Thr Asn Leu Val Glu Val Gly Arg Val Lys Cys
        995                 1000                1005

Cys Lys Tyr Trp Pro Asp Asp Thr Glu Ile Tyr Lys Asp Ile Lys
    1010                1015                1020

Val Thr Leu Ile Glu Thr Glu Leu Leu Ala Glu Tyr Val Ile Arg
    1025                1030                1035

Thr Phe Ala Val Glu Lys Arg Gly Val His Glu Ile Arg Glu Ile
    1040                1045                1050

Arg Gln Phe His Phe Thr Gly Trp Pro Asp His Gly Val Pro Tyr
    1055                1060                1065

His Ala Thr Gly Leu Leu Gly Phe Val Arg Gln Val Lys Ser Lys
    1070                1075                1080

Ser Pro Pro Ser Ala Gly Pro Leu Val Val His Cys Ser Ala Gly
    1085                1090                1095

Ala Gly Arg Thr Gly Cys Phe Ile Val Ile Asp Ile Met Leu Asp
    1100                1105                1110

Met Ala Glu Arg Glu Gly Val Val Asp Ile Tyr Asn Cys Val Arg
    1115                1120                1125

Glu Leu Arg Ser Arg Arg Val Asn Met Val Gln Thr Glu Glu Gln
    1130                1135                1140

Tyr Val Phe Ile His Asp Ala Ile Leu Glu Ala Cys Leu Cys Gly
    1145                1150                1155

Asp Thr Ser Val Pro Ala Ser Gln Val Arg Ser Leu Tyr Tyr Asp
    1160                1165                1170

Met Asn Lys Leu Asp Pro Gln Thr Asn Ser Ser Gln Ile Lys Glu
    1175                1180                1185

Glu Phe Arg Thr Leu Asn Met Val Thr Pro Thr Leu Arg Val Glu
    1190                1195                1200

Asp Cys Ser Ile Ala Leu Leu Pro Arg Asn His Glu Lys Asn Arg
    1205                1210                1215

Cys Met Asp Ile Leu Pro Pro Asp Arg Cys Leu Pro Phe Leu Ile
    1220                1225                1230

Thr Ile Asp Gly Glu Ser Ser Asn Tyr Ile Asn Ala Ala Leu Met
    1235                1240                1245

Asp Ser Tyr Lys Gln Pro Ser Ala Phe Ile Val Thr Gln His Pro
    1250                1255                1260

Leu Pro Asn Thr Val Lys Asp Phe Trp Arg Leu Val Leu Asp Tyr
    1265                1270                1275

His Cys Thr Ser Val Val Met Leu Asn Asp Val Asp Pro Ala Gln
    1280                1285                1290

Leu Cys Pro Gln Tyr Trp Pro Glu Asn Gly Val His Arg His Gly
    1295                1300                1305

Pro Ile Gln Val Glu Phe Val Ser Ala Asp Leu Glu Glu Asp Ile

```
              1310                1315                1320
Ile Ser Arg Ile Phe Arg Ile Tyr Asn Ala Ala Arg Pro Gln Asp
              1325                1330                1335

Gly Tyr Arg Met Val Gln Gln Phe Gln Phe Leu Gly Trp Pro Met
              1340                1345                1350

Tyr Arg Asp Thr Pro Val Ser Lys Arg Ser Phe Leu Lys Leu Ile
              1355                1360                1365

Arg Gln Val Asp Lys Trp Gln Glu Glu Tyr Asn Gly Gly Glu Gly
              1370                1375                1380

Arg Thr Val Val His Cys Leu Asn Gly Gly Gly Arg Ser Gly Thr
              1385                1390                1395

Phe Cys Ala Ile Ser Ile Val Cys Glu Met Leu Arg His Gln Arg
              1400                1405                1410

Thr Val Asp Val Phe His Ala Val Lys Thr Leu Arg Asn Asn Lys
              1415                1420                1425

Pro Asn Met Val Asp Leu Leu Asp Gln Tyr Lys Phe Cys Tyr Glu
              1430                1435                1440

Val Ala Leu Glu Tyr Leu Asn Ser Gly
              1445                1450
```